US011253357B2

(12) United States Patent
Naor et al.

(10) Patent No.: US 11,253,357 B2
(45) Date of Patent: Feb. 22, 2022

(54) MULTI-LEVEL CARDIAC IMPLANT

(71) Applicant: Mitrassist Medical Ltd., Caesarea (IL)

(72) Inventors: Gil Naor, Hofit (IL); Gideon Meyer-Brodnitz, Yokneam (IL)

(73) Assignee: Mitrassist Medical Ltd., Caesarea (IL)

( * ) Notice: Subject to any disclaimer, the term of this patent is extended or adjusted under 35 U.S.C. 154(b) by 147 days.

(21) Appl. No.: 16/476,880

(22) PCT Filed: Jan. 11, 2018

(86) PCT No.: PCT/IL2018/050050
§ 371 (c)(1),
(2) Date: Jul. 10, 2019

(87) PCT Pub. No.: WO2018/131043
PCT Pub. Date: Jul. 19, 2018

(65) Prior Publication Data
US 2019/0336280 A1 Nov. 7, 2019

Related U.S. Application Data

(60) Provisional application No. 62/444,835, filed on Jan. 11, 2017.

(51) Int. Cl.
*A61F 2/24* (2006.01)
*B29C 48/13* (2019.01)
(Continued)

(52) U.S. Cl.
CPC ............ *A61F 2/2418* (2013.01); *A61F 2/243* (2013.01); *A61F 2/2415* (2013.01);
(Continued)

(58) Field of Classification Search
CPC .................................................. A61F 2/2418
See application file for complete search history.

(56) References Cited

U.S. PATENT DOCUMENTS 7,381,220 B2   6/2008 Macoviak et al.
8,579,964 B2   11/2013 Lane et al.
(Continued)

FOREIGN PATENT DOCUMENTS

WO  WO 2004/030568   4/2004
WO  WO 2004/089250   10/2004
(Continued)

OTHER PUBLICATIONS

International Preliminary Report on Patentability dated Jul. 25, 2019 From the International Bureau of WIPO Re. Application No. PCT/IL2018/050049. (11 Pages).
(Continued)

*Primary Examiner* — Suba Ganesan

(57) ABSTRACT

A heart valve prosthesis including a frame, the frame including a plurality of struts designed to extend from an upstream side of a natural heart valve to a downstream side of the natural heart valve, and a plurality of connectors attached to the plurality of struts, wherein the plurality of connectors are arranged as arcs connecting the struts, the arcs having two ends, each end attached to one of the struts, and a peak pointing from a center of the frame circumferentially outward and toward the upstream side of the frame, and the plurality of connectors are arranged as at least two rows, each row circumnavigating the center lumen of the frame. Related apparatus and methods are also described.

20 Claims, 47 Drawing Sheets
(15 of 47 Drawing Sheet(s) Filed in Color)

(51) Int. Cl.
  *B29C 48/151* (2019.01)
  *A61F 2/91* (2013.01)
  *A61F 2/82* (2013.01)
  *B29K 705/08* (2006.01)
  *B29L 31/00* (2006.01)

(52) U.S. Cl.
  CPC .......... *A61F 2/2445* (2013.01); *A61F 2/2466* (2013.01); *B29C 48/13* (2019.02); *B29C 48/151* (2019.02); *A61F 2/91* (2013.01); *A61F 2002/825* (2013.01); *A61F 2210/0014* (2013.01); *A61F 2220/0075* (2013.01); *A61F 2230/0065* (2013.01); *A61F 2230/0093* (2013.01); *A61F 2250/0039* (2013.01); *B29K 2705/08* (2013.01); *B29L 2031/7534* (2013.01)

(56) References Cited

U.S. PATENT DOCUMENTS

| | | |
|---|---|---|
| 2001/0010017 A1 | 7/2001 | Letac et al. |
| 2003/0199975 A1 | 10/2003 | Gabbay |
| 2004/0127981 A1 | 7/2004 | Rahdert et al. |
| 2006/0058871 A1 | 3/2006 | Zakay et al. |
| 2007/0156233 A1 | 7/2007 | Kapadia et al. |
| 2007/0185571 A1 | 8/2007 | Kapadia et al. |
| 2007/0270943 A1 | 11/2007 | Solem et al. |
| 2009/0292350 A1 | 11/2009 | Eberhardt et al. |
| 2010/0280606 A1 | 11/2010 | Naor |
| 2011/0137397 A1 | 6/2011 | Chau et al. |
| 2012/0022640 A1 | 1/2012 | Gross et al. |
| 2013/0046378 A1 | 2/2013 | Millwee et al. |
| 2014/0052237 A1 | 2/2014 | Lane et al. |
| 2014/0222136 A1 | 8/2014 | Geist et al. |
| 2014/0222142 A1* | 8/2014 | Kovalsky .............. A61F 2/2418 623/2.17 |
| 2015/0142100 A1* | 5/2015 | Morriss .................. A61F 2/246 623/2.4 |
| 2017/0216026 A1* | 8/2017 | Quill ..................... A61F 2/2427 |
| 2017/0266003 A1* | 9/2017 | Hammer ............... A61F 2/2418 |

FOREIGN PATENT DOCUMENTS

| | | |
|---|---|---|
| WO | WO 2005/027797 | 3/2005 |
| WO | WO 2009/132187 | 10/2009 |
| WO | WO 2010/106438 | 9/2010 |
| WO | WO 2011/069048 | 6/2011 |
| WO | WO 2011/106544 | 9/2011 |
| WO | WO 2011/137531 | 11/2011 |
| WO | WO 2013/076724 | 5/2013 |
| WO | WO 2014/181336 | 11/2014 |
| WO | WO 2016/114719 | 7/2016 |
| WO | WO 2018/131042 | 7/2018 |
| WO | WO 2018/131043 | 7/2018 |

OTHER PUBLICATIONS

International Preliminary Report on Patentability dated Jul. 25, 2019 From the International Bureau of WIPO Re. Application No. PCT/IL2018/050050. (8 Pages).
International Search Report and the Written Opinion dated Apr. 6, 2018 From the International Searching Authority Re. Application No. PCT/IL2018/050050. (14 Pages).
International Search Report and the Written Opinion dated May 23, 2018 From the International Searching Authority Re. Application No. PCT/IL2018/050049. (19 Pages).
Invitation to Pay Additional Fees, Communication Relating to the Results of the Partial International Search and the Provisional Opinion dated Mar. 23, 2018 From the International Searching Authority Re. Application No. PCT/IL2018/050049. (11 Pages).
Translation dated Jun. 22, 2021 of Notification of Office Action dated May 31, 2021 From the China National Intellectual Property Administration Re. Application No. 201880000493.5. (7 Pages).

* cited by examiner

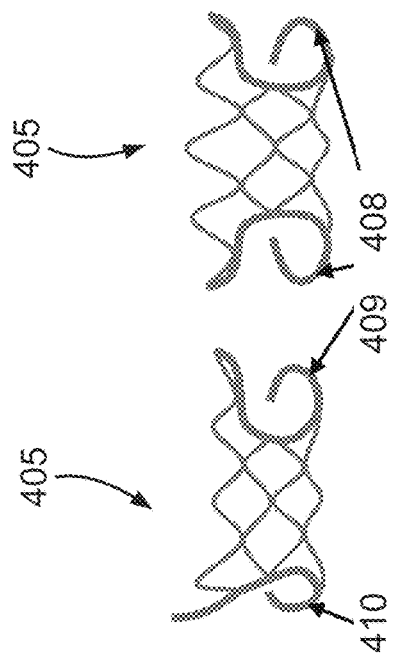
FIGURE 4B
FIGURE 4C
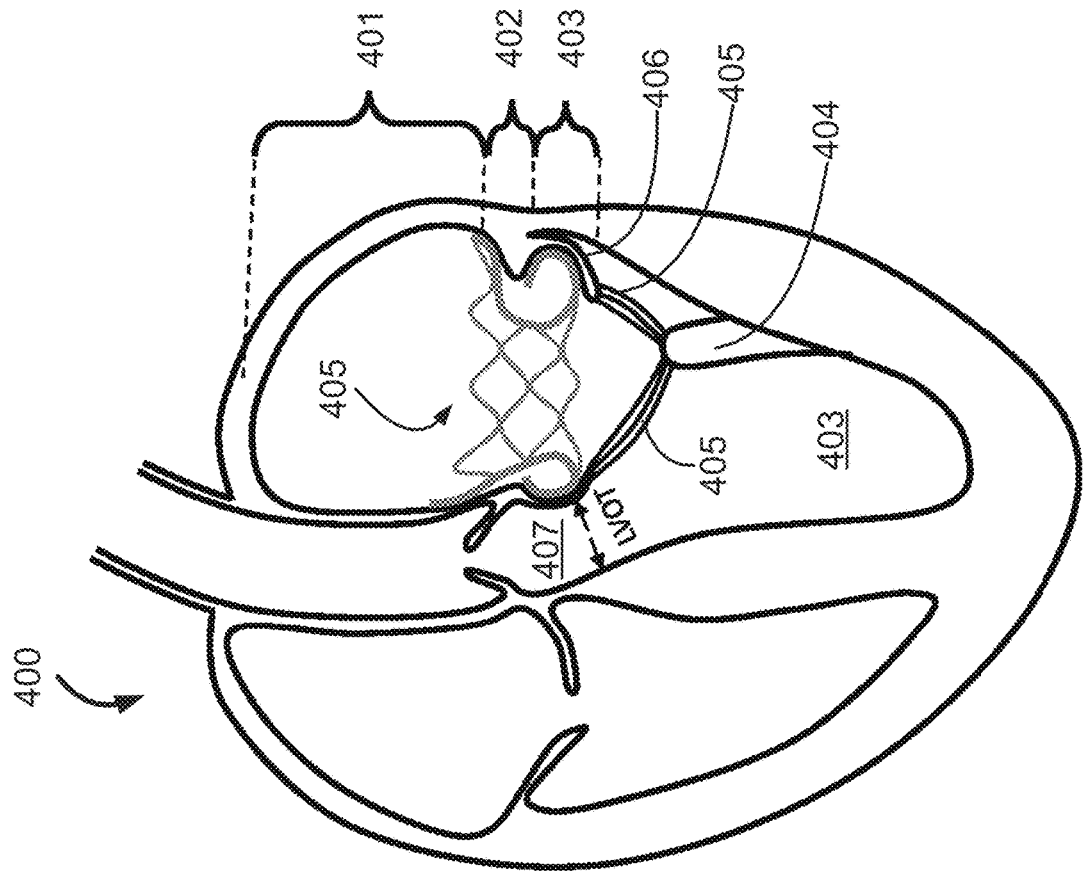
FIGURE 4A

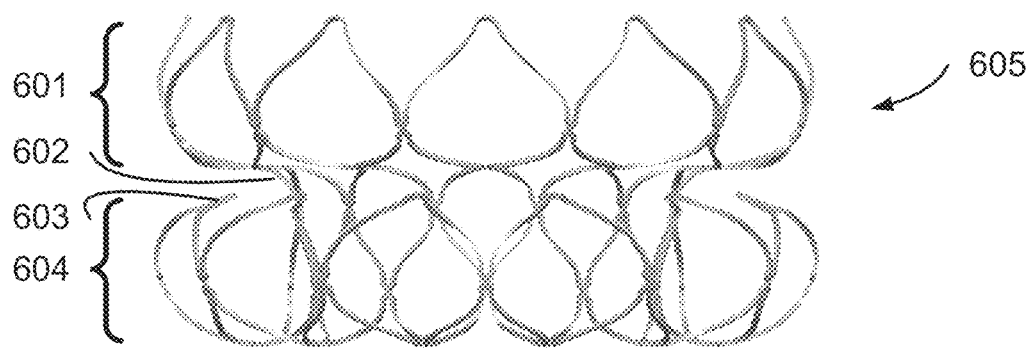
FIGURE 6A
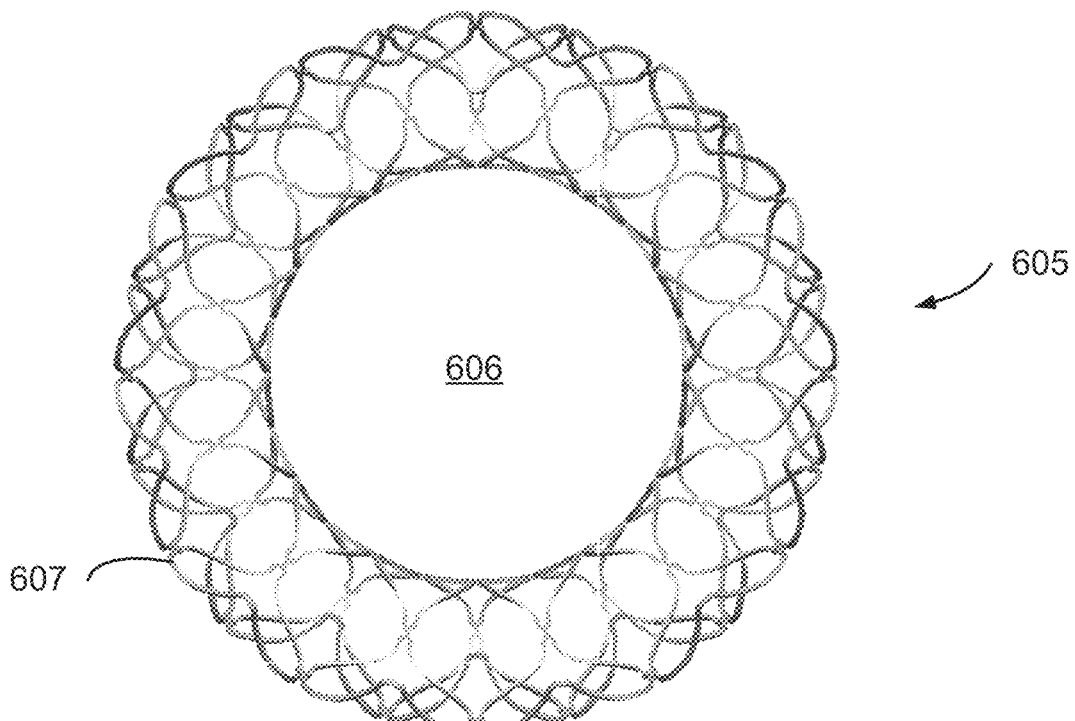
FIGURE 6B
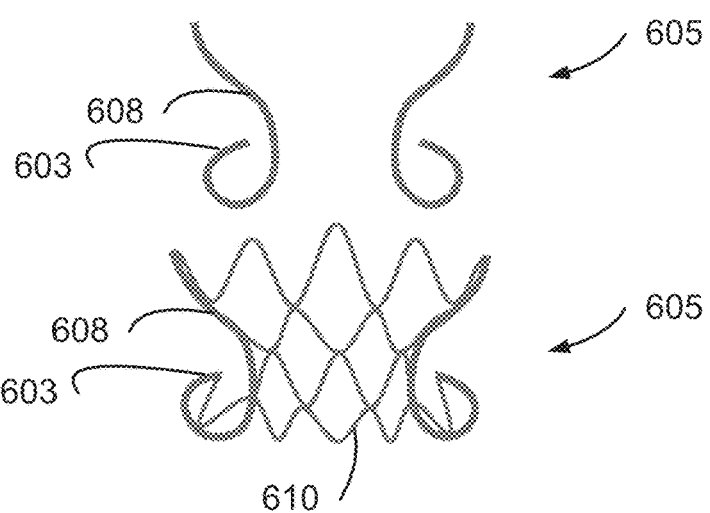
FIGURE 6C
FIGURE 6D

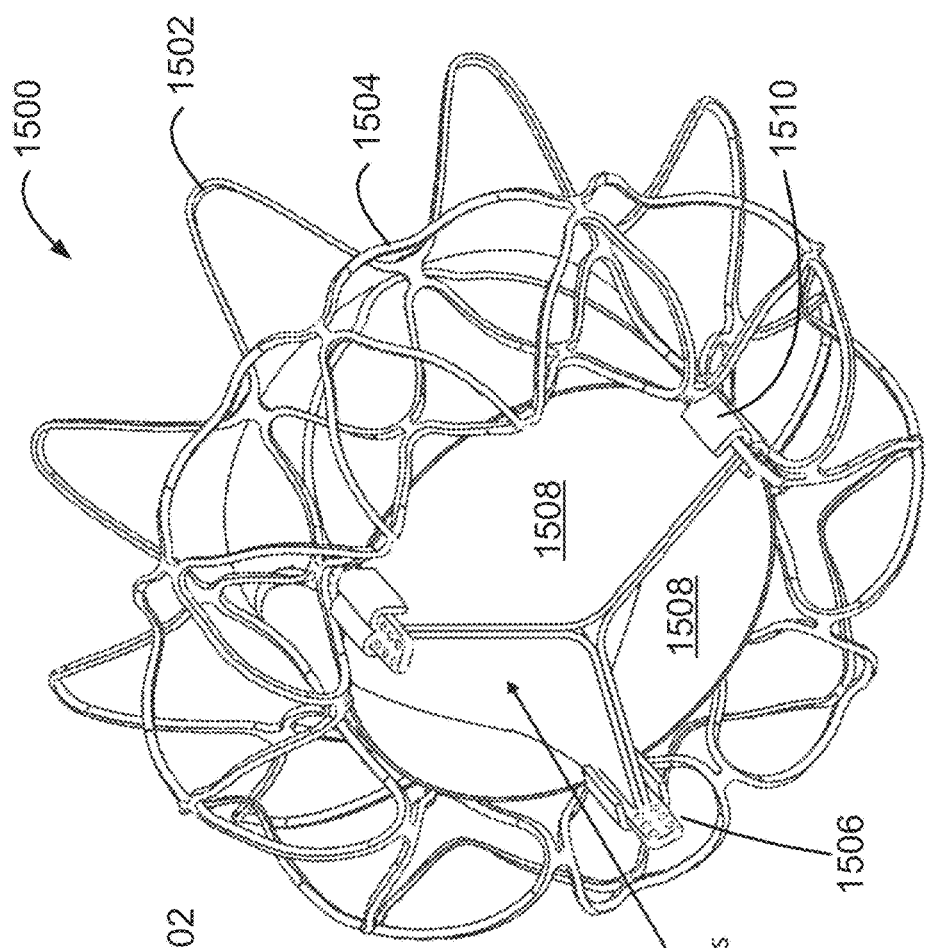
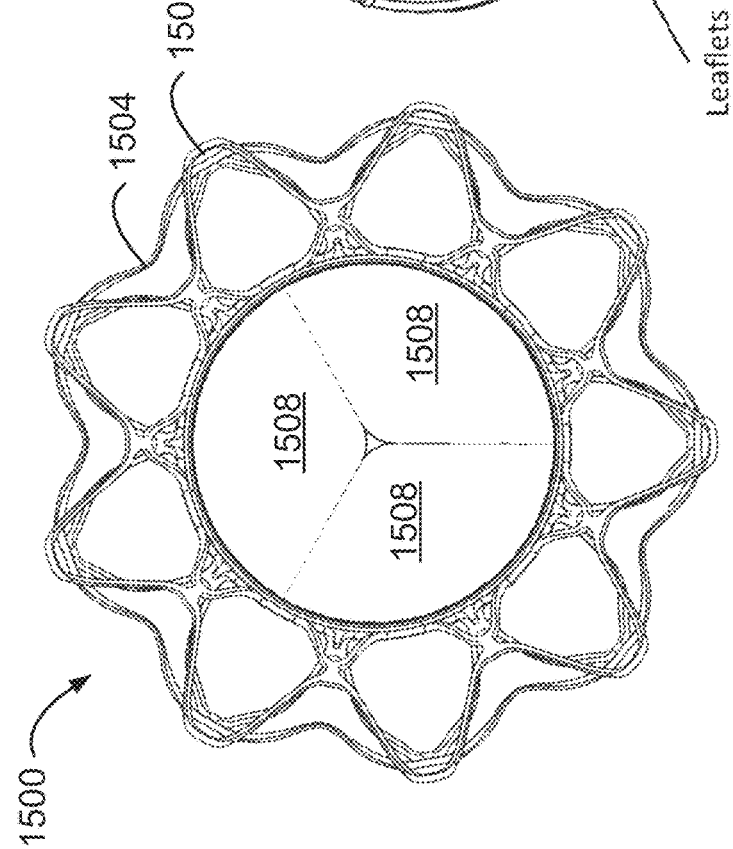
FIGURE 15B
FIGURE 15A

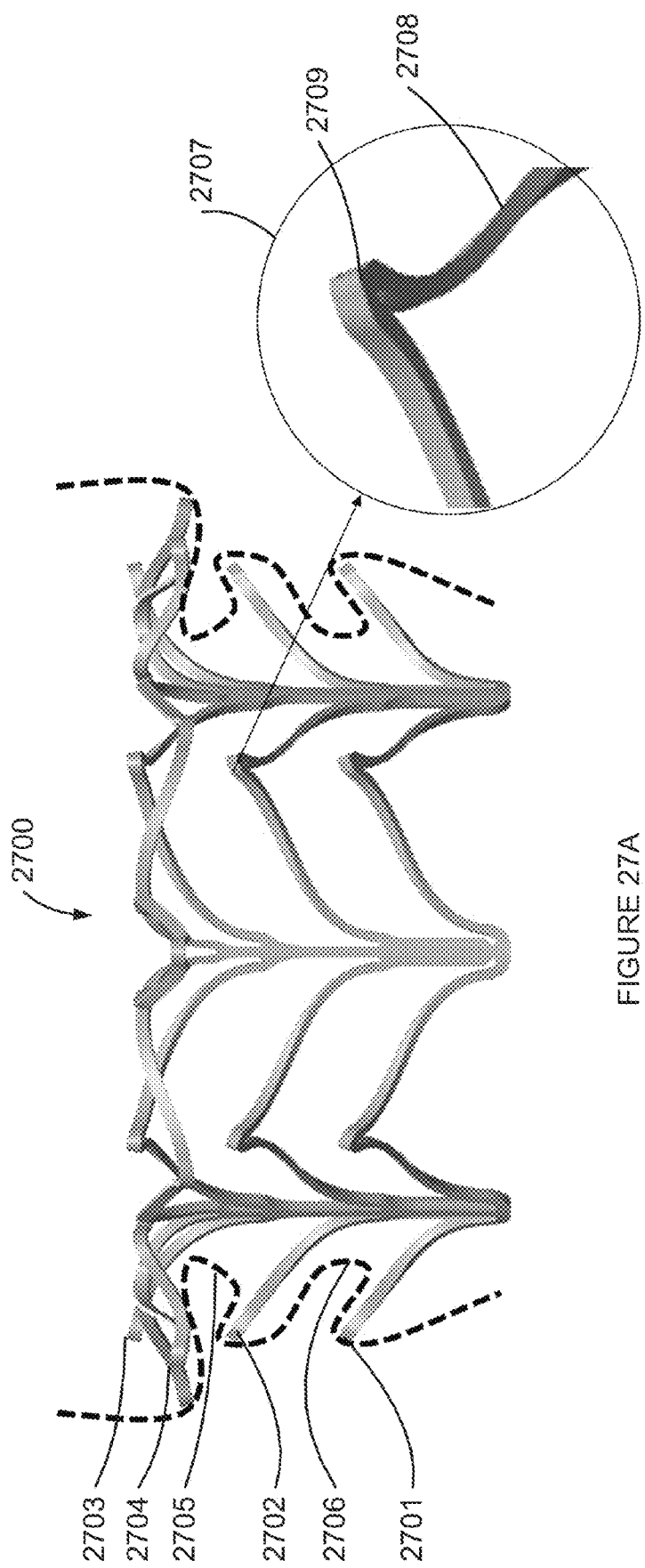
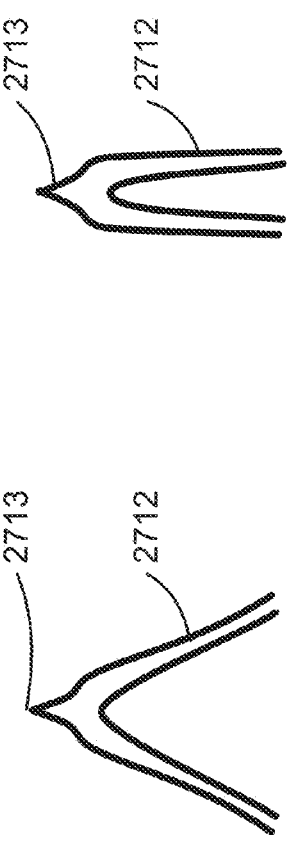
FIGURE 27A
FIGURE 27B
FIGURE 27C

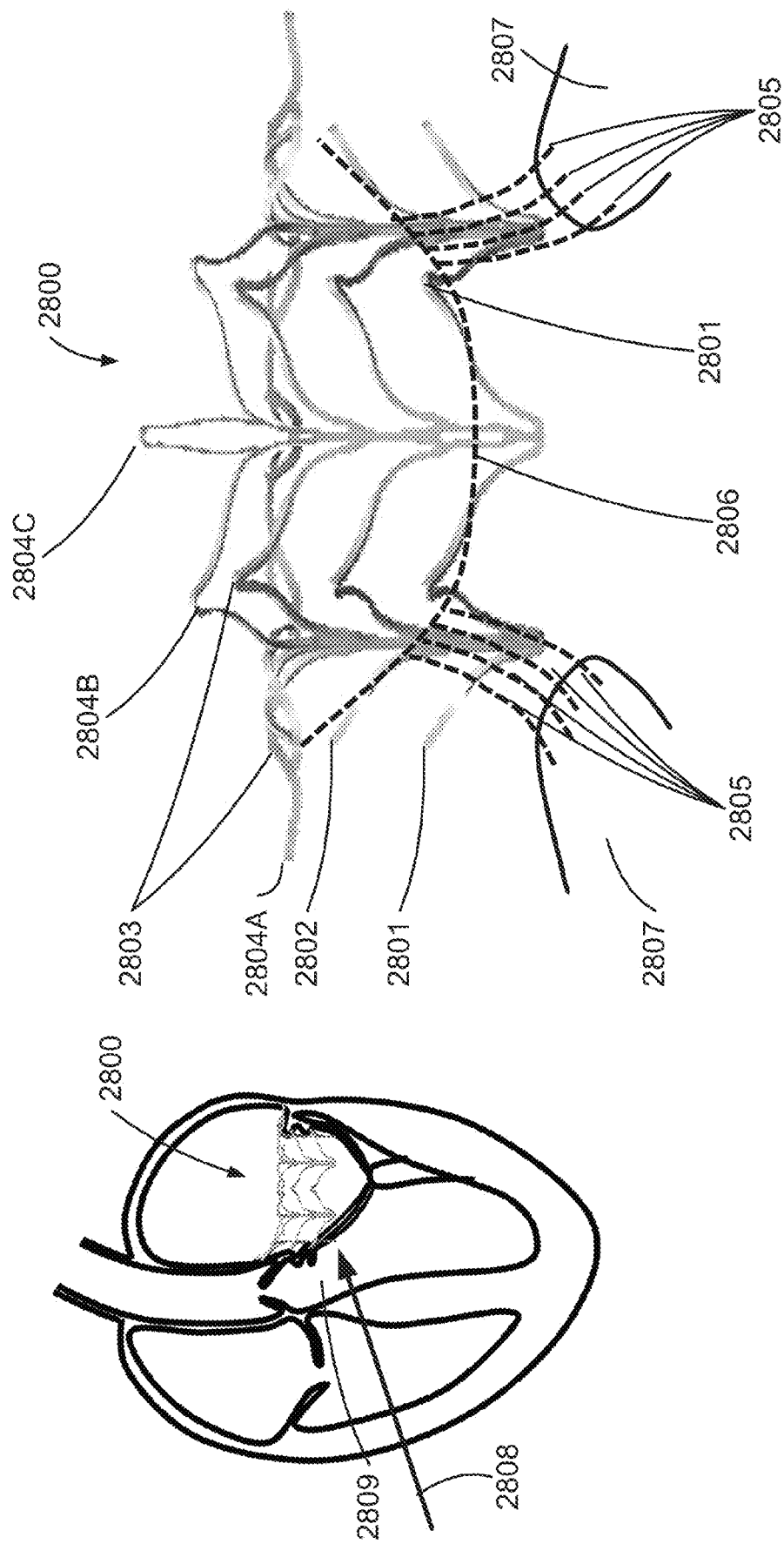

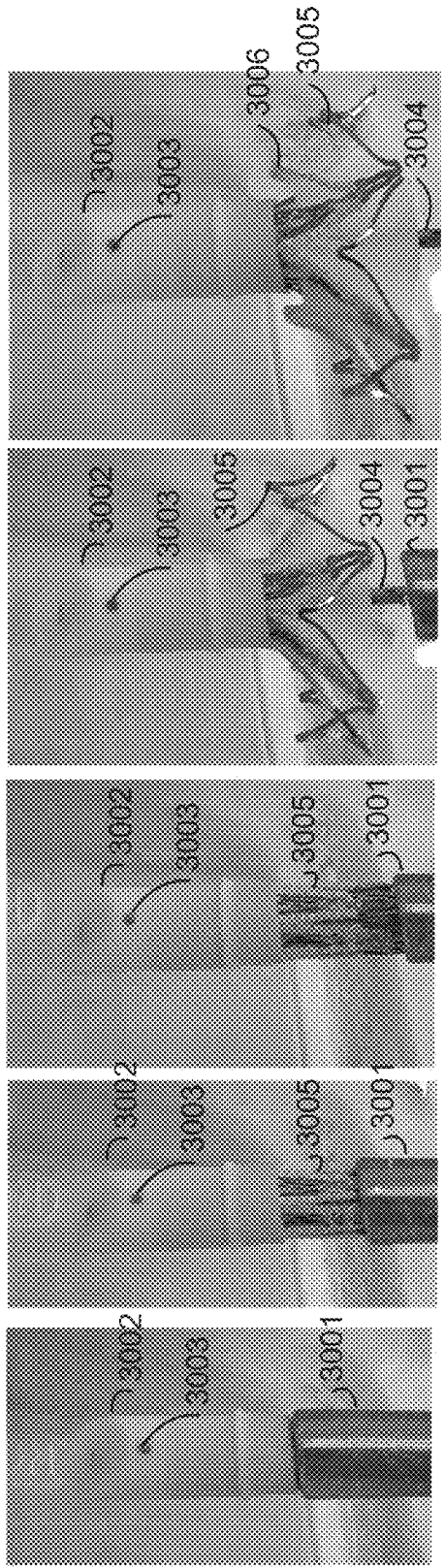
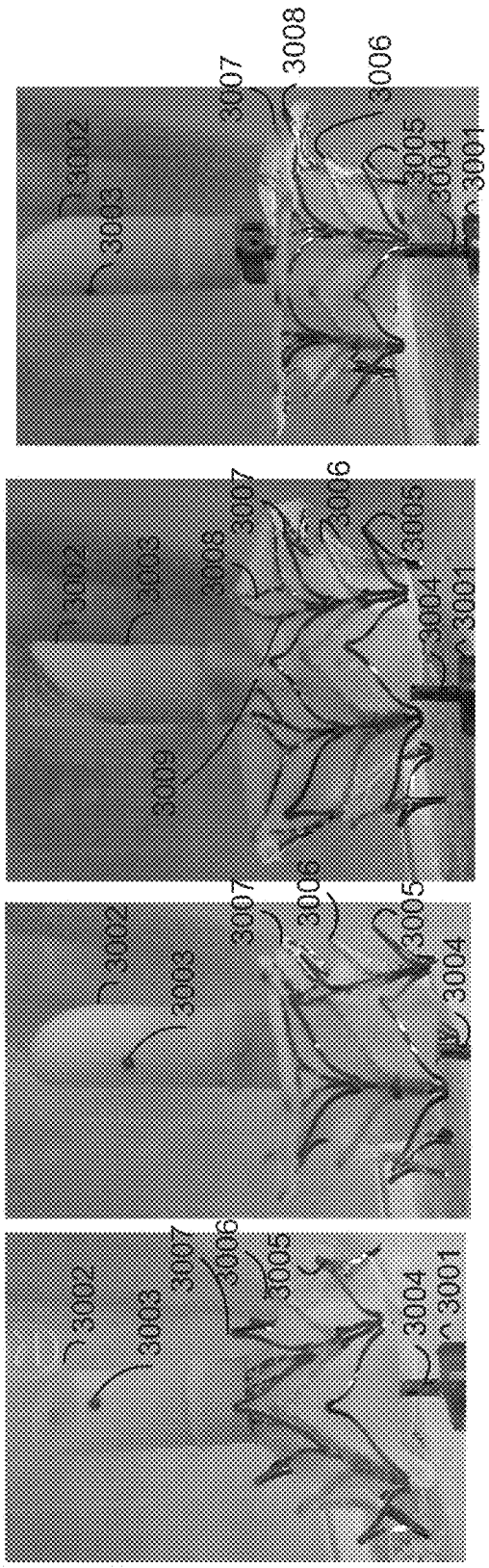
FIGURE 30A FIGURE 30B FIGURE 30C FIGURE 30D FIGURE 30E
FIGURE 30F FIGURE 30G FIGURE 30H FIGURE 30I

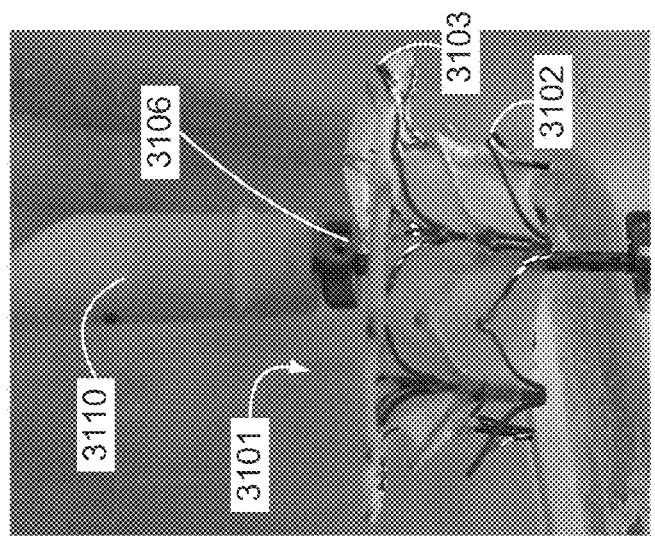
FIGURE 31C
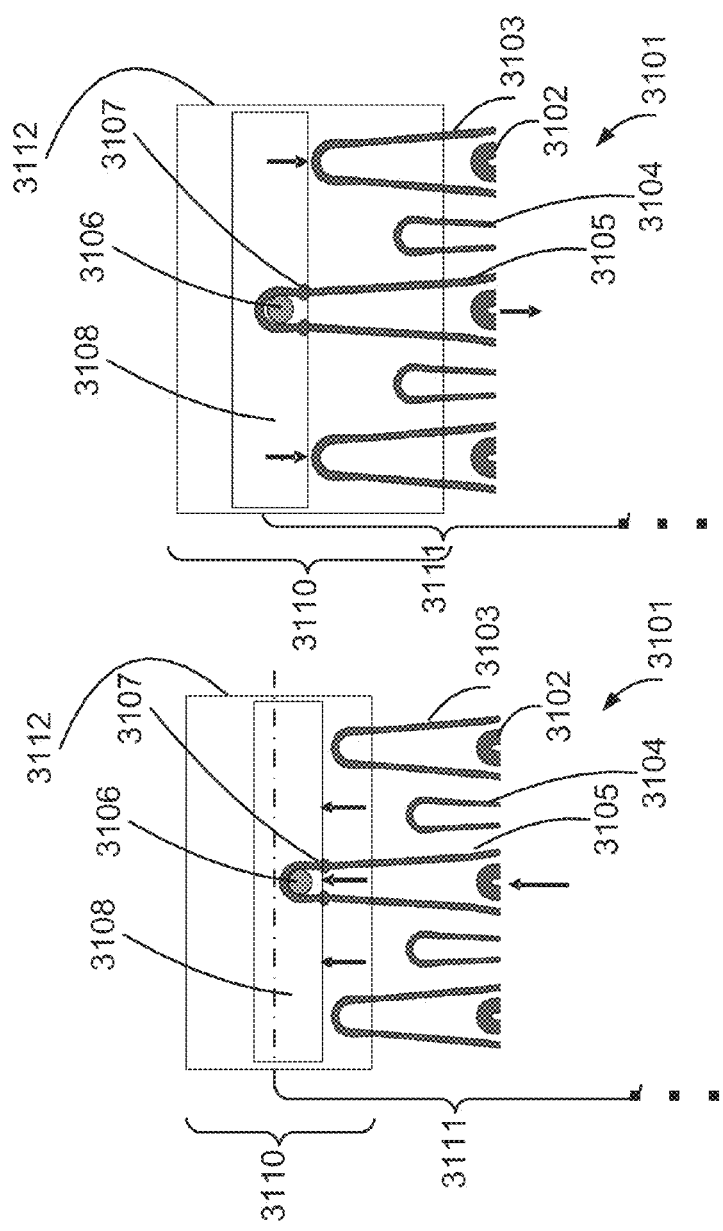
FIGURE 31B
FIGURE 31A

MULTI-LEVEL CARDIAC IMPLANT

RELATED APPLICATION'S

This application is a National Phase of PCT Patent Application No. PCT/IL2018/050050 having International filing date of Jan. 11, 2018, which claims the benefit of priority under 35 USC § 119(e) of U.S. Provisional Patent Application No. 62/444,835 filed on Jan. 11, 2017. The contents of the above Applications are all incorporated herein by reference in their entirety.

FIELD AND BACKGROUND OF THE INVENTION

The present invention, in some embodiments thereof, relates to a cardiac valve prosthesis, and more particularly, but not exclusively, to a cardiac valve prosthesis for a mitral valve.

The mitral valve and tricuspid valve are unidirectional heart valves which separate the left and right atria respectively, from corresponding heart ventricles. These valves have a distinct anatomical and physiological structure, having two (mitral) or three (tricuspid) sail-like leaflets connected to a sub-valvular mechanism of strings (chordae tendinae) and papillary muscles forming a part of the heart's ventricular shape, function and size.

The heart has four chambers: the right and left atria, and the right and left ventricles. The atria receive blood and then pump it into the ventricles, which then pump it out into the body.

Synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves which are supposed to ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, intra-ventricular pressure rises above the pressure in the atrium and pushes the mitral valve shut.

As noted above, these valves feature a plurality of leaflets connected to chordae tendinae and papillary muscles, which allow the leaflets to resist the high pressure developed during contractions (pumping) of the left and right ventricles. In a healthy heart, the chordae become taut, preventing the leaflets from being forced into the left or right atria and inverted. Prolapse is a term used to describe a condition wherein coaptation edges of each leaflet initially may coapt and close, but then the leaflets rise higher, the edges separate, and the valve leaks. This is normally prevented by a contraction of the papillary muscles and by the normal length of the chordae. Contraction of the papillary muscles is usually simultaneous with the contraction of the ventricle and serves to keep healthy valve leaflets tightly shut at peak contraction pressures exerted by the ventricle.

Valve malfunction can result from the chordae becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

Diseases of the valves can cause either narrowing (stenosis) or dilatation (regurgitation, insufficiency) of the valve, or a combination of those. Surgical treatment for repair or replacement of the valves typically includes an open-heart procedure, extracorporeal circulation and, if replaced, a complete or partial resection of the diseased valve.

The disclosures of all references mentioned above and throughout the present specification, as well as the disclosures of all references mentioned in those references, are hereby incorporated herein by reference.

SUMMARY OF THE INVENTION

An aspect of some embodiments of the invention involves a frame shaped so that the frame crimps, or pinches, natural cardiac valve leaflets, or the natural heart valve annulus.

An aspect of some embodiments of the invention involves a frame designed to pass through a catheter as a lumen or tube a single wall, and when released from the catheter, to expand and have a portion of the frame expand so that at least some of the frame becomes a double layered lumen.

According to an aspect of some embodiments of the present invention there is provided a heart valve prosthesis including a frame, the frame including a plurality of supports designed to extend from an upstream side of a natural heart valve to a downstream side of the natural heart valve, and a plurality of wires attached to the plurality of supports, wherein the plurality of wires are arranged as arcs connecting the supports, the arcs having two ends, each end attached to one of the supports, and a peak pointing from a center of the frame circumferentially outward and toward the upstream side of the frame, and the plurality of wires are arranged as at least two rings, each ring circumnavigating the center lumen of the frame.

The term "wire" in all its grammatical forms is used in the present application and claims to mean a connector or a connecting element, regardless of cross section or method of manufacture. The connecting element may have a round or a rectangular cross section or other cross section. The connecting element may be produced, by way of some non-limiting examples, as a wire and/or by laser cutting a sheet to a form of struts and connectors.

The term "arc" in all its grammatical forms is used in the present application and claims to mean a bridge shape such as an arch, a V shape, and inverted V shape or a double arch.

According to some embodiments of the invention, a top of an arc of the wire arcs points away from a center axis of the frame. According to some embodiments of the invention, a top of an arc of the wire arcs points upstream.

According to some embodiments of the invention, the arcs have a shape which includes a tip designed for the wire arcs to bend when the frame is compressed into a catheter.

According to some embodiments of the invention, the rings are spaced apart at least 2 millimeters, allowing leaflets of the natural heart valve to be caught between the wires. According to some embodiments of the invention, the rings are spaced apart in a range of 2 millimeters to 8 millimeters.

According to some embodiments of the invention, a number of wire arcs per rings is a multiple of three. According to some embodiments of the invention, a number of wire arcs per ring is a selected from a group consisting of a wire arc count of three, six, and nine.

According to some embodiments of the invention, the plurality of supports includes a number of supports which is a multiple of three. According to some embodiments of the invention, the plurality of supports includes a number of supports selected from a group consisting of a support count of three, six, and nine.

According to some embodiments of the invention, the frame includes an inner lumen from an upstream portion of the frame to a downstream portion of the frame, and a cross section of the lumen is a multi-pointed shape.

According to some embodiments of the invention, the multi-pointed shape of the inner lumen includes a number of points which is a multiple of three.

According to some embodiments of the invention, further including a plurality of flexible sheet leaflets attached to the frame, the plurality of leaflets arranged as a one-directional valve opening to fluid pressure in a downstream direction and closing to fluid pressure in an upstream direction.

According to some embodiments of the invention, the plurality of leaflets includes a number of leaflets which is a multiple of three.

According to an aspect of some embodiments of the present invention there is provided a method for producing a heart valve prosthesis frame, the method including producing a plurality of supports designed to extend from an upstream side of a natural heart valve to a downstream side of the natural heart valve, and a plurality of wires attached to the plurality of supports, wherein the plurality of wires are arranged as arcs connecting the supports, the arcs having two ends, each end attached to one of the supports, and a peak pointing from a center of the frame circumferentially outward and toward an upstream side of the frame, and the plurality of wires are arranged as at least two rings, each ring circumnavigating the center lumen of the frame.

According to some embodiments of the invention, a top of an arc of the wires is produced to point away from a center axis of the frame. According to some embodiments of the invention, a top of an arc of the wires is produced to point upstream.

According to some embodiments of the invention, the rings are spaced apart at least 2 millimeters, designed so that leaflets of the natural heart valve may be caught between the wires.

According to some embodiments of the invention, the frame includes at least three rings, designed so that leaflets of the natural heart valve to be caught between the wires at at least two levels along the leaflets of the natural heart.

According to some embodiments of the invention, the rings are spaced apart in a range of 2 millimeters to 8 millimeters.

According to some embodiments of the invention, a number of wire arcs per ring is a multiple of three. According to some embodiments of the invention, a number of wire arcs per ring includes a number selected from a group consisting of a wire arc count of three, six, and nine.

According to some embodiments of the invention, the plurality of supports includes a number of supports which is a multiple of three. According to some embodiments of the invention, the plurality of supports includes a number of supports selected from a group consisting of a support count of three, six, and nine.

According to some embodiments of the invention, further including suturing a plurality of flexible sheets to the frame, the plurality of sheets arranged as a one-directional valve opening to fluid pressure in a downstream direction and closing to fluid pressure in an upstream direction.

According to some embodiments of the invention, the plurality of sheets includes a number of leaflets which is a multiple of three.

According to an aspect of some embodiments of the present invention there is provided a method of anchoring a prosthetic heart valve, including providing a heart valve prosthetic frame including a plurality of supports designed to extend from an upstream side of a natural heart valve to a downstream side of the natural heart valve, and a plurality of wires attached to the plurality of supports, wherein at least two of the plurality of wires are arranged as arcs connecting the supports, the arcs having two ends, each end attached to one of the supports, and a peak pointing from a center of the frame circumferentially outward, and the plurality of wires are arranged as at least two rings, each ring circumnavigating the center lumen of the frame, inserting the heart valve prosthetic frame into an annulus of a natural heart valve, expanding the heart valve prosthetic frame, allowing a natural heart valve leaflet to protrude between the at least two wires, and using at least one of the plurality of wires to anchor the frame against the natural heart valve leaflet.

According to some embodiments of the invention, further including clamping the natural heart valve leaflet between at least one of the wires and an upper portion of the frame.

According to some embodiments of the invention, further including clamping the natural heart valve leaflet between at least two of the wires.

According to some embodiments of the invention, further including trapping the annulus of the natural heart valve between at least one of the wires and an upper portion of the frame.

According to some embodiments of the invention, the frame includes at least three rings, the allowing a natural heart valve leaflet to protrude between the at least two wires includes allowing the natural heart valve leaflet to protrude between at least three wires at at least two levels along the natural heart valve leaflets, and using the at least three wires to anchor the frame against the natural heart valve leaflet.

According to an aspect of some embodiments of the present invention there is provided a heart valve prosthesis including a frame, the frame including a plurality of supports designed to extend from an upstream side of a natural heart valve to a downstream side of the natural heart valve, and a plurality of wires attached between the plurality of supports, wherein a top portion of the frame is designed to expand wider than a natural heart valve annulus, a bottom portion of the frame is designed to expand wider than a natural heart valve annulus, and the bottom portion is designed to expand to a torus shape, pushing against the natural heart sides thereby providing a seal against blood flowing around the frame.

According to an aspect of some embodiments of the present invention there is provided a heart valve prosthesis frame, the frame including a hollow tube shape for allowing blood to flow through, an upstream portion designed to expand to have at least one dimension wider than a native heart valve annulus, a downstream portion attached to the upstream portion, the downstream portion also designed to expand to have at least a portion with at least one dimension wider than the native heart valve annulus, wherein the downstream portion is shaped to have one side of the downstream portion of the hollow tube frame extend less from a center of the hollow tube than an opposite side of the hollow tube.

According to some embodiments of the invention, further including the upstream portion shaped to have one side of the upstream portion of the hollow tube frame extend less from the center of the hollow tube than an opposite side of the hollow tube.

According to some embodiments of the invention, the downstream portion and the upstream portion have a same side of the hollow tube extend less from the center of the hollow tube than the opposite side of the hollow tube.

According to an aspect of some embodiments of the present invention there is provided a method for producing a heart valve prosthesis frame, the method including producing a frame including a hollow tube shape for allowing blood to flow through, an upstream portion of the hollow tube designed to expand to have at least one dimension wider than a native heart valve annulus, a downstream portion of the hollow tube attached to the upstream portion, the downstream portion also designed to expand to have at least a portion with at least one dimension wider than the native heart valve annulus, wherein the downstream portion is shaped to have one side of the downstream portion of the hollow tube extend less from a center of the hollow tube than an opposite side of the hollow tube.

According to some embodiments of the invention, further including producing the upstream portion to be shaped to have one side of the upstream portion of the hollow tube frame extend less from the center of the hollow tube than an opposite side of the hollow tube.

According to some embodiments of the invention, the downstream portion and the upstream portion are produced to have a same side of the hollow tube extend less from the center of the hollow tube than the opposite side of the hollow tube.

According to an aspect of some embodiments of the present invention there is provided a heart valve prosthesis including a frame, the frame including a hollow tube shape made of a shape memory material, an upstream portion designed to expand to have at least one dimension wider than a native heart valve annulus, a center portion attached to the upstream portion, designed to expand no wider than a native heart valve annulus, and a downstream portion attached to the center portion, the downstream portion also designed to expand to have at least one dimension wider than the native heart valve annulus, and have protrusions away from a center axis of the frame which point upstream.

According to some embodiments of the invention, the frame, before expanding, is in a shape of tube having a single layered wall as measured from a center of the tube, and after expanding, at least a portion of a tube has a double layer as measured from a center of the tube.

According to some embodiments of the invention, the downstream portion is designed to expand to a shape which points upstream.

According to some embodiments of the invention, the frame, in a crimped state before expansion, has a diameter in a range between 8 and 9 millimeters.

According to some embodiments of the invention, the frame, before expansion, fits into a catheter of inside diameter of 24 French gauge.

According to some embodiments of the invention, the frame, before expansion, fits into a catheter of inside diameter in a range of 24-28 French gauge.

According to an aspect of some embodiments of the present invention there is provided a method for producing a heart valve prosthesis frame, the method including producing a hollow tube shape made of a shape memory material, an upstream portion designed to expand to have at least one dimension wider than a native heart valve annulus, a center portion attached to the upstream portion, designed to expand no wider than a native heart valve annulus, and a downstream portion attached to the center portion, the downstream portion also designed to expand to have at least one dimension wider than the native heart valve annulus, and have protrusions away from a center axis of the frame which point upstream.

According to some embodiments of the invention, further including inserting the frame into a catheter.

According to an aspect of some embodiments of the present invention there is provided a method for shaping a heart valve prosthesis frame, the method including receiving a heart valve prosthesis frame within a catheter, the heart valve prosthesis frame including a hollow tube shape made of a shape memory material, an upstream portion designed to expand to have at least one dimension wider than a native heart valve annulus, a center portion attached to the upstream portion, designed to expand no wider than a native heart valve annulus, and a downstream portion attached to the center portion, the downstream portion also designed to expand to have at least one dimension wider than the native heart valve annulus, and have protrusions away from a center axis of the frame which point upstream, and extruding the frame from the catheter.

According to an aspect of some embodiments of the present invention there is provided a heart valve prosthesis including a frame, the frame including a plurality of struts designed to extend from an upstream side of a natural heart valve to a downstream side of the natural heart valve, and a plurality of connectors attached to the plurality of struts, wherein the plurality of connectors are arranged as arcs connecting the struts, the arcs having two ends, each end attached to one of the struts, and a peak pointing from a center of the frame circumferentially outward and toward the upstream side of the frame, and the plurality of connectors are arranged as at least two rows, each row circumnavigating the center lumen of the frame.

According to some embodiments of the invention, a top of an arc of the connector arcs points away from a center axis of the frame.

According to some embodiments of the invention, further including an upstream portion including connectors designed to expand on an upstream side of the natural heart valve.

According to some embodiments of the invention, only some tops of arcs of the connector arcs points away from a center axis of the frame.

According to some embodiments of the invention, tops of arcs of a bottom row of connector arcs point away from a center axis of the frame.

According to some embodiments of the invention, tops of arcs of a row of connector arcs upstream of a bottom row of connector arcs do not point away from a center axis of the frame.

According to some embodiments of the invention, tops of an upstream row of connector arcs point parallel to a center axis of the frame and extend further upstream than the connectors of the upstream portion.

According to some embodiments of the invention, a top of an arc of the connector arcs points upstream.

According to some embodiments of the invention, the arcs have a shape which includes a tip designed for the connector arcs to bend when the frame is compressed into a catheter.

According to some embodiments of the invention, the rows are spaced apart at least 2 millimeters, allowing leaflets of the natural heart valve to be caught between the connectors.

According to some embodiments of the invention, the rows are spaced apart in a range of 2 millimeters to 8 millimeters.

According to some embodiments of the invention, a number of connector arcs per rows is a multiple of three.

According to some embodiments of the invention, a number of connector arcs per row is a selected from a group consisting of a connector arc count of three, six, and nine.

According to some embodiments of the invention, the plurality of struts includes a number of struts which is a multiple of three.

According to some embodiments of the invention, the plurality of struts includes a number of struts selected from a group consisting of a strut count of three, six, and nine.

According to some embodiments of the invention, the frame includes an inner lumen from an upstream portion of the frame to a downstream portion of the frame, and a cross section of the lumen is a multi-pointed shape.

According to some embodiments of the invention, the multi-pointed shape of the inner lumen includes a number of points which is a multiple of three.

According to some embodiments of the invention, further including a plurality of flexible sheet leaflets attached to the frame, the plurality of leaflets arranged as a one-directional valve opening to fluid pressure in a downstream direction and closing to fluid pressure in an upstream direction.

According to some embodiments of the invention, the struts include longitudinal slits.

According to some embodiments of the invention, the flexible sheets are sewn to the struts.

According to some embodiments of the invention, the flexible sheets are sewn to a top row of connector arcs.

According to some embodiments of the invention, a plurality of tops of arcs of the connector arcs are sharp.

According to some embodiments of the invention, tops of arcs of a bottom row of connector arcs are sharp.

According to some embodiments of the invention, the plurality of leaflets includes a number of leaflets which is a multiple of three.

According to an aspect of some embodiments of the present invention there is provided a method for producing a heart valve prosthesis frame, the method including producing a plurality of struts designed to extend from an upstream side of a natural heart valve to a downstream side of the natural heart valve, and a plurality of connectors attached to the plurality of struts, wherein the plurality of connectors are arranged as arcs connecting the struts, the arcs having two ends, each end attached to one of the struts, and a peak pointing from a center of the frame circumferentially outward and toward an upstream side of the frame, and the plurality of connectors are arranged as at least two rows, each row circumnavigating the center lumen of the frame.

According to some embodiments of the invention, a top of an arc of the connectors is produced to point away from a center axis of the frame.

According to some embodiments of the invention, a top of an arc of the connectors is produced to point upstream.

According to some embodiments of the invention, the rows are spaced apart at least 2 millimeters, designed so that leaflets of the natural heart valve may be caught between the connectors.

According to some embodiments of the invention, the frame includes at least three rows, designed so that leaflets of the natural heart valve to be caught between the connectors at at least two levels along the leaflets of the natural heart.

According to some embodiments of the invention, the rows are spaced apart in a range of 2 millimeters to 8 millimeters.

According to some embodiments of the invention, a number of connector arcs per row is a multiple of three.

According to some embodiments of the invention, a number of connector arcs per row includes a number selected from a group consisting of a connector arc count of three, six, and nine.

According to some embodiments of the invention, the plurality of struts includes a number of struts which is a multiple of three.

According to some embodiments of the invention, the plurality of struts includes a number of struts selected from a group consisting of a strut count of three, six, and nine.

According to some embodiments of the invention, further including suturing a plurality of flexible sheets to the frame, the plurality of sheets arranged as a one-directional valve opening to fluid pressure in a downstream direction and closing to fluid pressure in an upstream direction.

According to some embodiments of the invention, the plurality of sheets includes a number of leaflets which is a multiple of three.

According to an aspect of some embodiments of the present invention there is provided a method of anchoring a prosthetic heart valve, including providing a heart valve prosthetic frame including a plurality of struts designed to extend from an upstream side of a natural heart valve to a downstream side of the natural heart valve, and a plurality of connectors attached to the plurality of struts, wherein at least two of the plurality of connectors are arranged as arcs connecting the struts, the arcs having two ends, each end attached to one of the struts, and a peak pointing from a center of the frame circumferentially outward, and the plurality of connectors are arranged as at least two rows, each row circumnavigating the center lumen of the frame, inserting the heart valve prosthetic frame into an annulus of a natural heart valve, expanding the heart valve prosthetic frame, allowing a natural heart valve leaflet to protrude between the at least two connectors, and using at least one of the plurality of connectors to anchor the frame against the natural heart valve leaflet.

According to some embodiments of the invention, further including clamping the natural heart valve leaflet between at least one of the connectors and an upper portion of the frame.

According to some embodiments of the invention, further including clamping the natural heart valve leaflet between at least two of the connectors.

According to some embodiments of the invention, further including trapping the annulus of the natural heart valve between at least one of the connectors and an upper portion of the frame.

According to some embodiments of the invention, the frame includes at least three rows, the allowing a natural heart valve leaflet to protrude between the at least two connectors includes allowing the natural heart valve leaflet to protrude between at least three connectors at at least two levels along the natural heart valve leaflets, and using the at least three connectors to anchor the frame against the natural heart valve leaflet.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified line drawing of a cross section of a heart;

FIGS. 2A and 2B are simplified line drawing illustrations of a cross section of a heart and a heart valve prosthesis frame located in the natural mitral valve according to an example embodiment of the invention;

FIG. 3 is a set of simplified line drawing illustrations of a cross section of a heart valve prosthesis frame according to an example embodiment of the invention;

FIGS. 4A, 4B and 4C are simplified line drawing illustrations of a cross section of a heart and a heart valve prosthesis frame located in the natural mitral valve according to an example embodiment of the invention;

FIGS. 5A and 5B are simplified line drawing illustrations of a heart valve prosthesis frame according to an example embodiment of the invention;

FIGS. 6A, 6B, 6C and 6D are simplified line drawing illustrations of a heart valve prosthesis frame according to an example embodiment of the invention;

FIGS. 7A, 7B and 7C are simplified line drawing illustrations of a heart valve prosthesis frame according to an example embodiment of the invention;

FIG. 8 is a set of simplified line drawing illustrations of a cross section of a heart valve prosthesis frame according to an example embodiment of the invention;

FIG. 9 is a simplified horizontal cross section of a heart with specific lines showing lines of interest in a mitral valve according to an example embodiment of the invention;

FIGS. 10A, 10B, 10C and 10D are images of a heart valve prosthesis constructed according to an example embodiment of the invention;

FIG. 11 is a simplified line drawing of a top view of a heart valve prosthesis constructed according to an example embodiment of the invention;

Figure 2B:
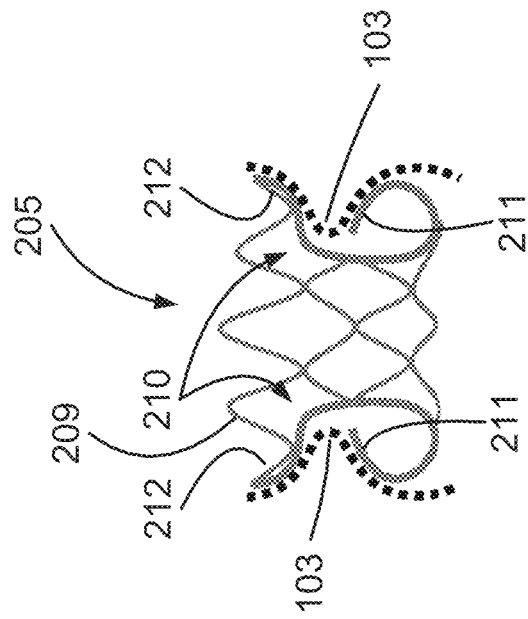
Figure 12A:
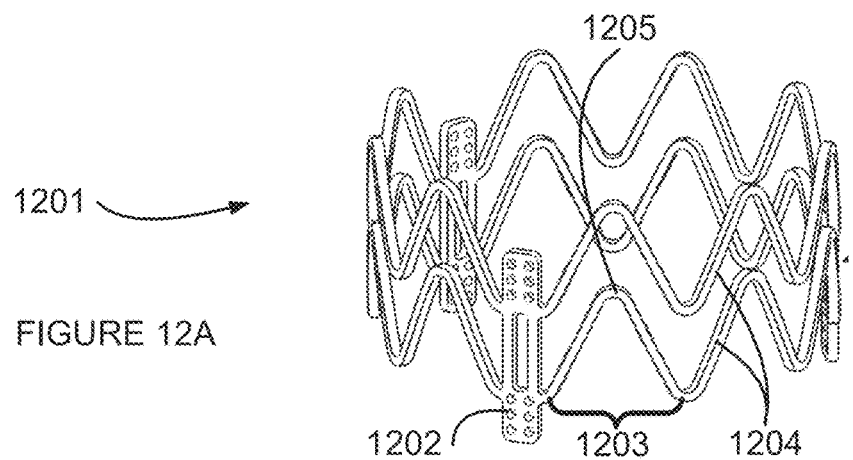
Figure 12B:
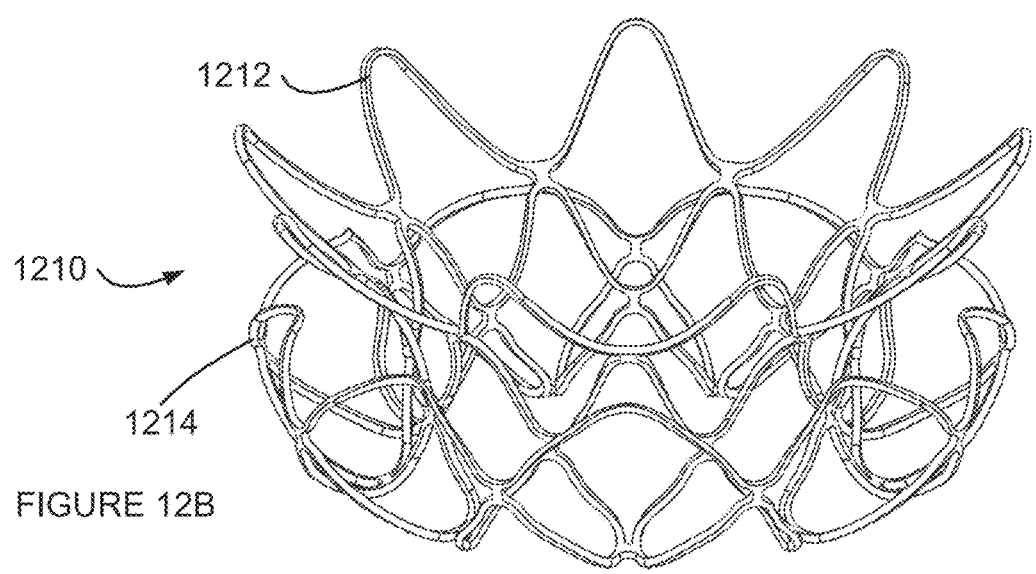
Figure 12C:
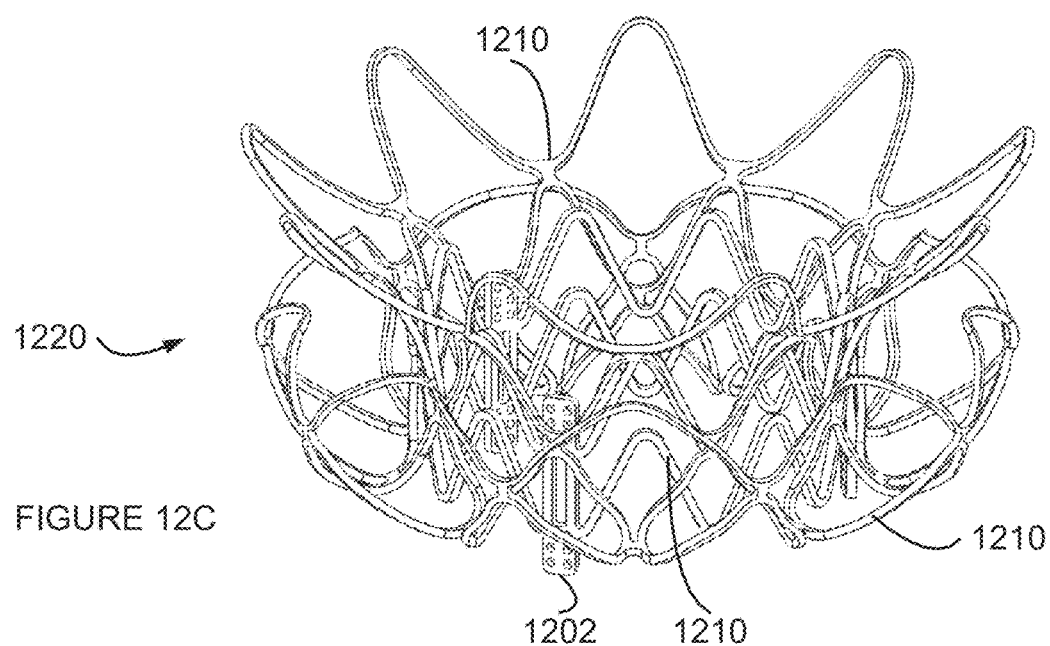
Figure 14A:
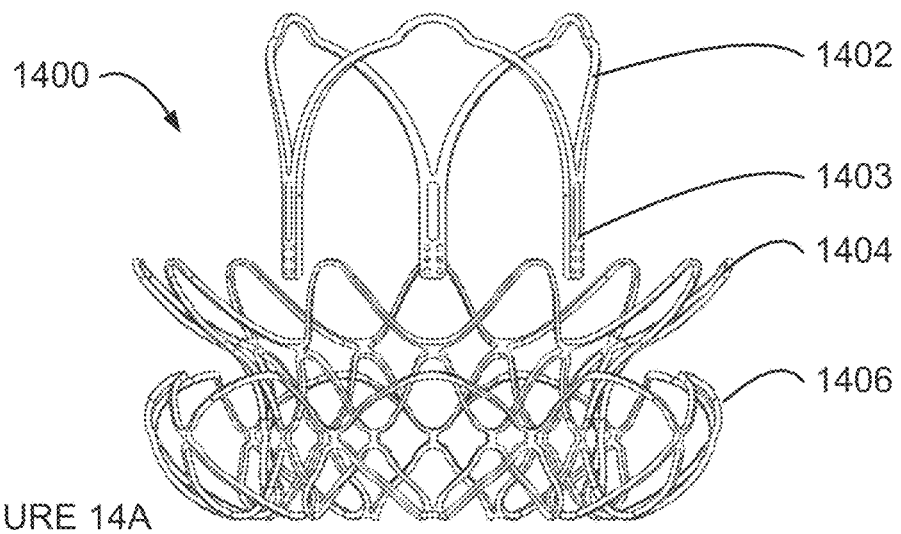
Figure 14B:
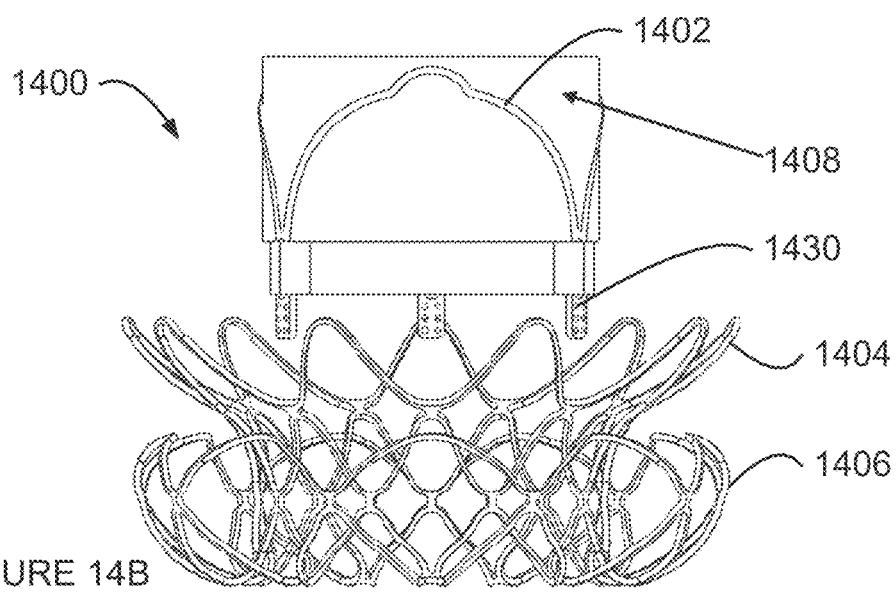
Figure 14C:
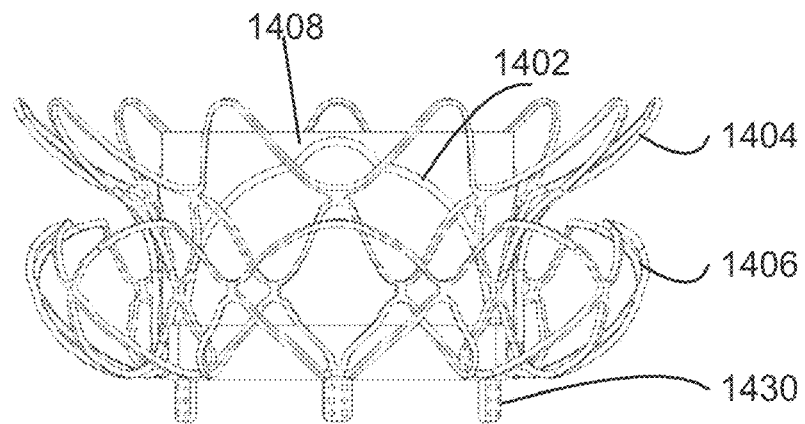
Figure 19B:
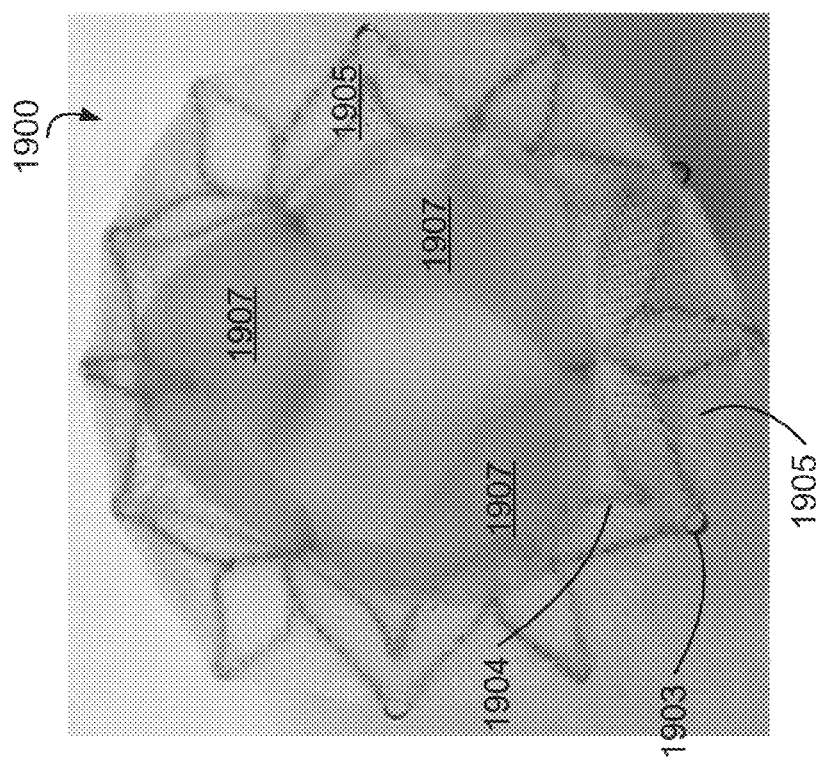
Figure 19A:
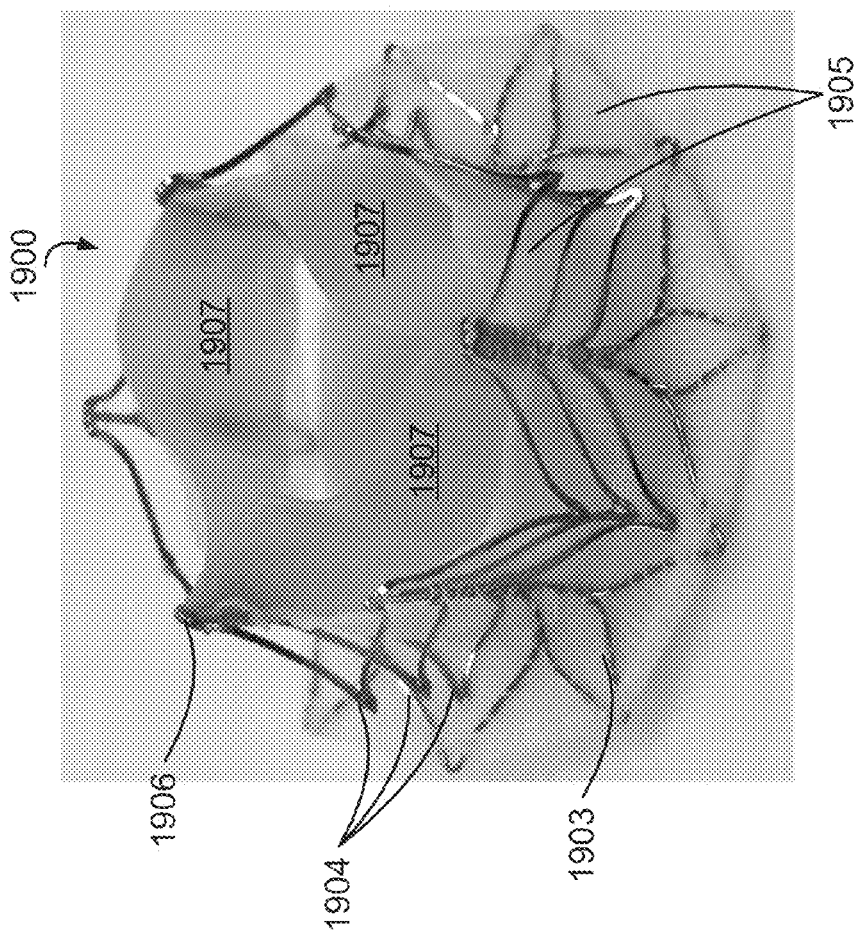
Figure 20A:
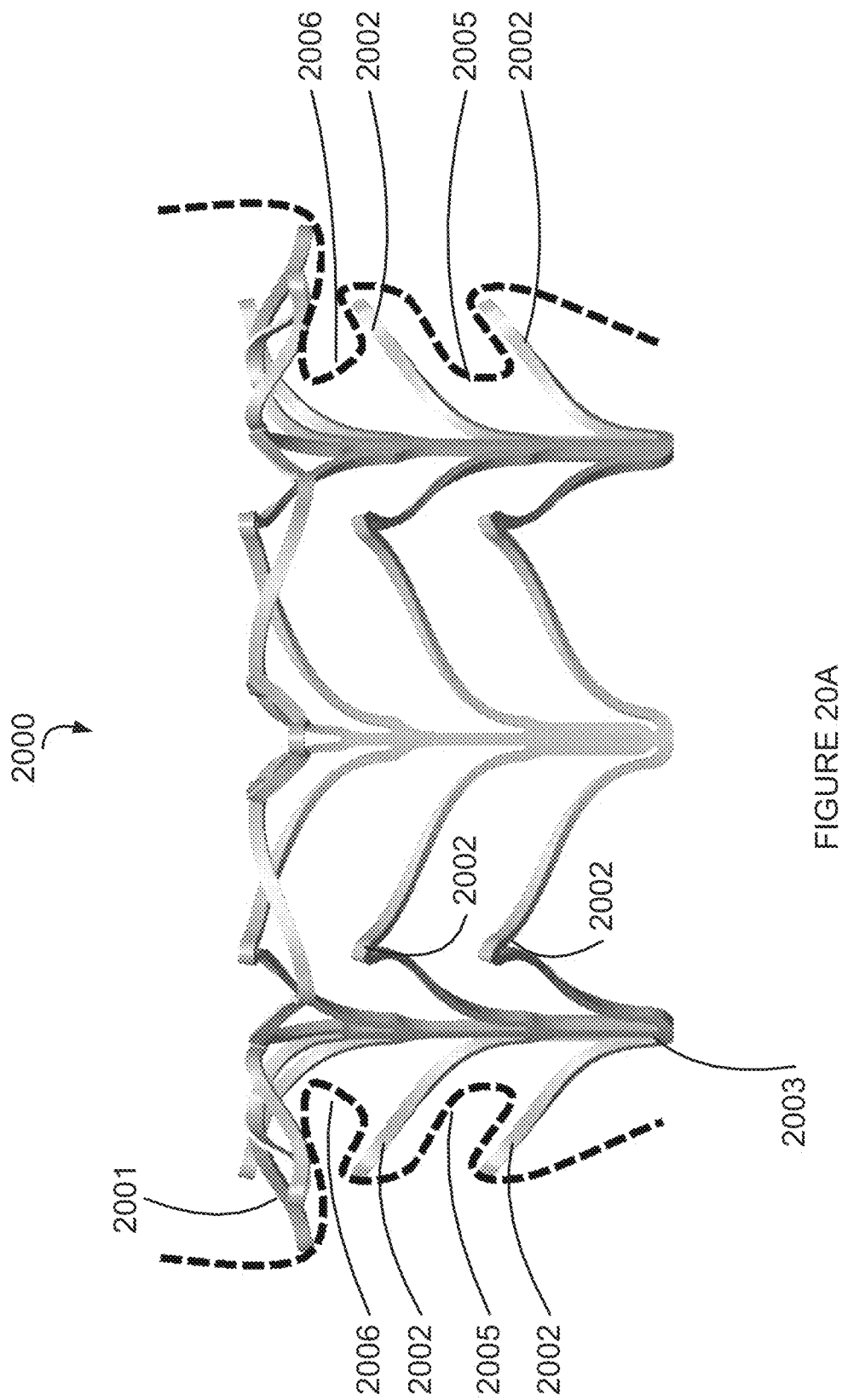
Figure 20B:
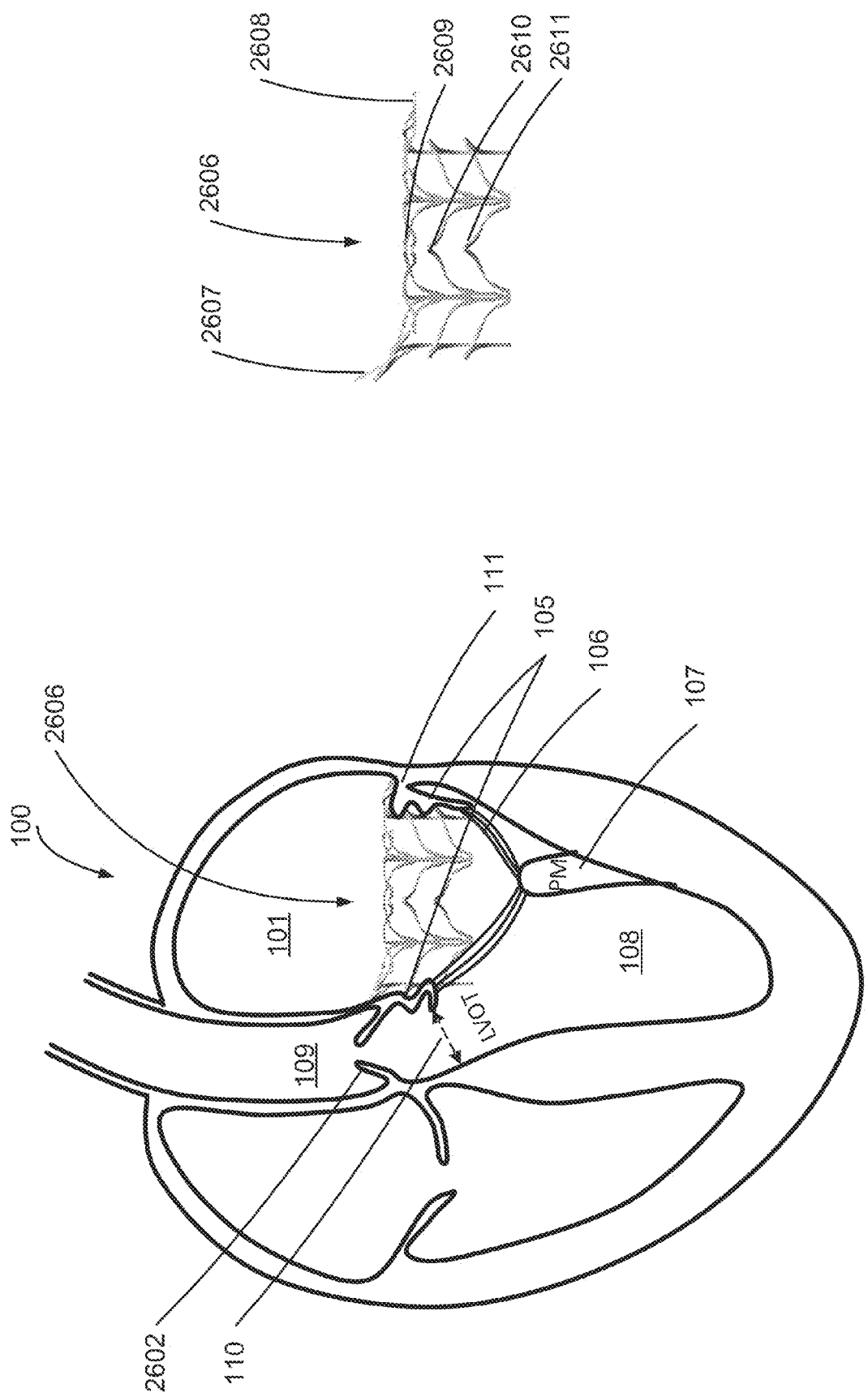
Figure 20D:
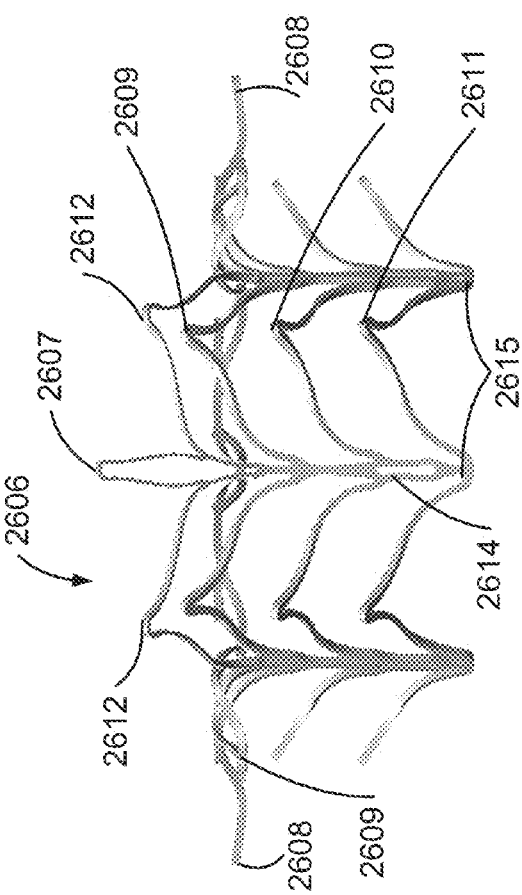
Figure 20C:
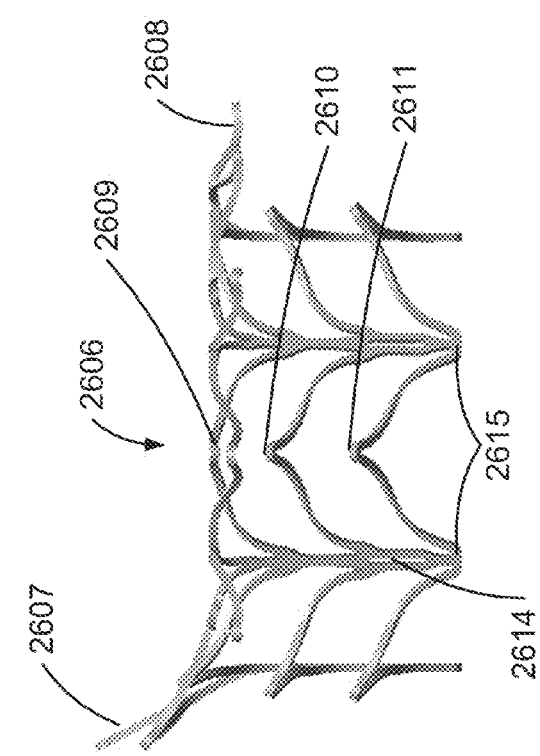
Figure 20F:
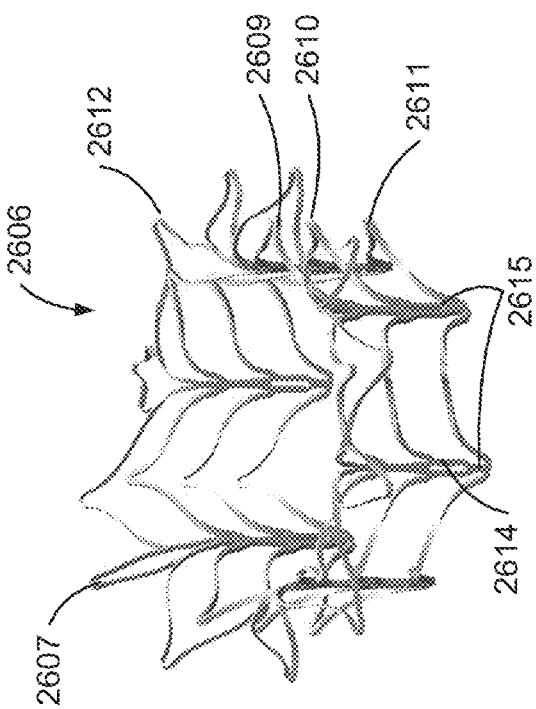
Figure 20E:
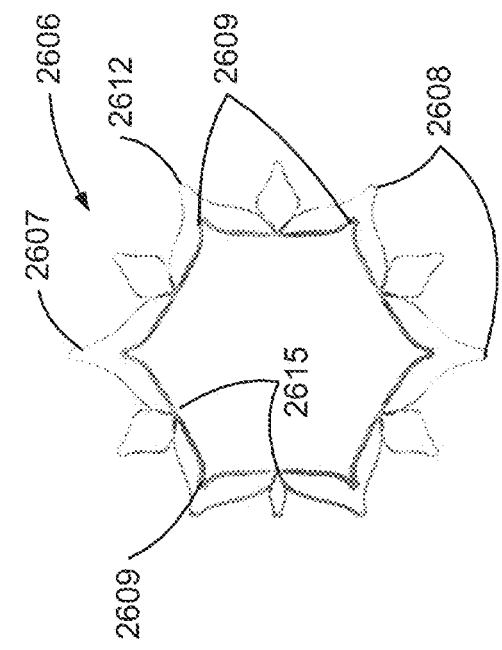
Figure 20G:
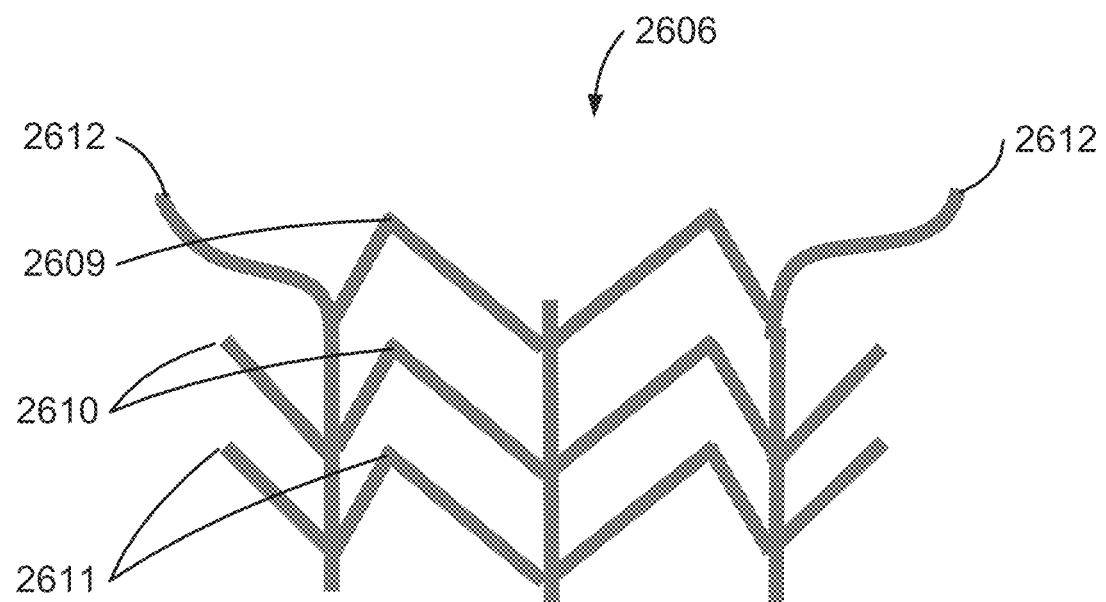
Figure 20H:
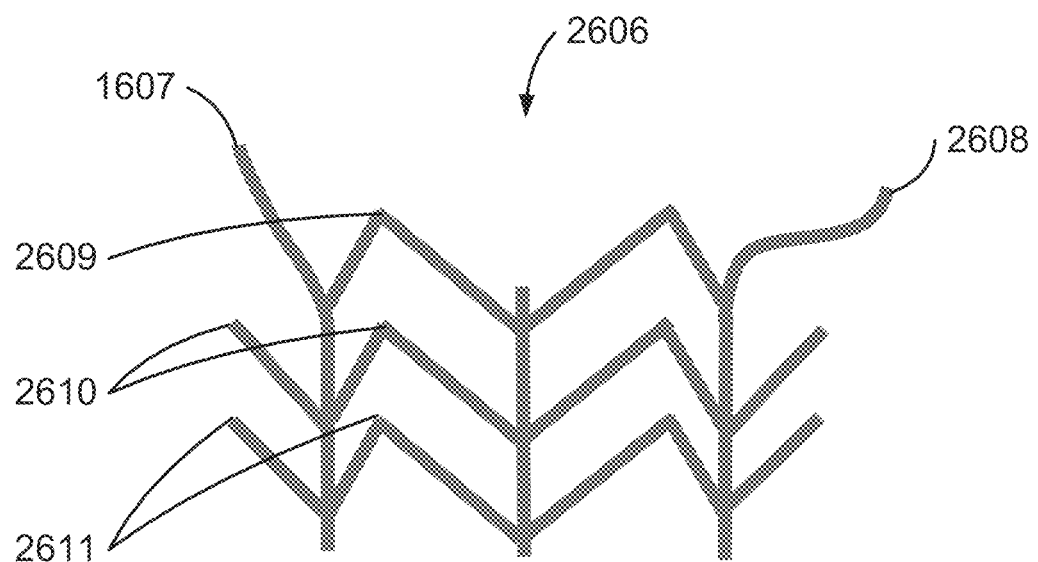
Figure 20I:
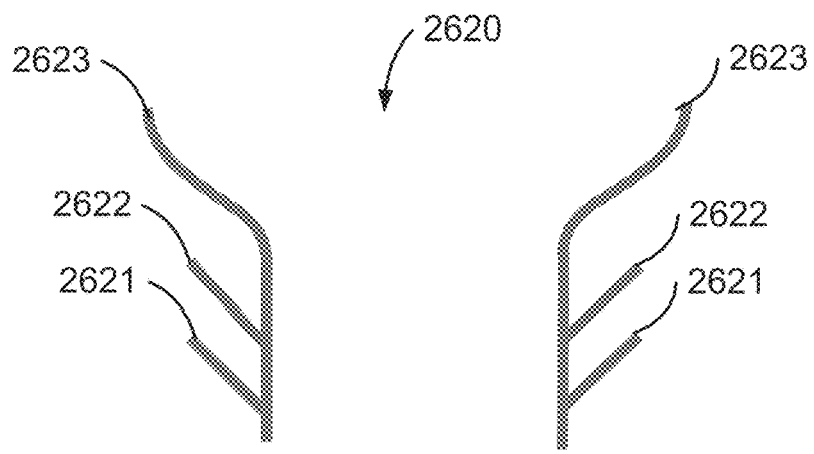
Figure 20J:
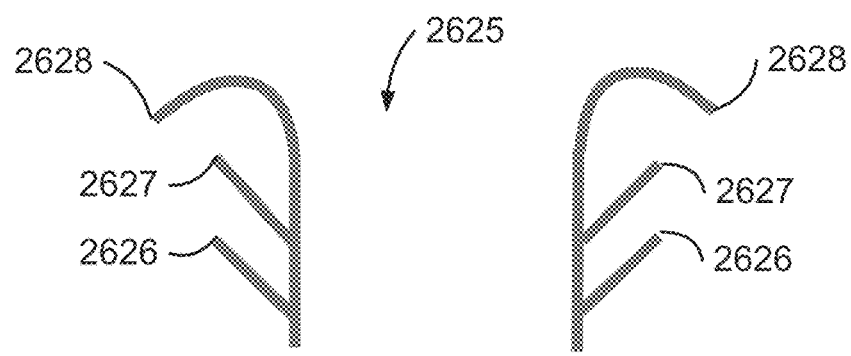
Figure 20K:
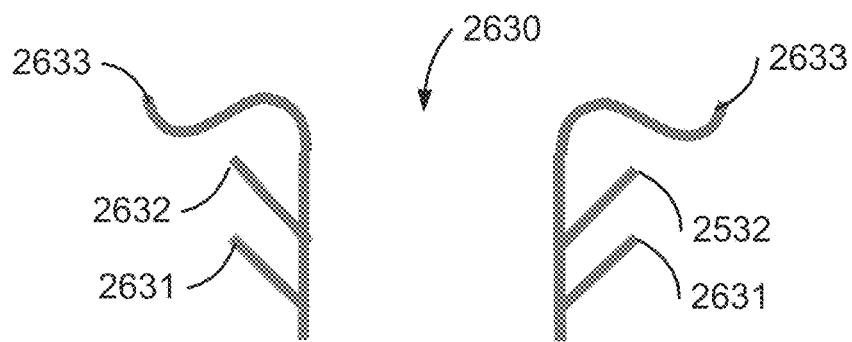
Figure 21A:
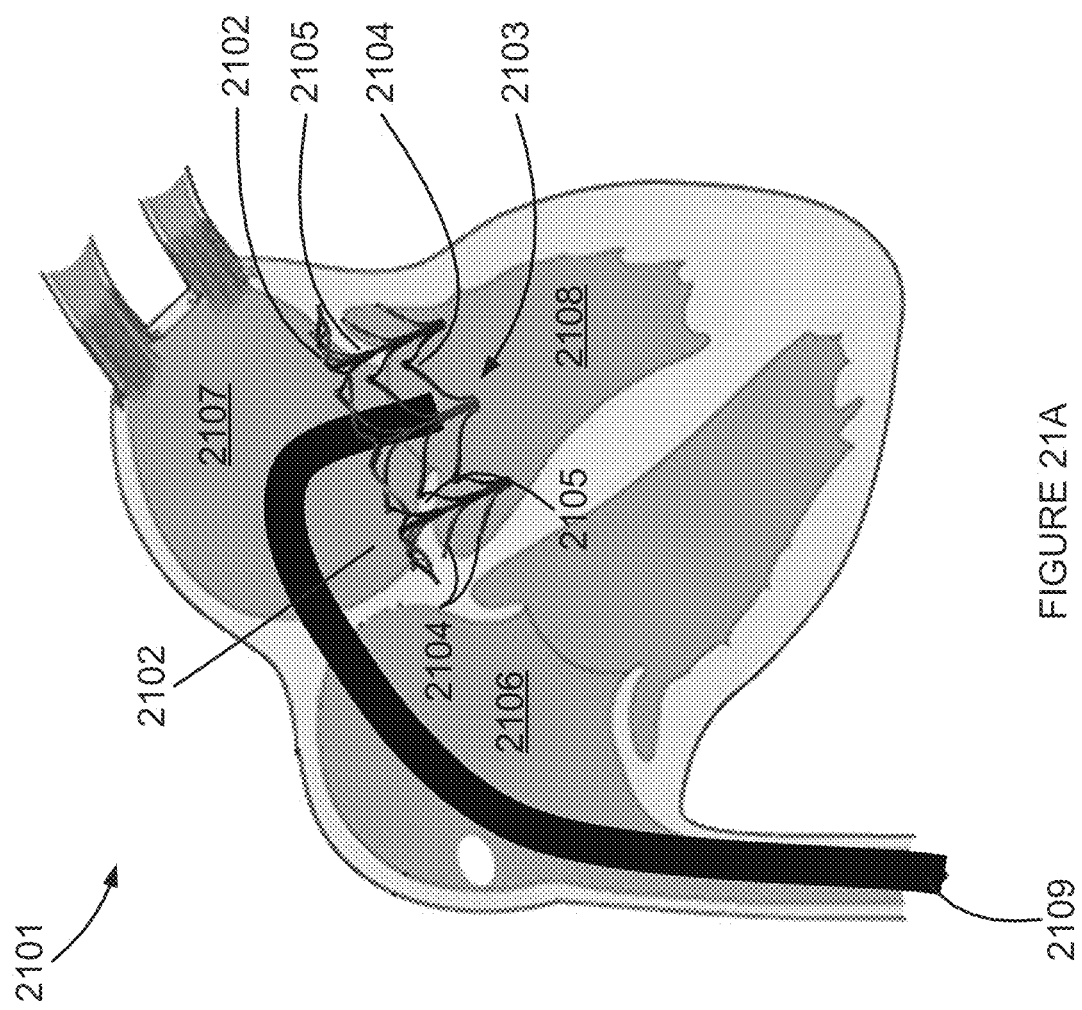
Figure 21C:
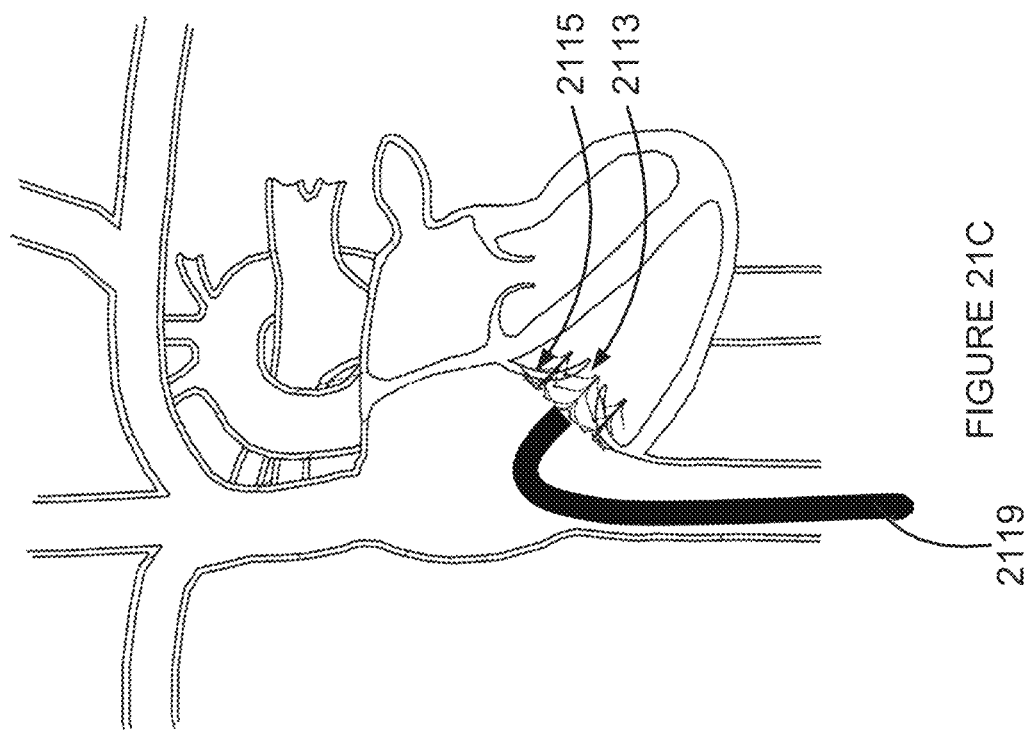
Figure 21B:
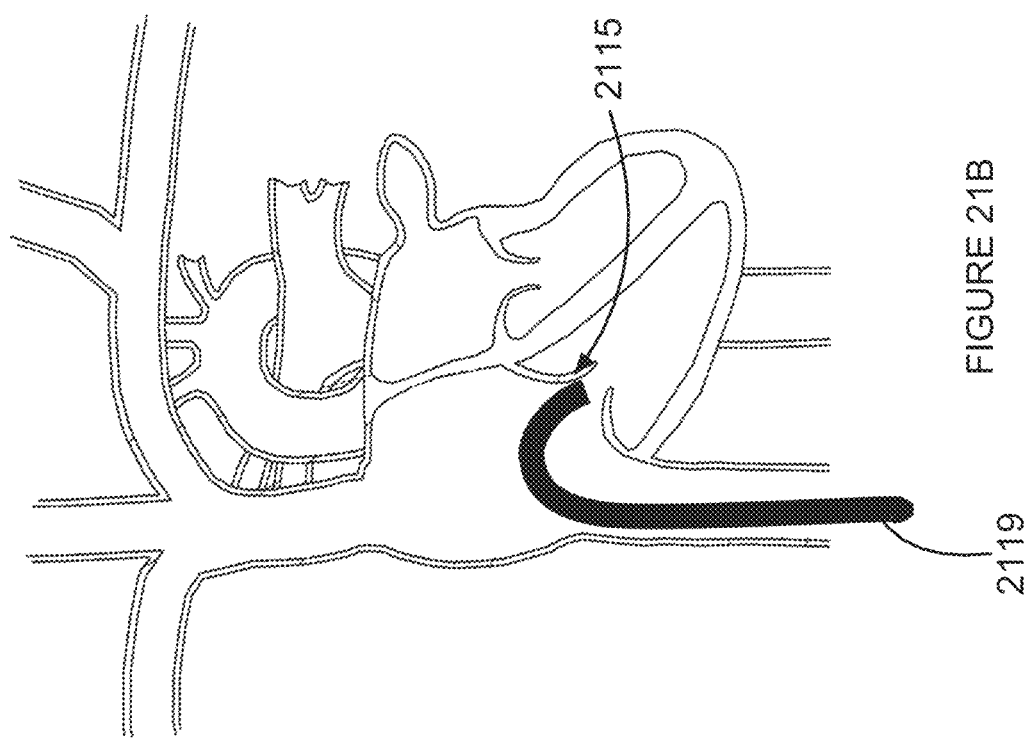
Figure 22A:
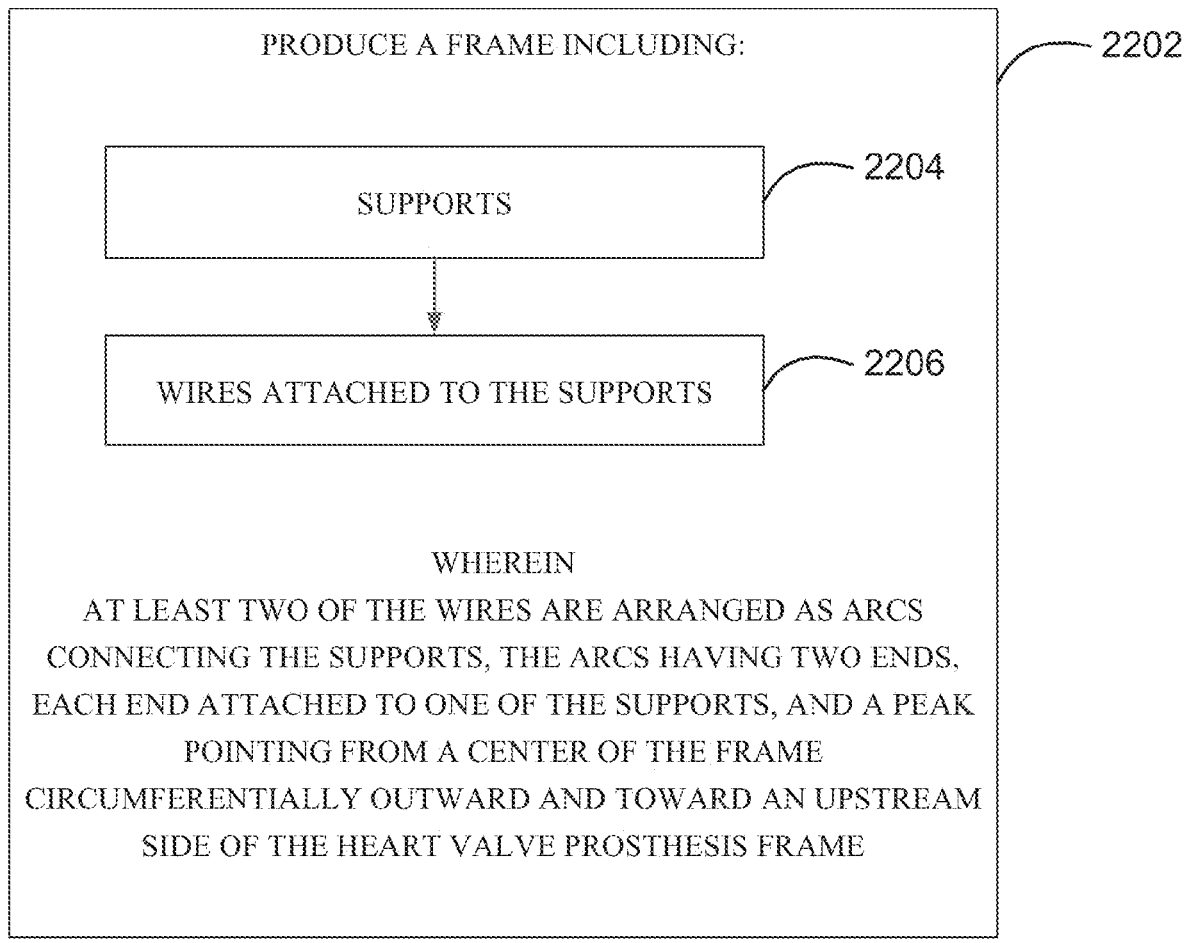
Figure 22B:
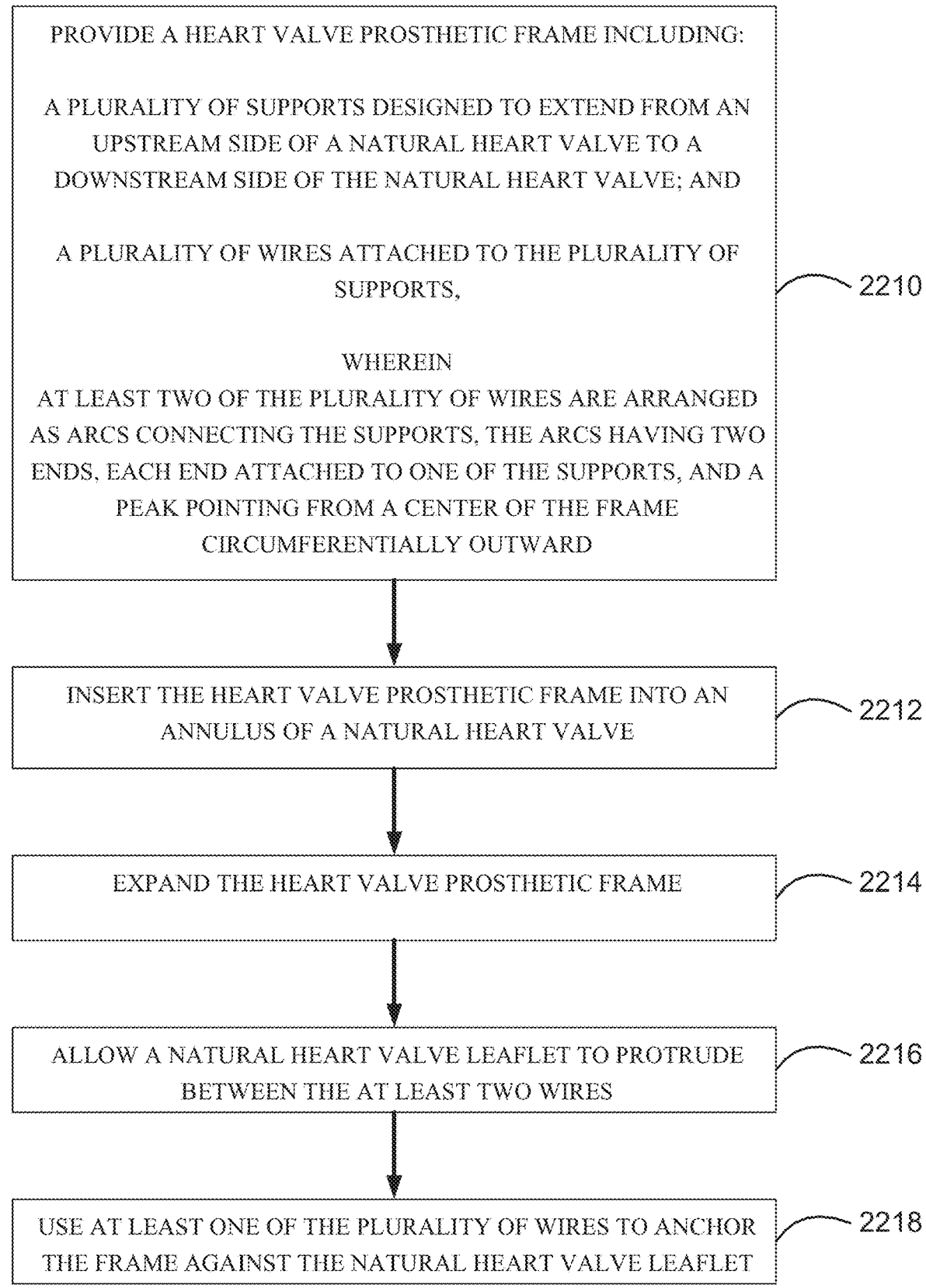
Figure 23:
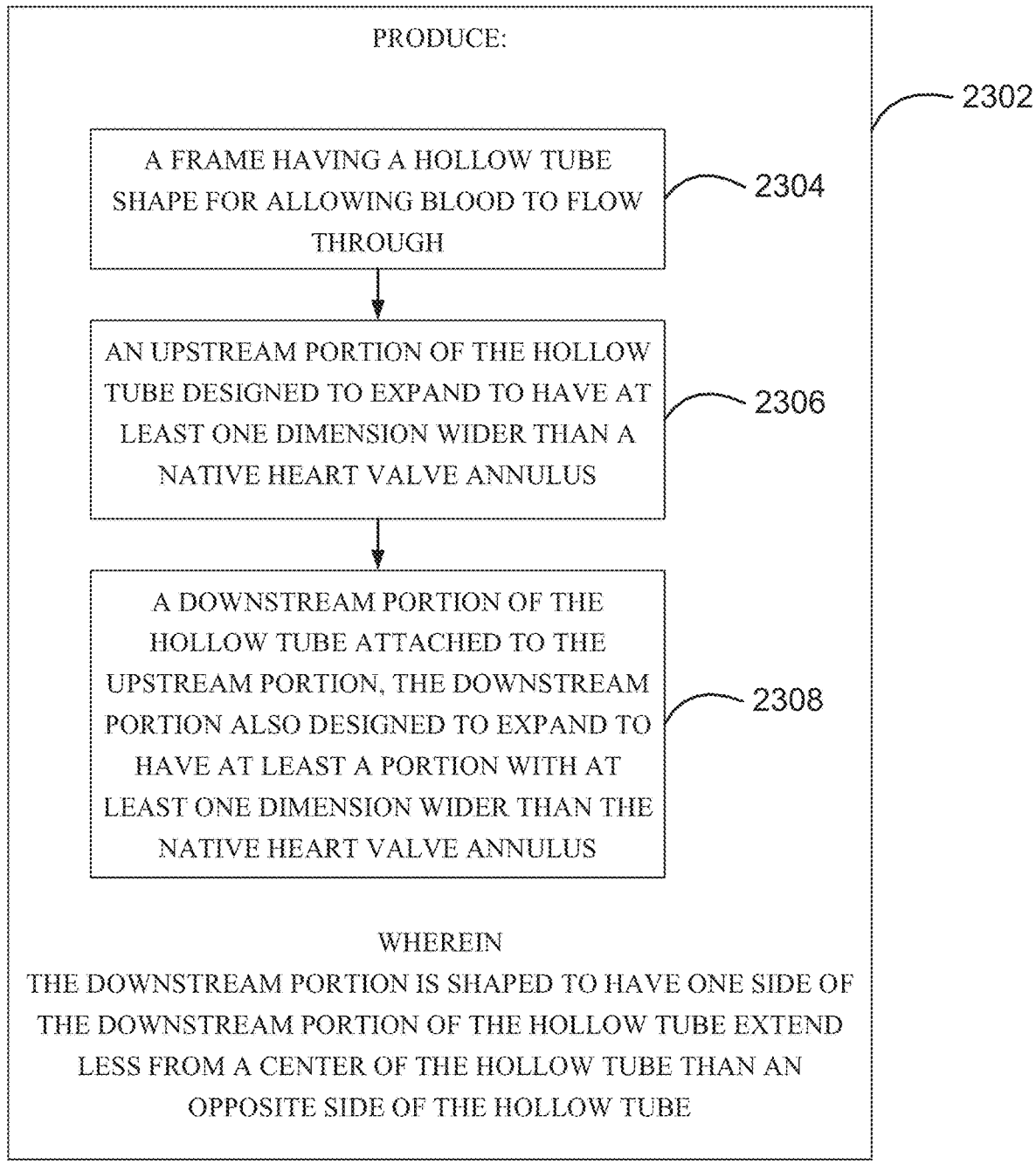
Figure 24:
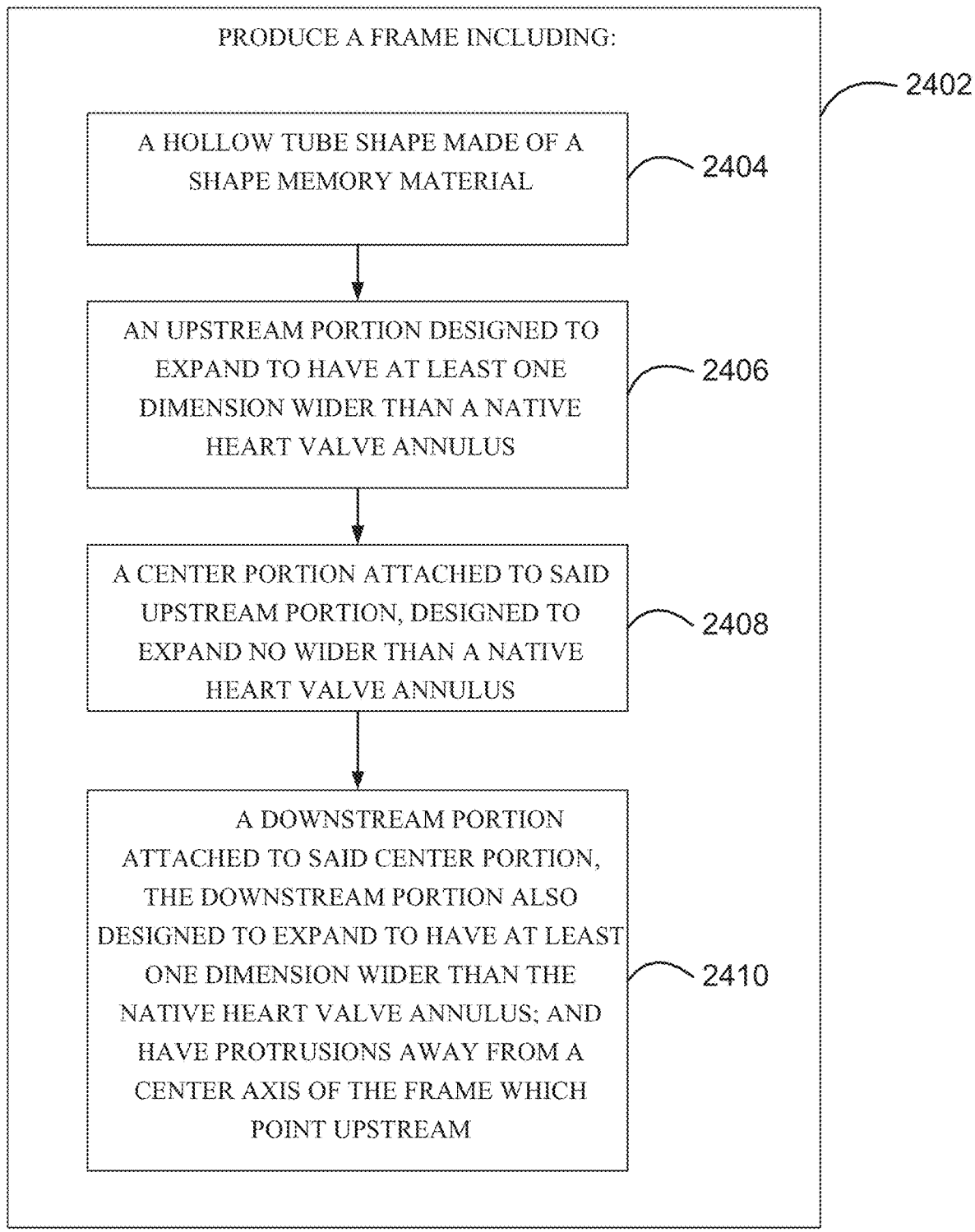
Figure 25:
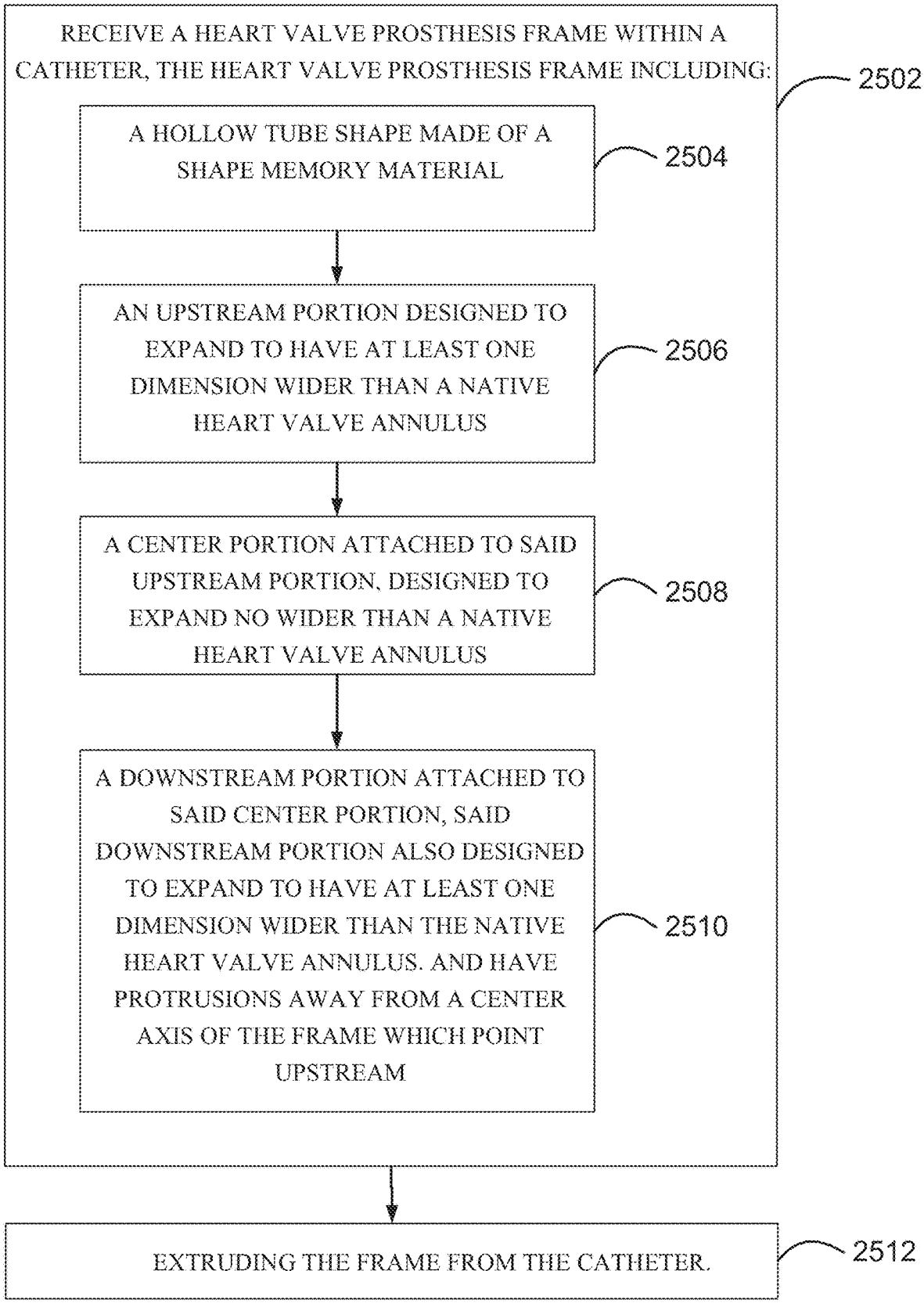
Figure 26C:
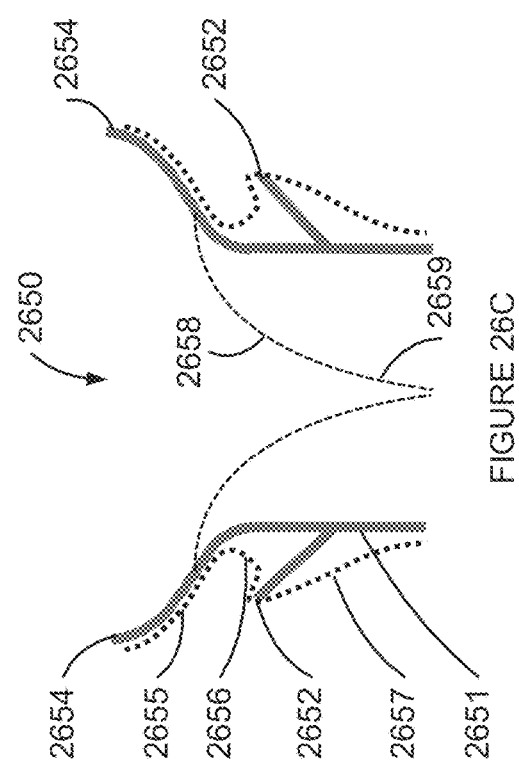
Figure 26D:
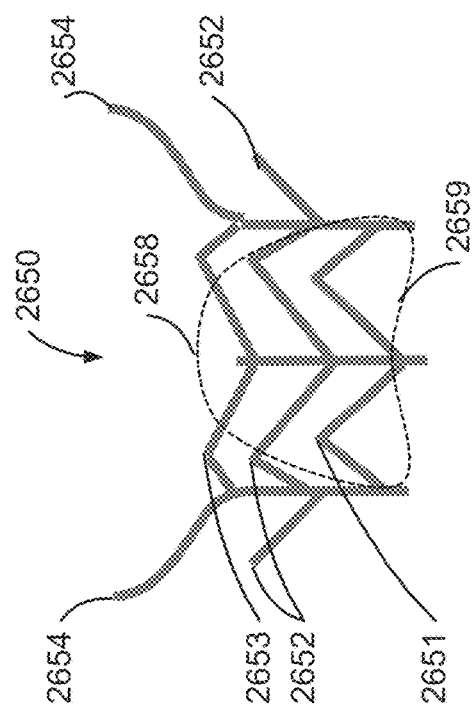
Figure 26A:
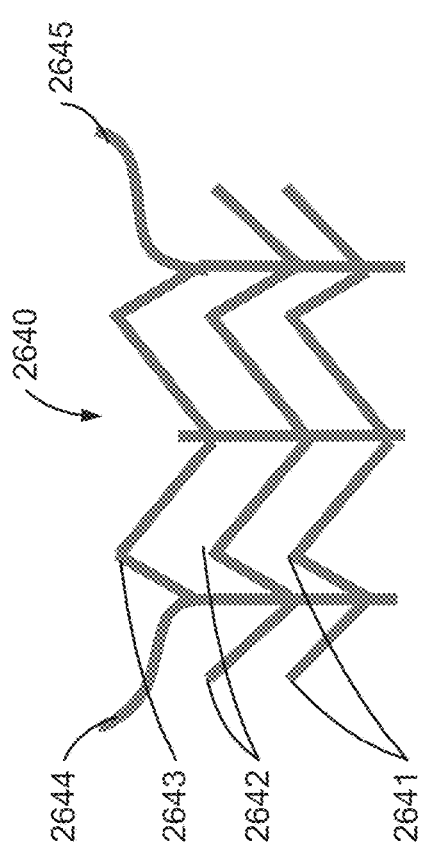
Figure 26B:
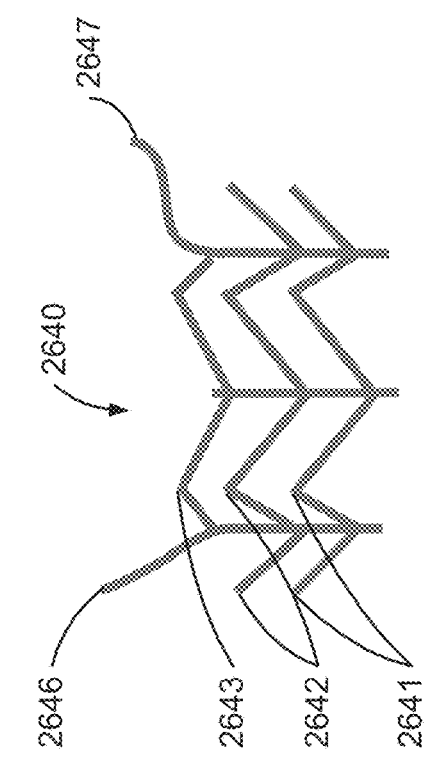
Figure 26G:
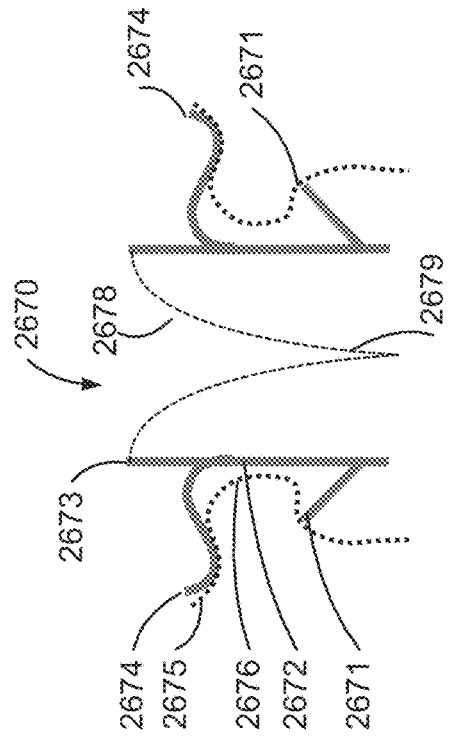
Figure 26H:
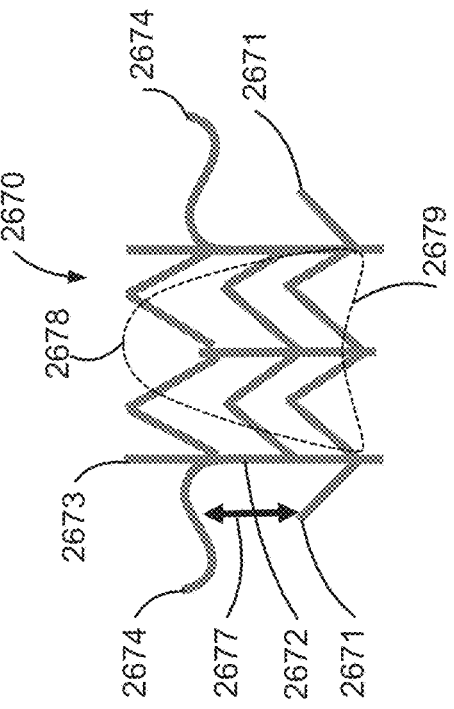
Figure 26E:
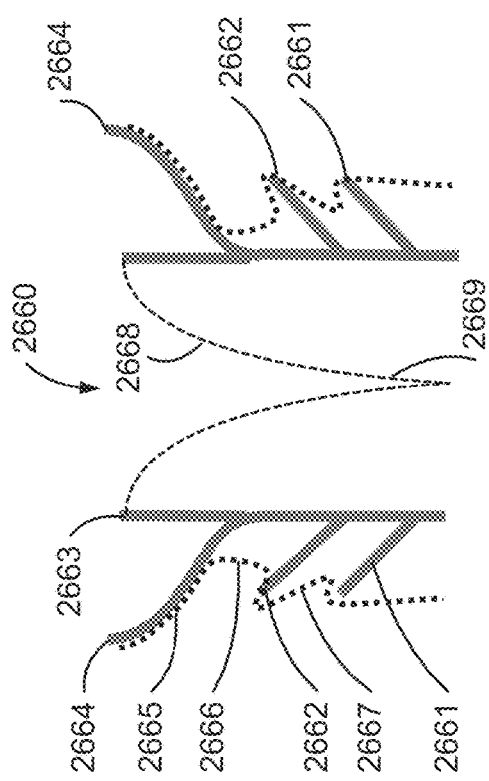
Figure 26F:
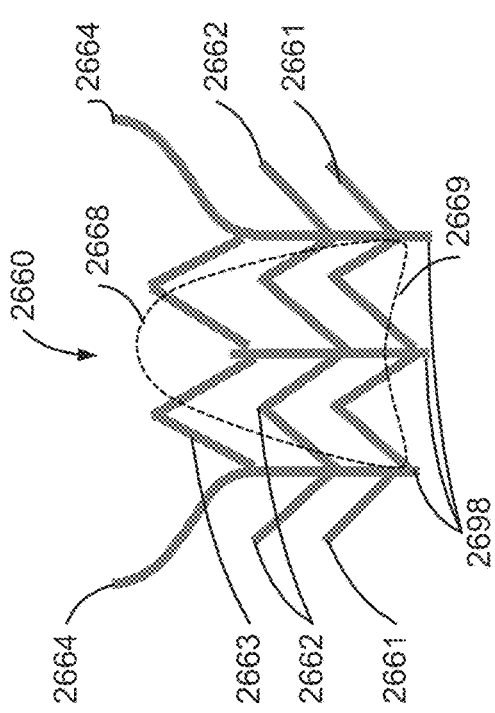
Figure 28C:
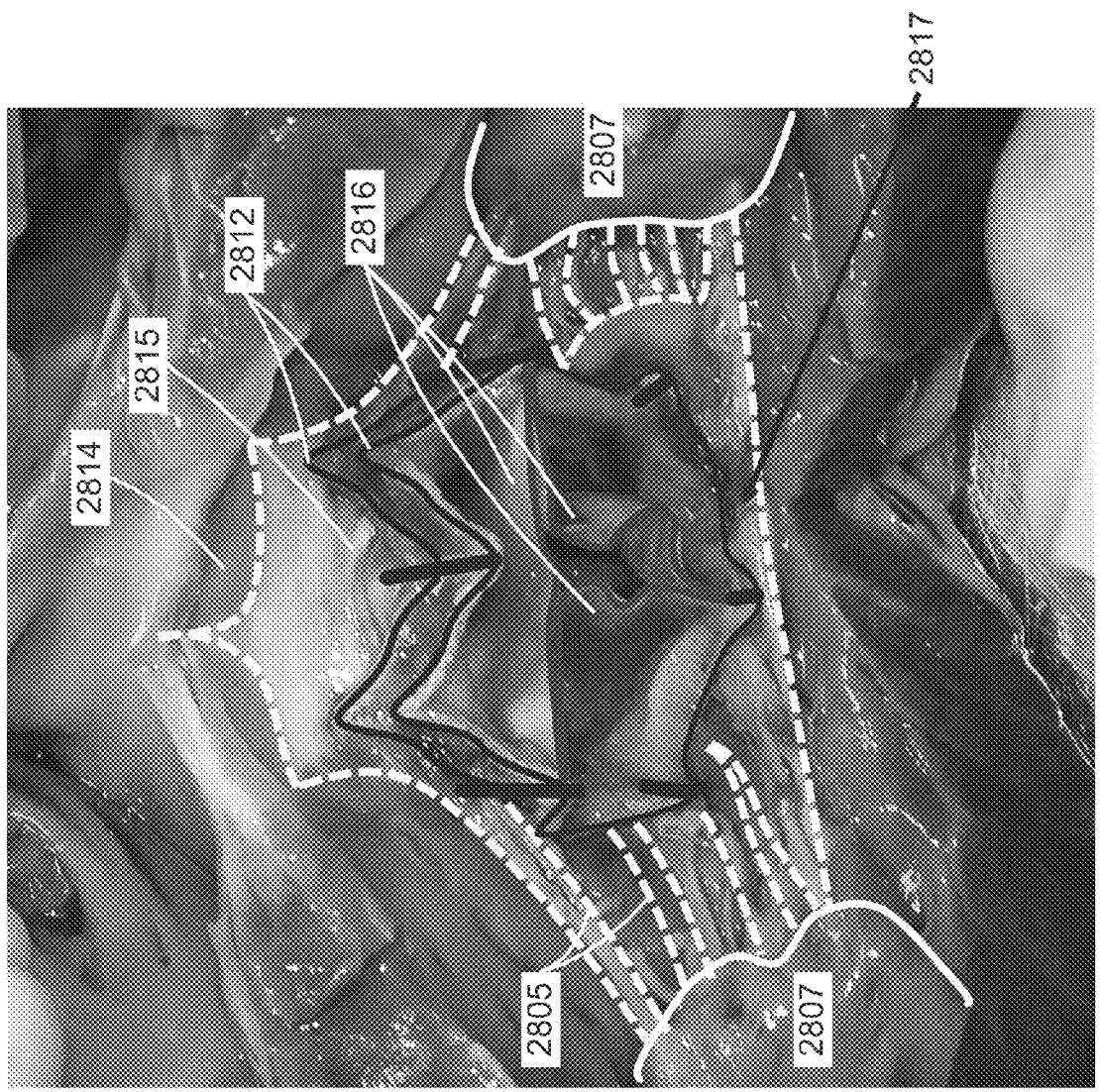
Figure 28D:
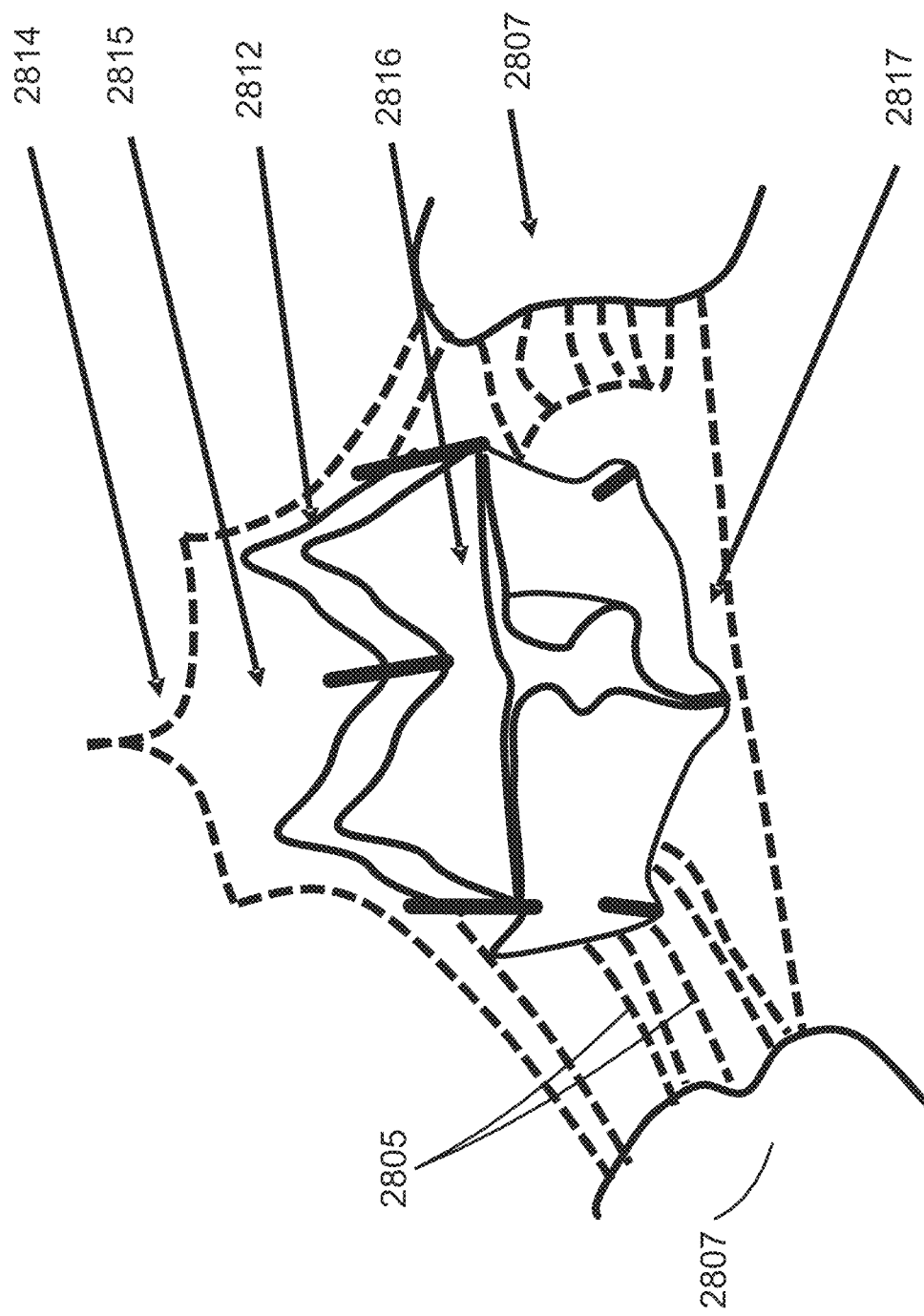
Figure 29B:
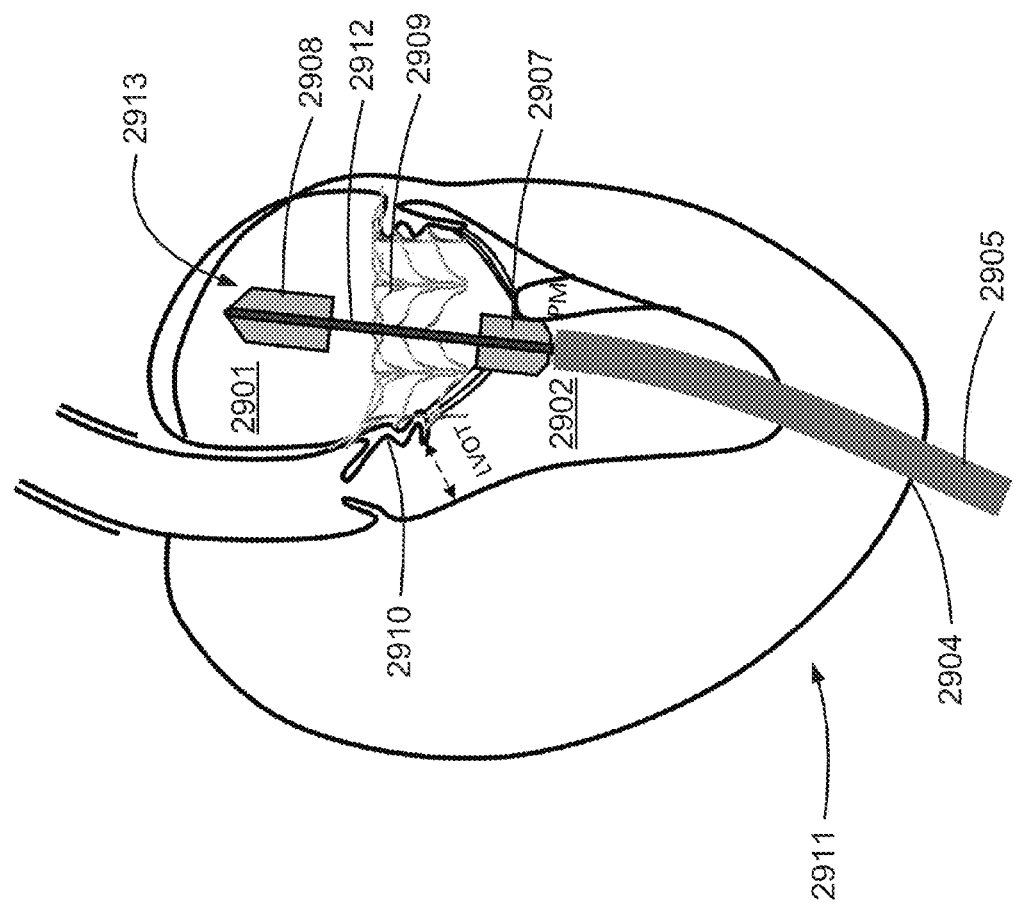
Figure 29A:
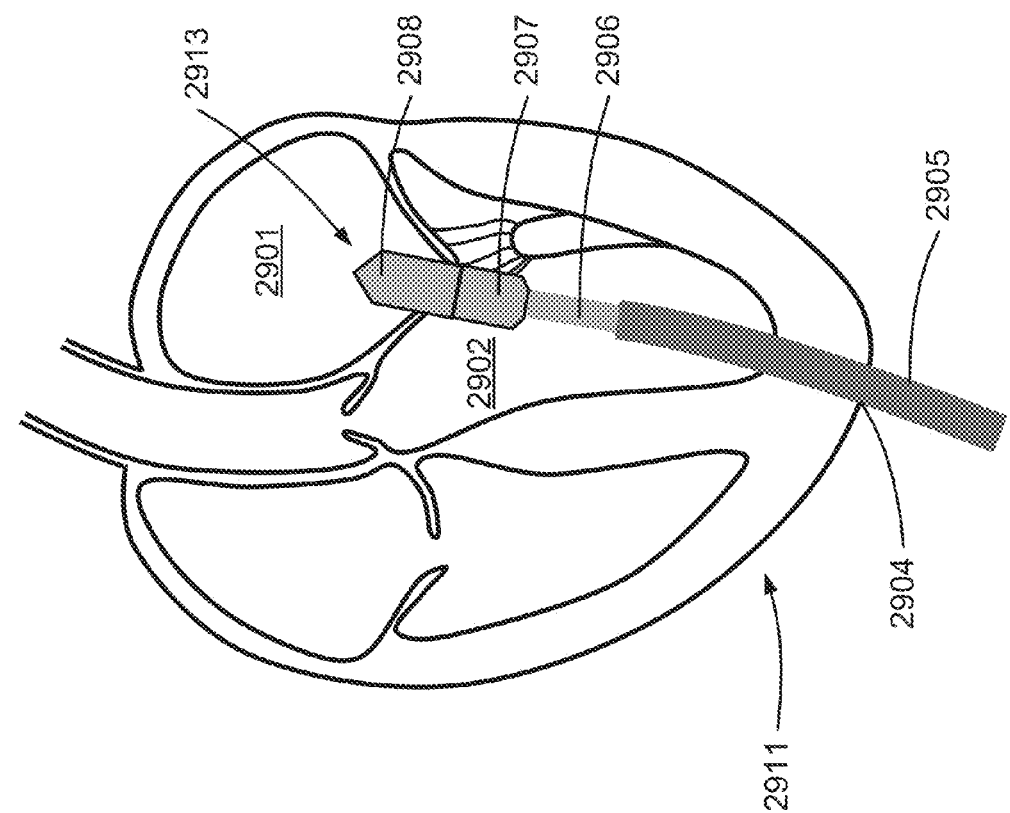
Figure 34A:
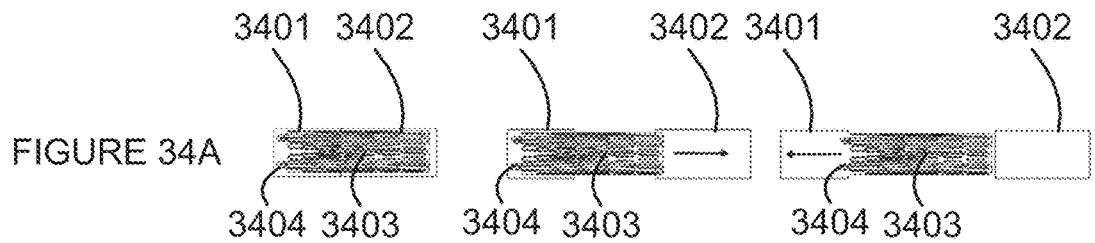
Figure 34B:
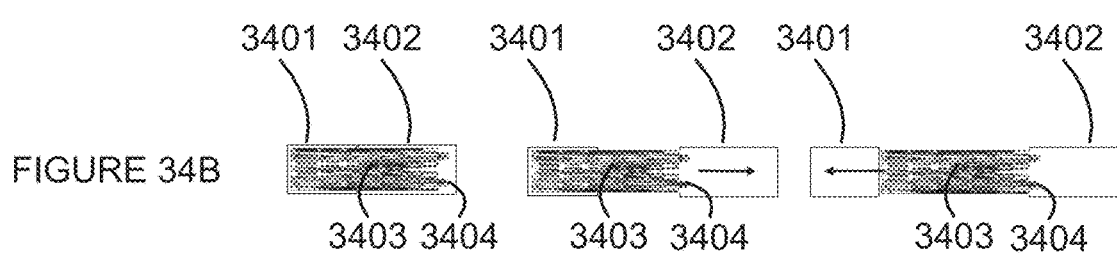
Figure 34C:
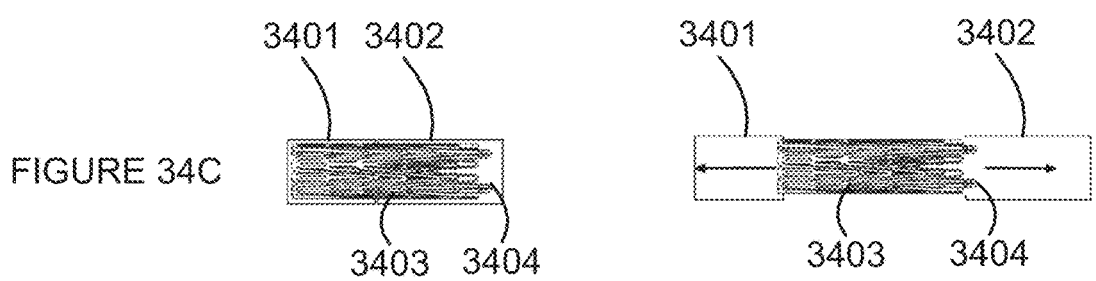
Figure 34D:
Figure 34E:
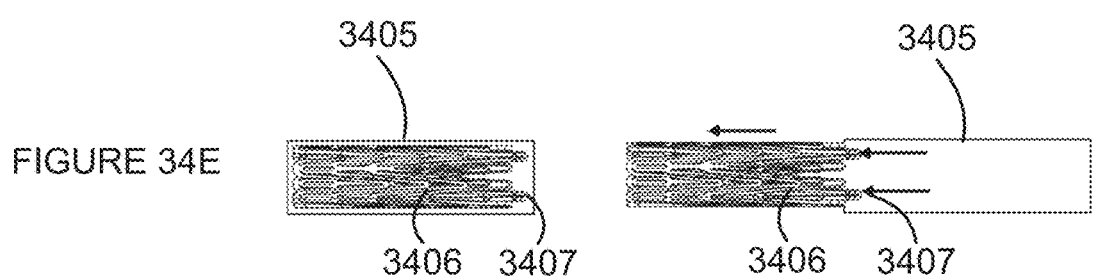
Figure 35:
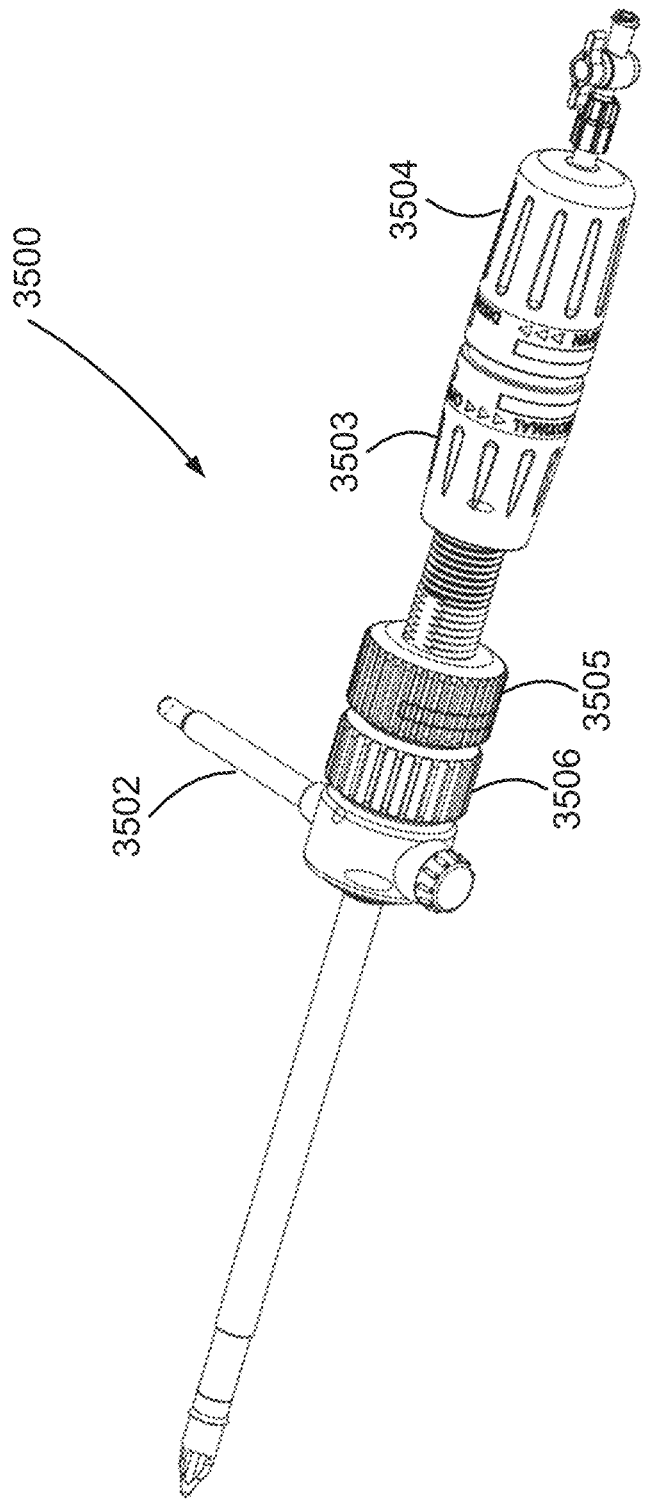
Figure 36:
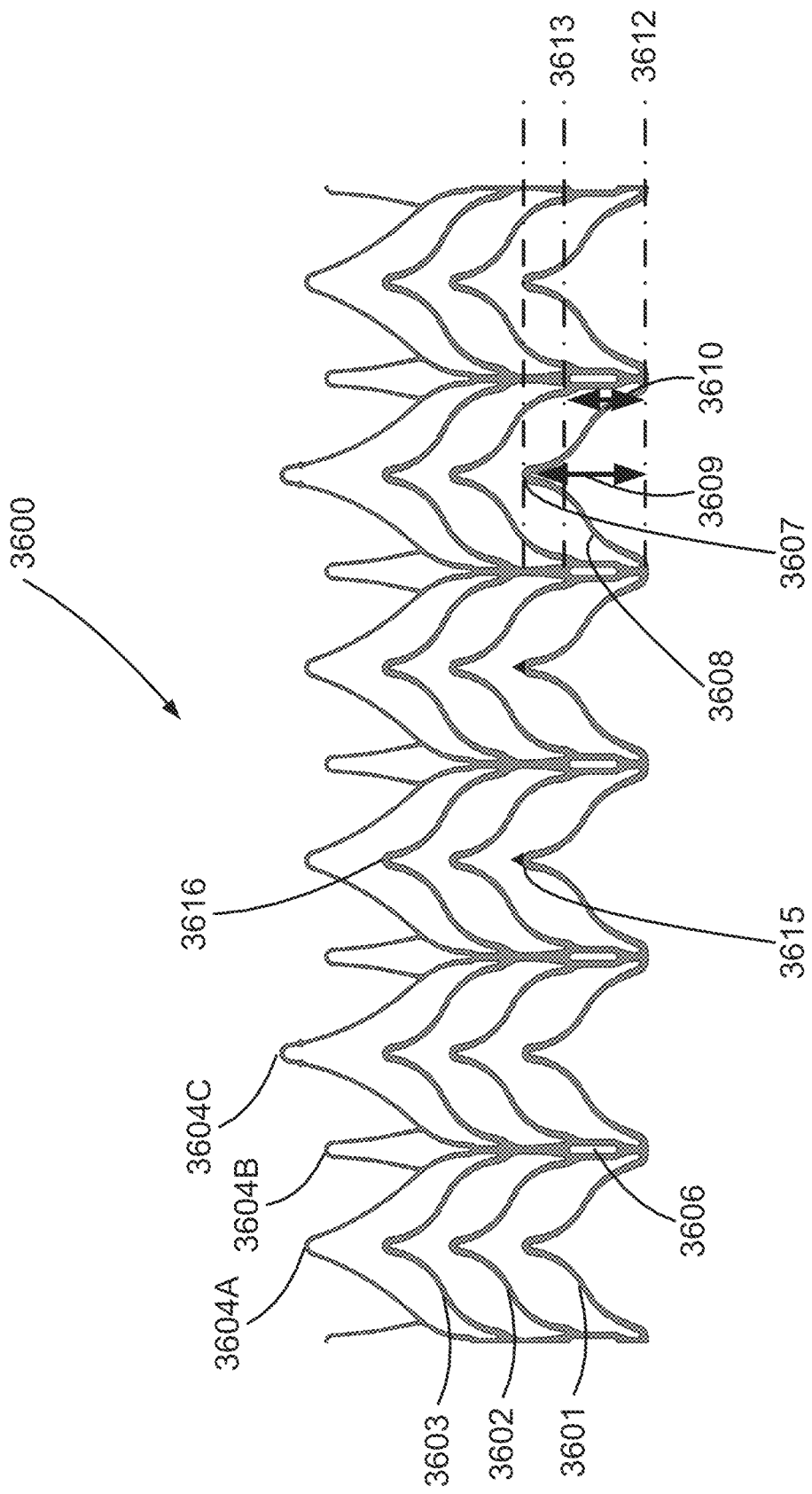

FIG. 12A is a simplified line drawing illustration of an internal frame for supporting an artificial heart valve constructed according to an example embodiment of the invention;

FIG. 12B is a simplified line drawing illustration of an external frame for supporting an heart valve prosthesis constructed according to an example embodiment of the invention;

FIG. 12C is a simplified line drawing illustration of a frame including an internal frame attached to an external frame according to an example embodiment of the invention;

FIGS. 13A, 13B, 13C, 13D and 13E are simplified line drawing illustrations of a heart valve prosthesis including an external frame attached to an internal frame and to an artificial heart valve, constructed according to an example embodiment of the invention;

FIGS. 14A, 14B and 14C are simplified line drawing illustrations of components of a heart valve prosthesis according to an example embodiment of the invention;

FIGS. 15A and 15B are simplified line drawing illustrations of a heart valve prosthesis constructed according to an example embodiment of the invention;

FIGS. 16A, 16B, 16C and 16D are simplified line drawing illustrations of a side view cross section of a frame of a heart valve prosthesis being released from a compressed shape and expanding according to an example embodiment of the invention;

FIGS. 17A, 17B, 17C and 17D are simplified line drawing illustrations of a frame according to an example embodiment of the invention;

FIGS. 18A, 18B, 18C and 18D are simplified line drawing illustrations of a frame according to an example embodiment of the invention;

FIGS. 19A and 19B are images of a heart valve prosthesis according to an example embodiment of the invention;

FIG. 20A is a simplified line drawing of a heart valve prosthesis frame according to an example embodiment of the invention;

FIG. 20B is a simplified line drawing of a heart valve prosthesis frame 2606 located in a heart according to an example embodiment of the invention;

FIGS. 20C-20F are simplified illustrations of several views of the heart valve prosthesis frame 2606 of FIG. 20B;

FIGS. 20G-20H are simplified line drawings of two views of the heart valve prosthesis frame 2606 of FIG. 20B;

FIGS. 20I-20K are simplified line drawings of cross-sectional views of optional embodiments of heart valve prosthesis frames according to an example embodiment of the invention;

FIG. 21A is a simplified line drawing of a cross sectional side view of a heart valve prosthesis frame in place in a natural heart according to an example embodiment of the invention;

FIGS. 21B and 21C are simplified line drawings of a procedure for placing a heart valve prosthesis frame in place in a right atrioventricular valve of a natural heart according to an example embodiment of the invention;

FIG. 22A is a simplified flow chart illustration of a method for producing a heart valve prosthesis frame, according to an example embodiment of the invention;

FIG. 22B is a simplified flow chart illustration of a method for anchoring a prosthetic heart valve, according to an example embodiment of the invention;

FIG. 23 is a simplified flow chart illustration of a method for producing a heart valve prosthesis frame, according to an example embodiment of the invention;

FIG. 24 is a simplified flow chart illustration of a method for producing a heart valve prosthesis frame, according to an example embodiment of the invention;

FIG. 25 is a simplified flow chart illustration of a method for shaping a heart valve prosthesis frame, according to an example embodiment of the invention;

FIGS. 26A-26B are simplified line drawings of two views of a heart valve prosthesis frame according to an example embodiment of the invention;

FIGS. 26C-26D are simplified line drawings of two views of a heart valve prosthesis frame according to an example embodiment of the invention;

FIGS. 26E-26F are simplified line drawings of two views of a heart valve prosthesis frame according to an example embodiment of the invention;

FIGS. 26G-26H are simplified line drawings of two views of a heart valve prosthesis frame according to an example embodiment of the invention;

FIG. 27A is a simplified illustration of a heart valve prosthesis frame located in a heart according to an example embodiment of the invention;

FIG. 27B is a simplified illustration of a single arc in a heart valve prosthesis frame according to an example embodiment of the invention;

FIG. 27C is a simplified illustration of the arc of FIG. 2B;

FIGS. 28A and 28B are simplified illustrations of a heart valve prosthesis frame 2800 located in a heart according to an example embodiment of the invention;

FIGS. 28C and 28D are illustrations of a heart and a prosthetic mitral valve placed in the heart;

FIGS. 29A and 29B are simplified line drawing illustrations of a cross sectional side view of delivery of a heart valve prosthesis frame into place in a natural heart according to an example embodiment of the invention;

FIGS. 30A-30I are images of a prosthetic mitral valve in a process of deployment from a delivery capsule according to an example embodiment of the invention;

FIGS. 31A and 31B are simplified line drawings of loading and unloading of a prosthetic mitral valve into a delivery capsule according to an example embodiment of the invention;

FIG. 31C is an image of a delivery capsule and a prosthetic mitral valve according to an example embodiment of the invention;

FIGS. 32A-32D are simplified illustrations of a delivery capsule in various stages of delivering a prosthetic mitral valve according to an example embodiment of the invention;

FIGS. 33A-33D are simplified illustrations of a delivery capsule in various stages of delivering a prosthetic mitral valve according to an example embodiment of the invention;

FIGS. 34A-34C are simplified illustrations of various methods of releasing a prosthetic mitral valve from a delivery capsule according to an example embodiment of the invention;

FIGS. 34D and 34E are simplified illustrations of various methods of releasing a prosthetic mitral valve from a delivery capsule according to an example embodiment of the invention;

FIG. 35 is a simplified illustration of a delivery system for delivering a prosthetic mitral valve by catheter according to an example embodiment of the invention; and FIG. 36 is a simplified illustration of a prosthetic mitral valve frame according to an example embodiment of the invention.

DESCRIPTION OF SPECIFIC EMBODIMENTS OF THE INVENTION

The present invention, in some embodiments thereof, relates to a cardiac valve prosthesis, and more particularly, but not exclusively, to a cardiac valve prosthesis for a mitral valve.

Introduction

The term "frame" is used throughout the present specification and claims to mean a support for a cardiac valve. In some embodiments, the cardiac valve is optionally a tissue or sheet of material or fabric designed to act as a cardiac valve, attached to the frame. In some embodiments the cardiac valve is optionally a plastic and/or synthetic and/or metal valve.

The term "heart valve prosthesis" is used throughout the present specification and claims to mean a for a cardiac valve prosthesis, which includes an artificial valve and one or more supporting and/or anchoring frame(s). Example embodiments of the present invention are described with reference to the mitral valve. However, examples provided with reference to the mitral valve are also applicable to the tricuspid valve, and their descriptions are meant to apply also to the tricuspid valve.

The tricuspid valve is exposed to different pressure loads, which are typically in a range of 15-50 mmHg. Mitral valve pressure loads are typically higher and can reach more than 210 mmHg.

In some embodiments a prosthetic heart valve and/or a prosthetic heart valve frame are optionally designed with a thinner frame and/or thinner frame wires and/or struts than a prosthetic heart valve and/or a prosthetic heart valve frame for use in a mitral valve.

An aspect of some embodiments of the invention involves a frame including one or more rows of arcs between longitudinal struts, with an apex or tip of the arcs toward an upstream part of the frame and feet of the arcs toward a downstream part of the frame. The term "arc" in all its grammatical forms is used in the application and claims to mean a tapered or ogive shape, such as used in engineering, architecture, or woodworking.

The arcs provide flexibility between the struts for compressing the frame into a delivery capsule or catheter, and provide spring power against compression when expanded inside a body, for example in a heart valve.

In some embodiments, one or more of the arcs are shaped so that their feet are connected to struts shaping a lumen of the frame, and their tips are bent away from an axis of the lumen, jutting out from a circumference of the lumen. Such tips optionally serve for anchoring the frame in a heart valve. The anchoring is optionally performed by pushing into natural walls of the heart valve, and/or beneath an annulus of the heart valve, and/or capturing a leaflet of the heart valve, and/or pushing up a fold of the heart walls or heart valve walls.

The arcs potentially enable inserting a lumen frame as a single wall layer into a delivery capsule or catheter, and benefiting from providing rigidity against compression of the lumen by the arcs pushing the struts apart, and at the same time providing frame anchors by arcs jutting out of the lumen shape. Inserting a single wall layer into a delivery capsule or catheter means that looking from a middle of a lumen there is just one layer of frame before a wall of the catheter or delivery capsule are reached.

In some embodiments, some or all arcs do not jut out of the lumen shape, and are not used for anchoring.

By way of some non-limiting examples:

A row of arcs is optionally pre-conditioned by shape memory to jut out of the frame lumen and another row is optionally pre-conditioned by shape memory not to jut out of the frame lumen.

One or more rows of arcs are optionally pre-conditioned by shape memory to jut out of the frame lumen and one or more rows are optionally pre-conditioned by shape memory not to jut out of the frame lumen.

Some arcs in a row of arcs are pre-conditioned by shape memory to jut out of the frame lumen and some arcs in the same row are optionally pre-conditioned by shape memory not to jut out of the frame lumen.

In some embodiments, the arc tips are rounded, in order not to penetrate the tissue against which they are intended to push.

In some embodiments, the arc tips are sharp or pointed, in order to penetrate the tissue against which they are intended to push. In some embodiments the penetration is limited by the sharp tip shape becoming wider over a short distance, so that a breadth of the tip limits depth of penetration.

By way of some non-limiting examples:

A row of arcs optionally has sharp tips.

One or more rows of arcs optionally have sharp tips and one or more rows optionally have rounded tips.

Some arcs in a row of arcs have sharp tips and some arcs in the same row have rounded tips.

In some embodiments, a frame optionally includes some sharp arc tips, for example to penetrate into natural heart valve leaflets or into a heart valve annulus, and some arc rounded arc tips which are not intended to penetrate.

In some embodiments a potential further benefit of using an arc shape is that an arc for jutting out of a lumen circumference may be taller than an inter-arc-row spacing, as will be shown below, for example in FIG. 36. An inter-arc-row spacing is a distance between arc feet, for example. The arcs are optionally directed with their tips in a same direction, so tops of arcs can pass between feet of arcs of a row above.

In some embodiments, arcs which are pre-conditioned to jut out from a circumference of the frame lumen are bent at a relatively small angle such as 30 degrees or less, or 45 degrees or less, at 60 degrees or less. Such jutting arcs benefit from decreased bending forces on the arc feet, than if they were jutting out at 90 degrees. An additional potential benefit is that shape-memory material can be pre-conditioned to bend at smaller angles.

An aspect of some embodiments of the invention involves a frame shaped so that the frame crimps, or pinches, natural cardiac valve leaflets, or the natural heart valve annulus.

In some embodiments, the crimping of the natural cardiac valve leaflets is used for sealing against blood flow around the frame.

In some embodiments, the crimping of the natural cardiac valve leaflets is used for anchoring the frame in place.

In some embodiments, the crimping of the natural cardiac valve leaflets is used for limiting motion of the natural cardiac valve leaflets. In some embodiments limiting the motion of the natural cardiac valve leaflets optionally serves to limit the natural cardiac valve leaflets from being pushed aside by the frame and possibly into a blood flow path. By way of a non-limiting example, the frame optionally crimps an anterior leaflet of the natural mitral valve of the left ventricle, preventing the anterior leaflet from being pushed into a blood flow path of the aortic valve leading blood out of the left ventricle.

An aspect of some embodiments of the invention involves a frame shaped so that the frame crimps, or pinches, a natural cardiac valve annulus, or leaflet, or heart wall.

In some embodiments, the crimping of the natural cardiac valve annulus is used for anchoring the frame in place.

In some embodiments, the crimping of the natural cardiac valve annulus is used for sealing against blood flow around the frame.

In some embodiments the frame is shaped so that the frame crimps, or pinches, a natural cardiac valve annulus, or leaflet, or heart wall, without presenting any sharp toward the natural cardiac valve annulus, or leaflet, or heart wall.

An aspect of some embodiments of the invention involves a frame designed to pass through a catheter as a lumen or tube as a frame having a lumen with a single layer, and when released from the catheter, to expand and have a portion of the frame expand so that at least some of the frame becomes a double layered lumen.

In some embodiments, the above-mentioned frame design is used so that a relatively thin catheter can serve to insert a double layered frame, which would not otherwise pass through the catheter.

In some embodiments, the above-mentioned frame design is used to insert a double layered frame, which would not otherwise pass through the catheter.

In some embodiments, the double layered frame provides more resistance to sideways compression forces produced in a course of a natural heartbeat, and potentially maintains its shape better against the sideways compression forces than a single walled frame.

An aspect of some embodiments of the invention involves a frame designed to pass through a catheter as a lumen or tube as a frame having a lumen with a single layer, and when released from the catheter, to expand and have a downstream portion of the frame expand, so that at least some of the downstream portion of the frame points away from a center lumen in the frame, toward internal sides of the heart walls or toward the heart valve annulus, and also toward an upstream direction.

In some embodiments, the downstream portion pointing toward internal sides of the heart walls and also upstream provides elastic resistance to upstream forces produced in a course of a natural heartbeat, and potentially maintains its location against the upstream forces without being forced upstream through the annulus.

An aspect of some embodiments of the invention involves a frame profile designed, when expanded, to curve both over the top of the natural mitral valve annulus and under the natural mitral valve annulus.

In some embodiments, the above-mentioned design is used for anchoring the frame, so that an expanded frame prevented from falling entirely below the mitral valve annulus, and prevented from passing entirely above the mitral valve annulus In some embodiments, the curve under the natural mitral valve annulus is optionally less wide on an anterior leaflet side of a mitral valve, protruding less on a side of the blood flow path of the aortic valve leading blood out of the left ventricle.

An aspect of some embodiments of the invention involves a frame designed, when expanded, to produce a shape wider than the natural mitral valve annulus, at least in one direction, in the left atrium, and also wider than the natural mitral valve annulus, at least in one direction, in the left ventricle.

In some embodiments, the above-mentioned frame design is used so that an expanded frame is prevented from falling entirely below the mitral valve annulus, and prevented from passing entirely above the mitral valve annulus.

Figure 1:
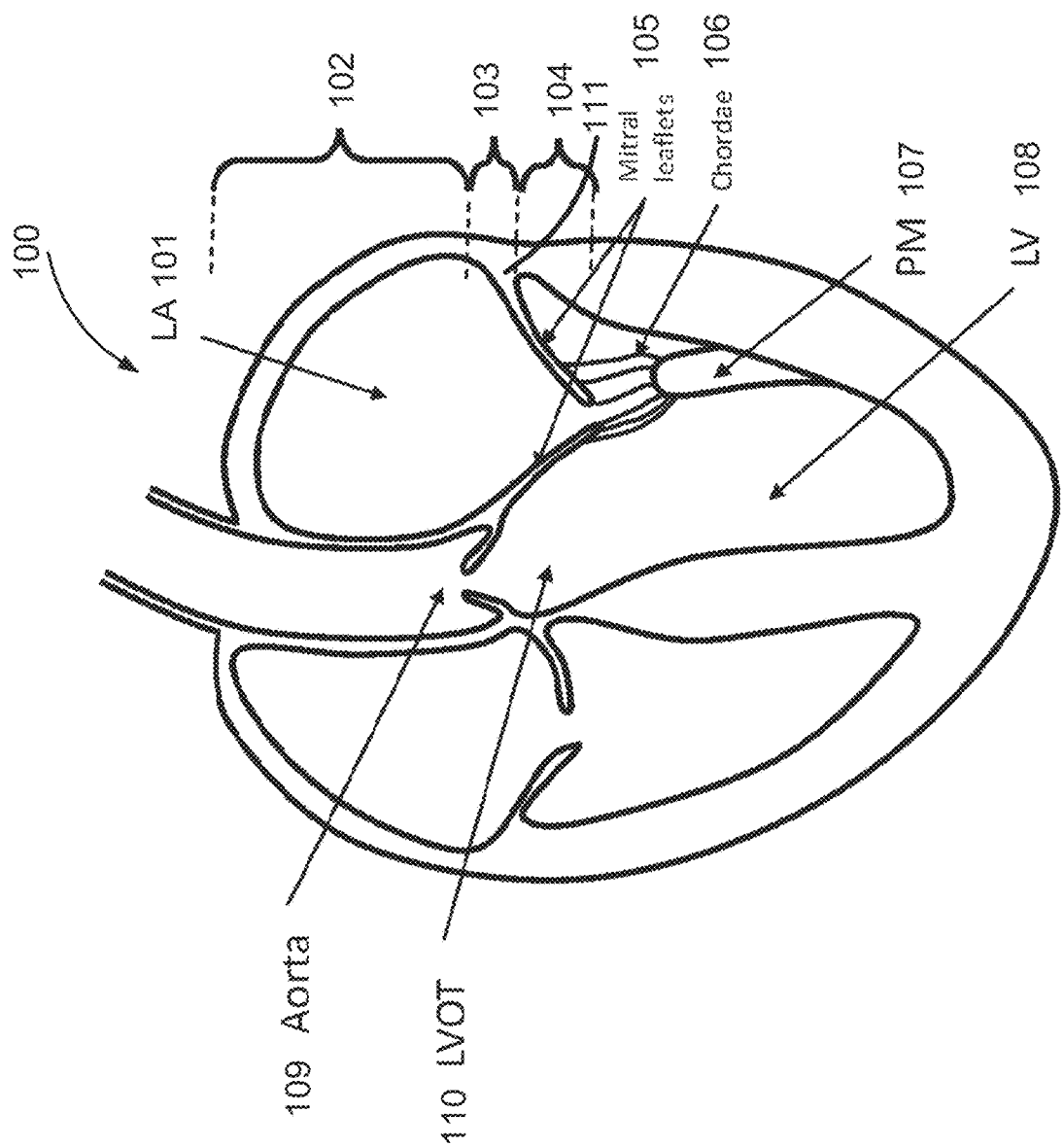

For purposes of better understanding some embodiments of the present invention, reference is first made to FIG. 1, which is a simplified line drawing of a cross section of a heart 100.

FIG. 1 shows parts of the heart 100 which will be referred to later in the present application.

FIG. 1 shows the left atrium 101, the left ventricle 108, the left ventricular outflow tract 110 and the aorta 109.

FIG. 1 also shows portions of the mitral valve such as the mitral leaflets 105, the mitral annulus 111, the chordae 106 and the papillary muscle 107.

FIG. 1 also shows portions of the heart—a left atrium 102, an annulus portion 103 and a sub-leaflet portion 104.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 2A:
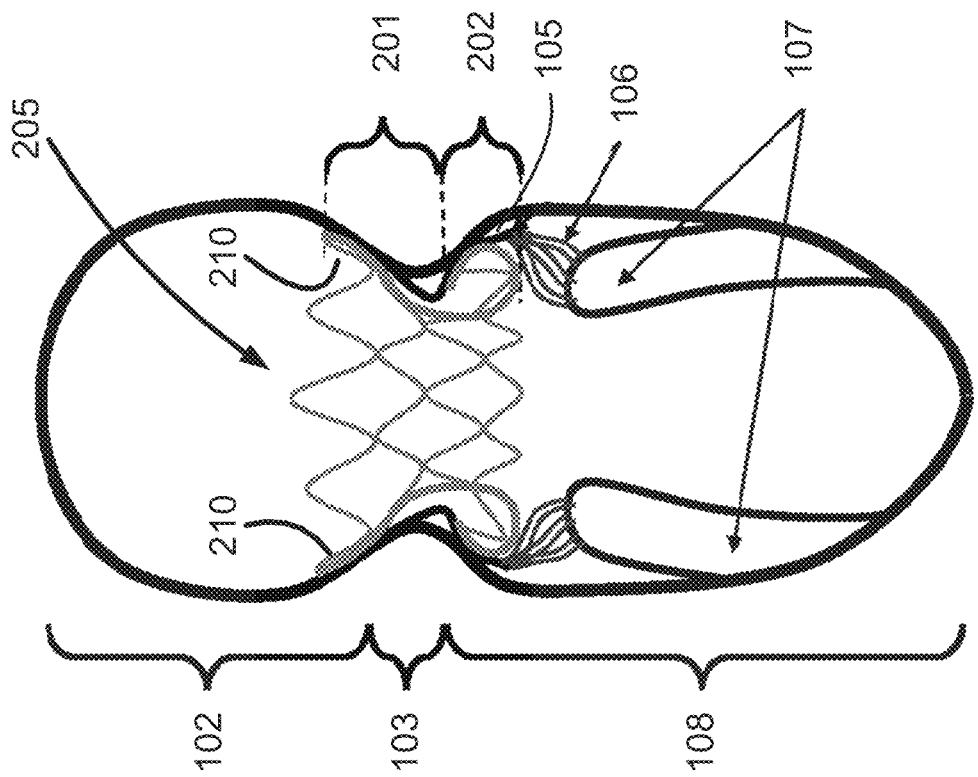

Reference is now made to FIGS. 2A and 2B, which are simplified line drawing illustrations of a cross section of a heart and a heart valve prosthesis frame 205 located in the natural mitral valve according to an example embodiment of the invention.

FIG. 2A shows portions of the heart introduced in FIG. 1—the left atrium 102, the annulus portion 103, the left ventricle 108, the papillary muscle 107, the chordae 106, the mitral valve leaflet 105.

FIG. 2A also shows a frame 205, including a top portion 201, also termed an onion portion, and a bottom portion 202, also termed an apple portion, located at the location of the natural mitral valve of the heart.

The terms "onion" and "onion portion" in all their grammatical forms are used throughout the present specification and claims to mean a portion of a frame which is configured to be upstream of the natural mitral valve annulus. It is noted that other components of the frame may be configured to be upstream of the natural mitral valve annulus, and that can be understood by a drawing or text describing those components.

FIG. 2B shows a small part of the cross section of the heart, including the annulus 103, and the frame 205.

The frame 205 is made of an expandable stent 209.

Attention is directed to a profile 210 of an outside shape of the frame 205.

In some embodiments the profile 210 is optionally constructed of a single piece of material, optionally metal, optionally Nitinol. In some embodiments the profile 210 is optionally constructed of a single piece of material, optionally metal, optionally cobalt chrome. In some embodiments the profile 210 is optionally constructed of a super elastic material.

In some embodiments the construction of the frame 205 of a single piece of material is enabled by a gradual bending of the profile 210 of the frame 205, without a sharp bend.

In some embodiments the construction of the frame 205 includes a bottom portion 211 of the frame 205 bending outward of a center lumen of the frame 205 and back in, presenting one or both of the following potential features:
the bottom portion 211 reaching close to an upper portion 212 and potentially close enough to be able to exert a pinching action on the natural annulus.
the bottom portion 211 bending back in toward the center lumen of the frame 205 so that a tip or end of the bottom portion 211 of the frame 205 is not directed toward the natural annulus and so will not present a potential for pricking or wounding the natural annulus and/or the natural valve leaflet.

In some embodiments the bottom portion 211 of the frame 205 acts as a spring, cushioning hydraulic pressure from the left ventricle toward the annulus, by elastic bending, absorbing the pressure and/or spreading the pressure on the bottom of the annulus.

In some embodiments the bottom portion 211 of the frame 205 includes wires bending out from the center lumen of the frame 205 and back in toward the center lumen only at locations corresponding to commissures of the natural heart valve leaflets. Such a bottom portion 211 potentially does not push on or catch the natural heart valve leaflets, and does provide anchoring against walls of the heart without presenting a potential for pricking or wounding the natural annulus and/or the natural valve leaflet.

In some embodiments the frame 205 includes outward facing teeth (not shown), to prevent the frame 205 from slipping along heart walls, the annulus, or the leaflets.

It is noted that the various embodiments described herein and/or shown in the drawings may all optionally include outward facing teeth to prevent the various frame embodiments from slipping along heart walls, the annulus, or the leaflets.

Figure 3:
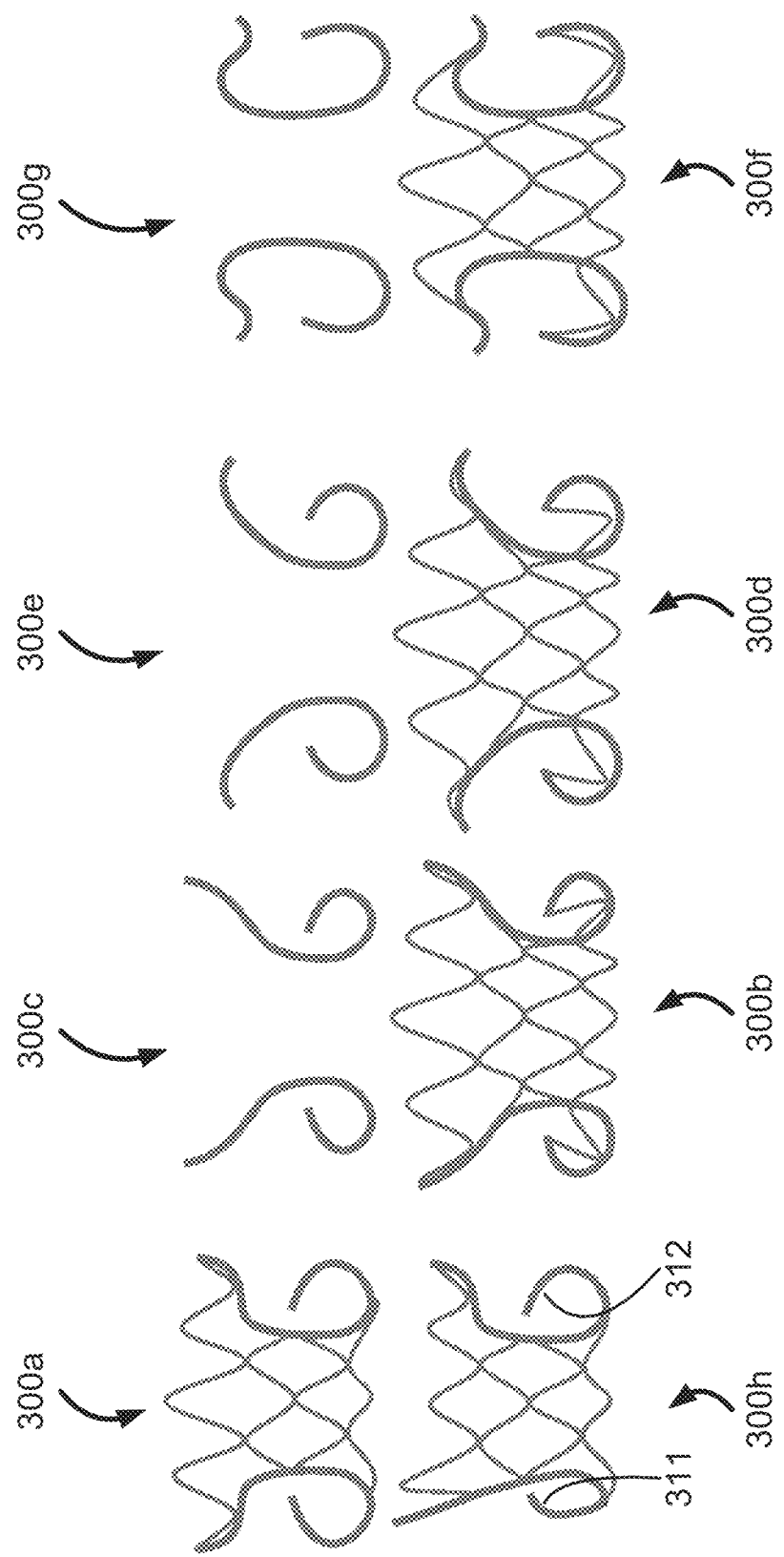

Reference is now made to FIG. 3 which is a set of simplified line drawing illustrations of a cross section of a heart valve prosthesis frame according to an example embodiment of the invention.

FIG. 3 shows various drawings 300a-h of some non-limiting example shapes of cross sections of the frame 205 of FIGS. 2A and 2B. Attention is directed to profiles of an outside shape of the various drawings, some of which share properties of the profile of the outside shape shown in FIG. 2B.

A first drawing 300a shows a first symmetric profile of a first shape of the frame, including a stent mesh.

A second drawing 300b and a third drawing 300c show a second symmetric profile of the frame, in two drawings, the second drawing 300b including a stent mesh and the third drawing 300c without the stent mesh. The second drawing 300b and the third drawing 300c show a different shape of the frame than other drawings of FIG. 3.

A fourth drawing 300d and a fifth drawing 300e show a third symmetric profile of the frame, in two drawings, the fourth drawing 300d including a stent mesh and the fifth drawing 300e without the stent mesh. The fourth drawing 300d and the fifth drawing 300e show a different shape of the frame than other drawings of FIG. 3.

A sixth drawing 300f and a seventh drawing 300g show a fourth symmetric profile of the frame, in two drawings, the sixth drawing 300d including a stent mesh and the seventh drawing 300e without the stent mesh. The sixth drawing 300d and the seventh drawing 300e show a different shape of the frame than other drawings of FIG. 3.

An eighth drawing 300h shows a fifth asymmetric profile of a fifth shape of the frame, including a stent mesh. The fifth asymmetric shape show a thinner profile of on one side 311 of the frame than on another side 312 of the frame. In some embodiments the thinner side 311 is intended for use on a left ventricular outflow tract (LVOT), so as to potentially push a natural mitral valve leaf less toward the LVOT.

The various shaped depicted in FIG. 3 share the potential features described with reference to FIG. 2B.

Reference is now made to FIGS. 4A, B, C, which are simplified line drawing illustrations of a cross section of a heart 400 and a heart valve prosthesis frame 405 located in the natural mitral valve according to an example embodiment of the invention.

FIG. 4A shows portions of the heart introduced in FIG. 1—the left atrium 401, the annulus portion 402, the left ventricle 403, the papillary muscle 404, the chordae 404, the mitral valve leaflet 406.

FIG. 2A also shows a bottom portion 403 of the natural heart valve, where a bottom portion of the frame, also termed an apple portion, is located.

FIG. 4A demonstrates benefits of a frame built with an asymmetric design, where an outer shape of the frame 405 on the LVOT 407 side of the left ventricle 403 extends less from a center of the frame 405 than an outer shape of the frame 405 on the non-LVOT 407 side of the left ventricle 403.

FIGS. 4B and 4C show two cross sectional views of the example frame 405. FIG. 4B is a cross-sectional view at 90 degrees to the cross-sectional view of FIG. 4C.

The direction of view of the cross-section shown in FIG. 4B shows the example frame 405 with a first bottom portion 409 wider relative to a second bottom portion 410 of the frame 405.

The direction of view of the cross-section shown in FIG. 4C shows the example frame 405 with both bottom portions 408 equally wide relative to a lumen of the frame 405.

Figure 5A:
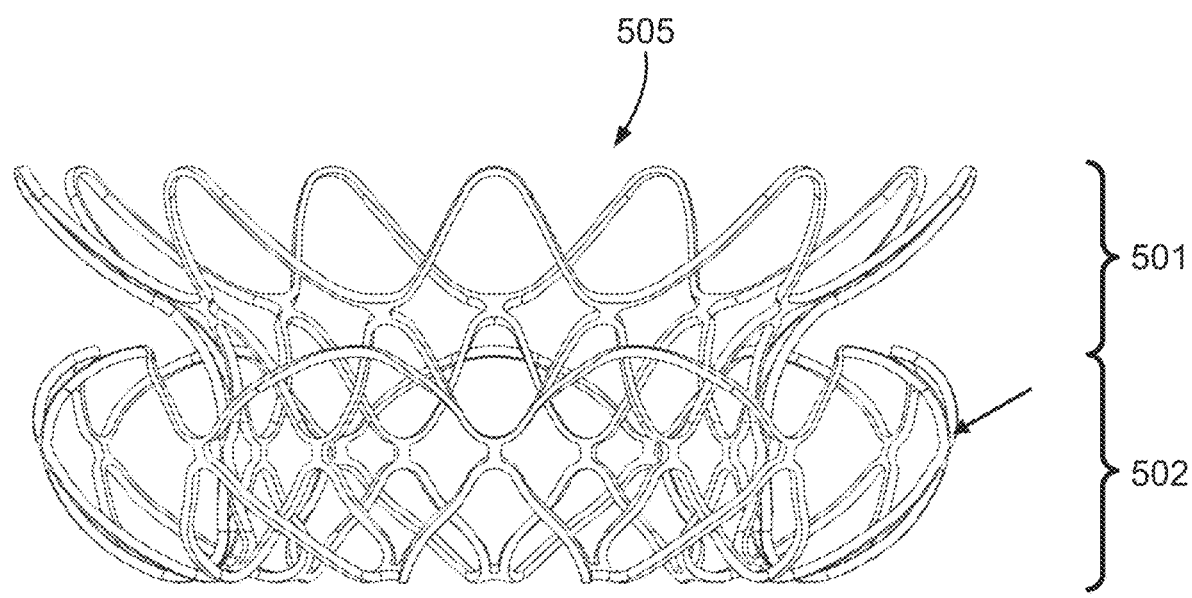
Figure 5B:
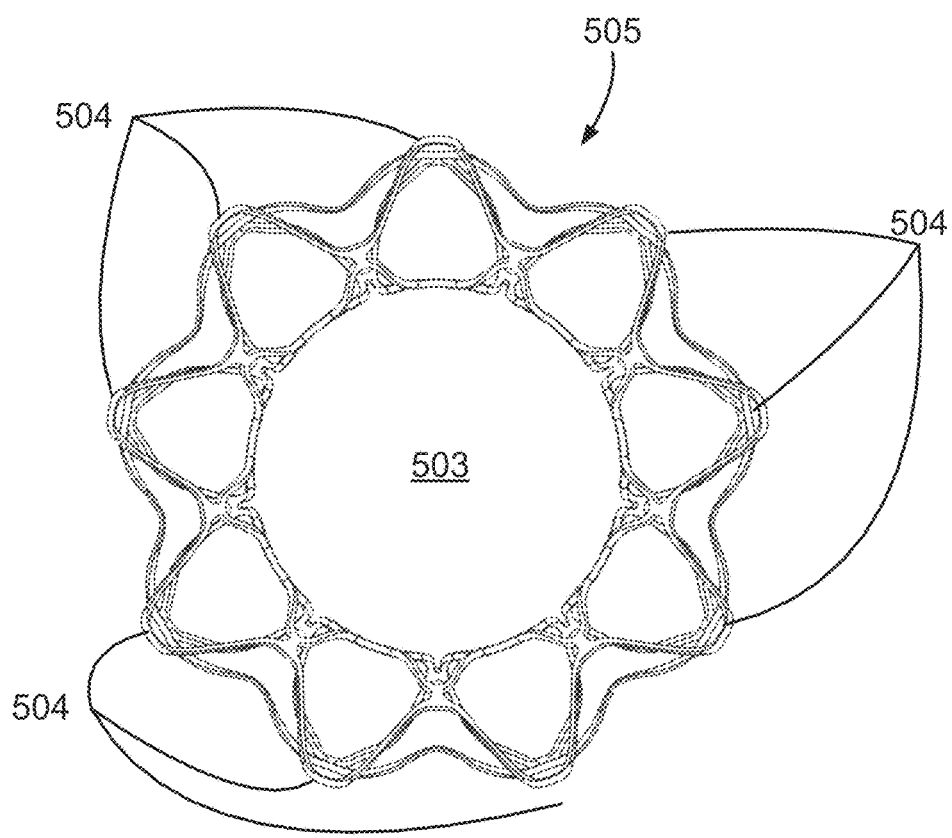

Reference is now made to FIGS. 5A and 5B, which are simplified line drawing illustrations of a heart valve prosthesis frame 505 according to an example embodiment of the invention.

FIG. 5A shows a side view of the heart valve prosthesis frame 505.

FIG. 5B shows a top view of the heart valve prosthesis frame 505.

FIG. 5A shows a top portion 501 of the frame 505 and a bottom portion 502 of the frame 505.

In some embodiments the outside shape of the frame 505 is similar to the outside shape shown in FIGS. 2A, 2B, 3, 4A and 4B.

In some embodiments an inside lumen of the frame 505 is round, as shown in FIG. 2B.

FIGS. 5A and 5B show the frame 505. FIG. 5B shows nine protruding arcs 504.

In some embodiments the number of protruding arcs 504 is a multiple of three.

In some embodiments the number of protruding arcs 504 may be three, six, nine, or twelve.

Reference is now made to FIGS. 6A-D, which are simplified line drawing illustrations of a heart valve prosthesis frame 605 according to an example embodiment of the invention.

FIG. 6A shows a side view of the heart valve prosthesis frame 605.

FIG. 6B shows a top view of the heart valve prosthesis frame 605.

FIG. 6C shows a side view of a cross section of an outside shape 608 of the heart valve prosthesis frame 605.

FIG. 6D shows a side view of a cross section of an outside shape 608 of the heart valve prosthesis frame 605 and a side view 610 of the heart valve prosthesis frame 605.

FIG. 6A shows a top portion 601 of the frame 605, also named the onion portion, and a bottom portion 604 of the frame 605, also named the apple portion. FIG. 6A also shows a narrow portion of the frame 605, designed to be placed at the natural heart valve annulus, and a top 603 of an arc included in the frame 605. In some embodiments the top 603 arc is directed in a direction which does not place the tip of the arc pressing on the natural annulus, rather lying parallel to the natural annulus, spreading a potential pressure of the frame 605.

In some embodiments, the bottom portion 604 of the frame 605 has a shape of a torus. The torus shape potentially provides one or more benefits such as:
 a top 603 of the arc is presented toward the frame 605 and not toward walls of the heart, and so does not provide a potential for wounding the walls of the heart;
 a cross section of the torus shape potentially spreads pressure back upstream against a valve placed in the frame across a number of arcs, each arc taking a part of the pressure, and each arc presenting a round, not sharp, shape against walls of the heart;
 a cross section of the torus shape potentially expands sideways under pressure back upstream, potentially improving a seal between the frame and the heart walls and/or between the frame and a valve placed in the frame; and
 the torus shape provides elastic pressure against side walls, potentially assisting a seal of the frame against walls of the heart, especially when at least some of the frame is covered by a flexible sheet which assists sealing.

FIG. 6B shows a center lumen 606 of the frame 605, and an outer circumference 607 of the frame 605. In the example embodiment of FIGS. 6A-D the center lumen 606 of the frame 605 is shaped as a circle.

FIGS. 6A-D show a symmetric frame 605, in which the outer circumference 607 of the frame 605 is shaped as a circle.

In some embodiments, the center lumen 606 of the frame 605 is shaped as a circle.

In some embodiments, the frame 605 includes a valve constructed of one or more flexible sheets attached or sewn directly to the frame 605. In some embodiments, the bottom portion 604, which includes two layers of frame between a center of the lumen of the frame 605 and an outside circumference of the frame 605. The two layers provide more resistance against sideways pressure than a single layer would.

In some embodiments, the bottom portion 604, also named the apple portion, has a cross section profile shaped as a major portion of a circle. Such a circular profile potentially provides elastic resistance to back pressure against a closed valve, such as will occur every time the left ventricle contracts and an artificial mitral valve is closed.

Figure 7A:
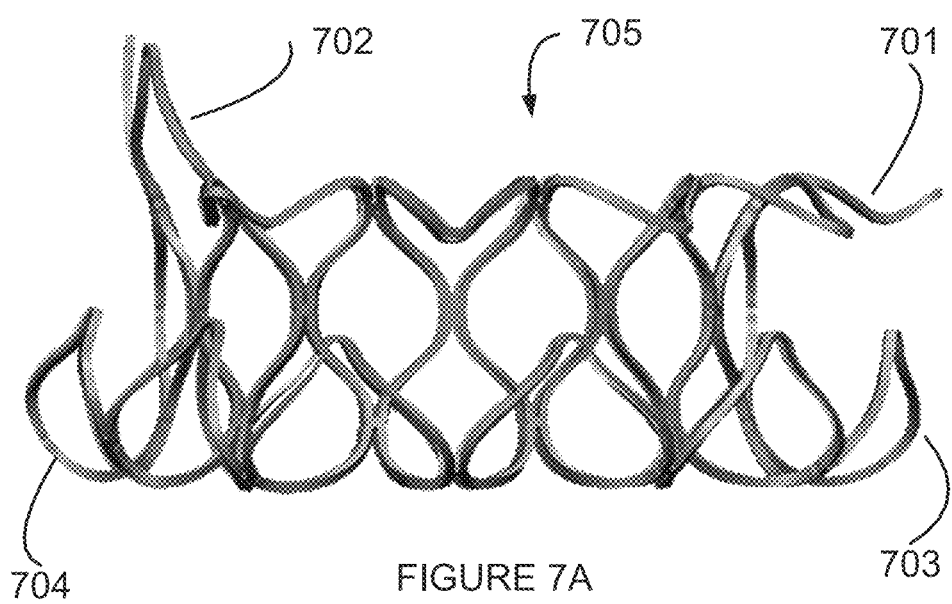
Figure 7B:
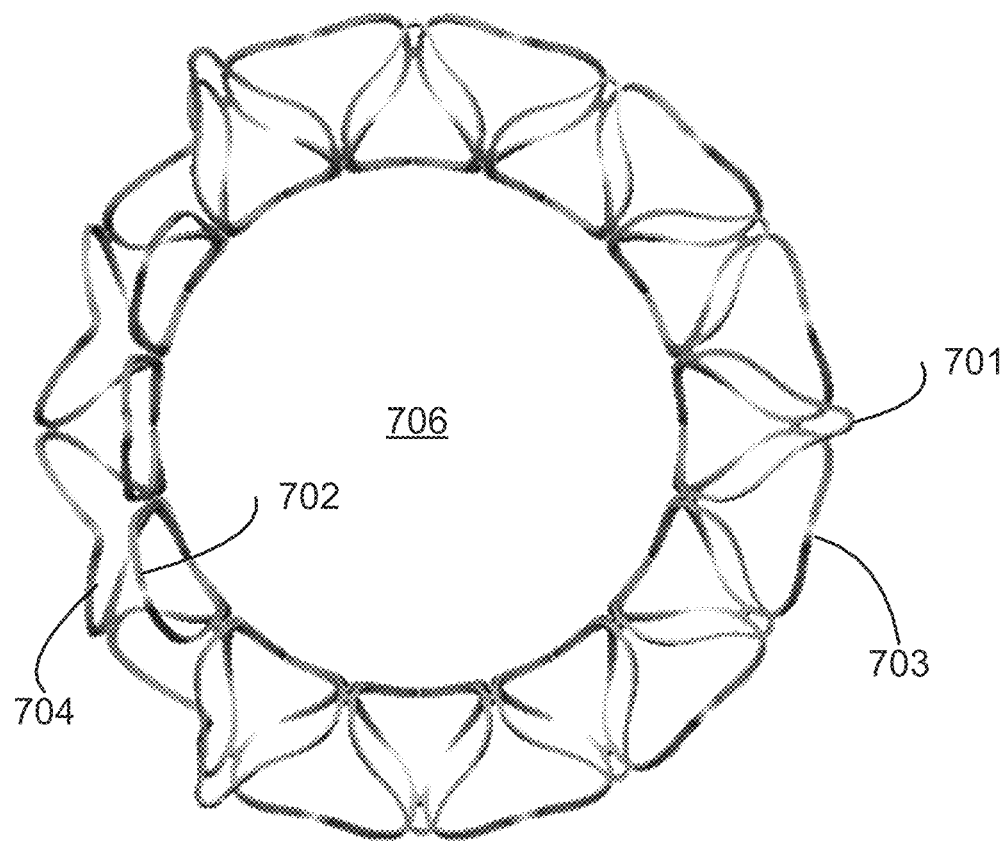
Figure 7C:
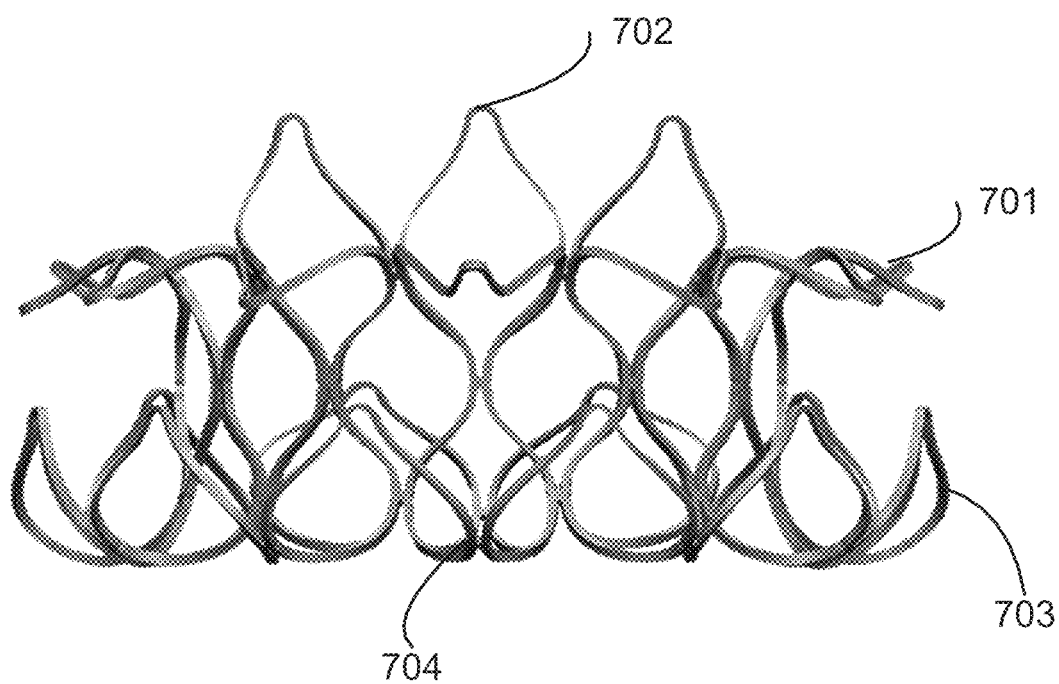

Reference is now made to FIGS. 7A-C, which are simplified line drawing illustrations of a heart valve prosthesis frame 705 according to an example embodiment of the invention.

FIG. 7A shows a side view of the heart valve prosthesis frame 705.

FIG. 7B shows a top view of the heart valve prosthesis frame 705, and a center lumen 706 of the frame 705. In the example embodiment of FIGS. 7A and 7B the center lumen 706 of the frame 705 is shaped as a circle.

FIG. 7C shows a side view of the heart valve prosthesis frame 705.

FIGS. 7A-C show an asymmetrical frame 705, with an LVOT side less protruding from a center of the lumen 706 than a non-LVOT side.

FIGS. 7A-C show a shape of a top portion 702 and of a bottom portion 704 of the frame 705 on an LVOT side of the frame 705, and of a top portion 701 and of a bottom portion 703 on a non-LVOT side of the frame 705.

The LVOT side juts out less from a center of the lumen 706 of the frame 705. By jutting less, the LVOT side potentially pushes less on a natural mitral valve anterior leaflet, refraining from pushing the natural mitral valve anterior leaflet into the LVOT, potentially reducing or refraining from interfering with LVOT blood flow, a condition called LVOT obstruction.

FIGS. 7A and 7B show that an area of the frame 705, for example as viewed in the top view of FIG. 7B, is relatively large when compared to an area of the center lumen 706.

In some embodiments, the area of the center lumen 706 is in a range corresponding to a diameter D1 in a range of 25 millimeters to 35 millimeters, which area is $\pi(D1/2)^2$, in a range of approximately 490 square millimeters to 960 square millimeters.

In some embodiments, the area of the center lumen 706 is smaller than a natural annulus of a healthy human patient.

In some embodiments, the area of the center lumen 706 is larger than an annulus of a human patient suffering from a shrinking of the annulus.

In some embodiments, the area of the frame 705, including the center lumen 706, is in a range corresponding to a diameter D2 in a range of 45 millimeters to 55 millimeters, which area is $\pi(D2/2)^2$, in a range of approximately 1590 square millimeters to 2375 square millimeters.

The area of the lumen 706 represents an area which is mostly dedicated to passage of blood. The area of the lumen 706 also represents an area upon which blood will exert pressure when the valve prosthesis is closed. The area of the frame 705 represents an area which will press against the natural heart and anchor the valve prosthesis from shifting away from its location in the natural valve annulus. A favorable ratio of the area of the frame 705 to the area of the lumen 706, such as in a range of 0.3 to 0.4 potentially spreads out the pressure of the frame against the natural heart, and potentially causes less localized pressure, which might wound the natural heart.

Figure 8:
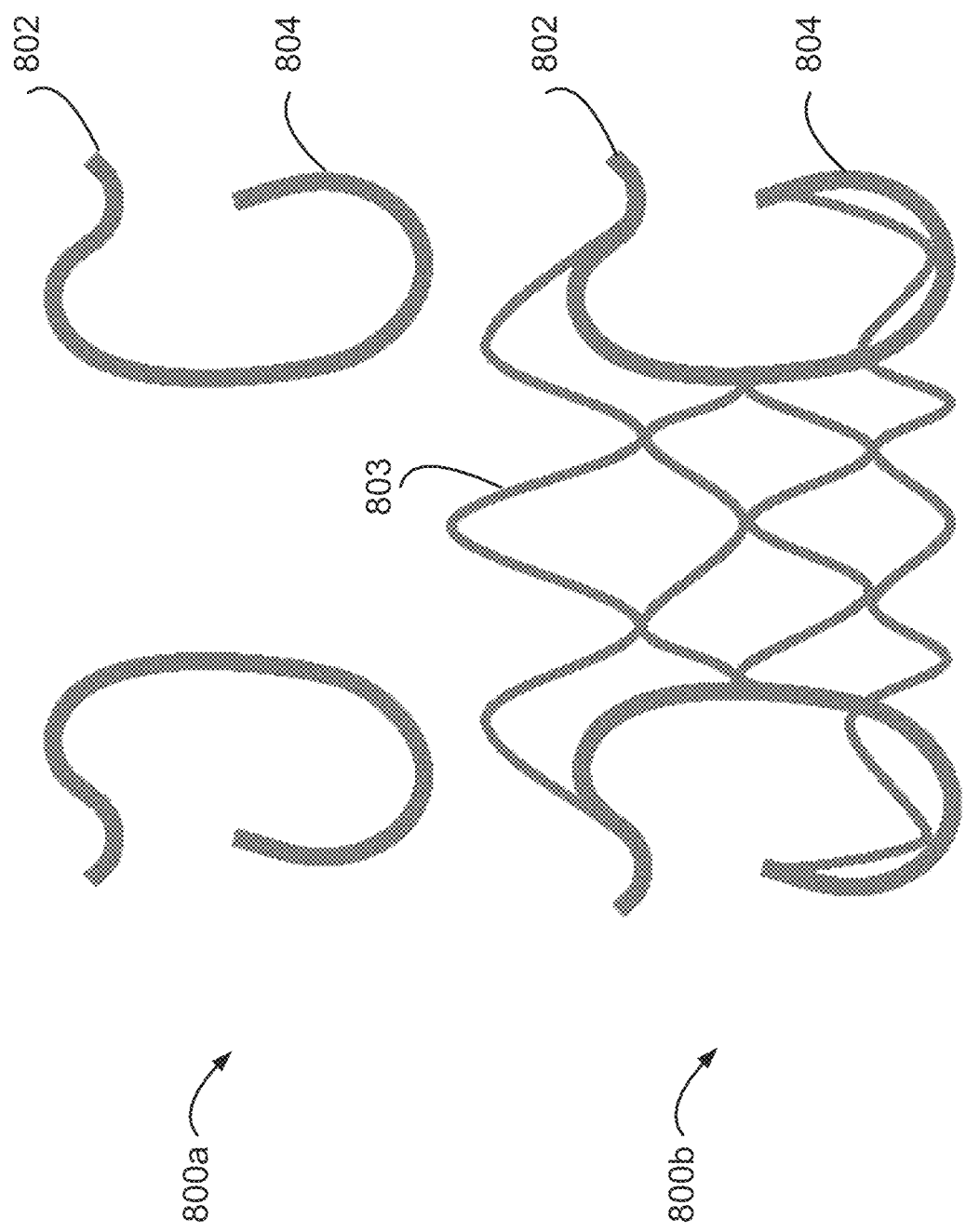

Reference is now made to FIG. 8 which is a set of simplified line drawing illustrations of a cross section of a heart valve prosthesis frame according to an example embodiment of the invention.

FIG. 8 shows two drawings 800a 800b of a non-limiting example shape of a cross section of the frame of FIG. 8. Attention is directed to a profile of an outside shape of the drawings 800a 800b.

A first drawing 800a shows the symmetric profile of the frame without showing a stent mesh. A second drawing 800b shows the symmetric profile of a shape of the frame, including a side view 803 of the frame.

A top portion 802 of the frame juts out from a center of a lumen of the frame so as to prevent the frame from falling through an annulus of the natural heart valve.

A bottom portion 804 of the frame juts out from a center of a lumen of the frame so as to prevent the frame from backing upstream through an annulus of the natural heart valve.

Figure 9:
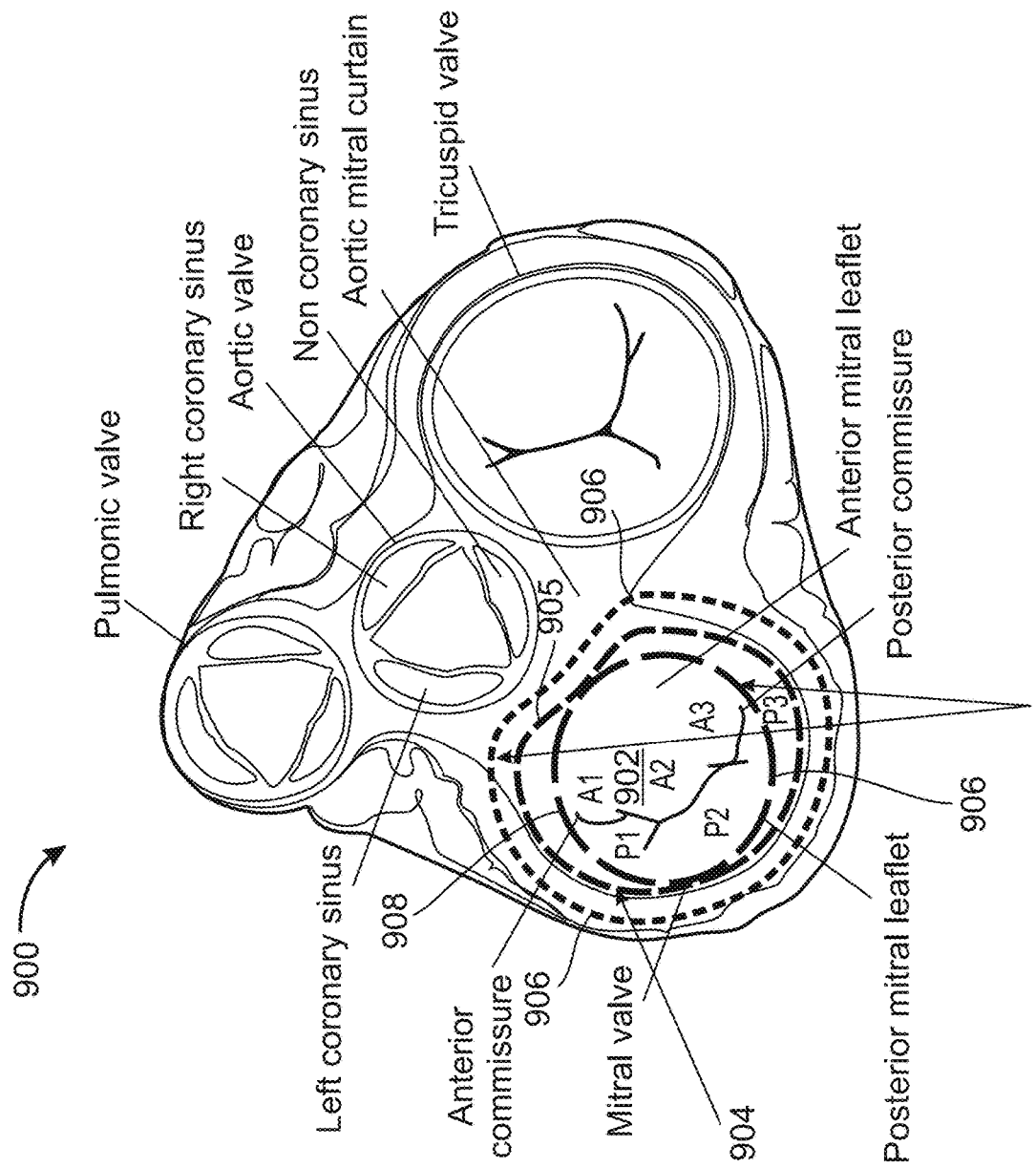

Reference is now made to FIG. 9, which is a simplified horizontal cross section of a heart 900 with specific lines showing lines of interest in a mitral valve 902 according to an example embodiment of the invention.

FIG. 9 show various anatomical features of a heart, which are well known.

FIG. 9 shows a first line, which marks a perimeter 904 of a typical natural mitral valve annulus. A shape of the first line marking the perimeter 904 of the typical mitral valve annulus is flattened on a side 905 close to the aortic valve, a shape also sometimes termed a D shape.

FIG. 9 shows a second line, which marks an outer perimeter 906 of a frame of a heart valve prosthesis according to an example embodiment of the invention. The outer perimeter of the frame of the example embodiment is outside of the perimeter 904 of the typical natural mitral valve annulus, so that the frame finds support on the natural mitral valve annulus when pressed against the annulus by pressure of blood on the frame and/or an artificial valve attached to the frame.

FIG. 9 shows a third line, which marks an inner perimeter 908 of the frame of a heart valve prosthesis according to an example embodiment of the invention. The inner perimeter of the frame of the example embodiment is inside the perimeter 904 of the typical natural mitral valve annulus, so that an artificial valve attached to the frame takes over a major portion of the perimeter 904, so does not obstruct blood flow through the annulus.

Reference is now made to FIGS. 10A-10D, which are images of a heart valve prosthesis 1000 constructed according to an example embodiment of the invention.

Figure 10C:
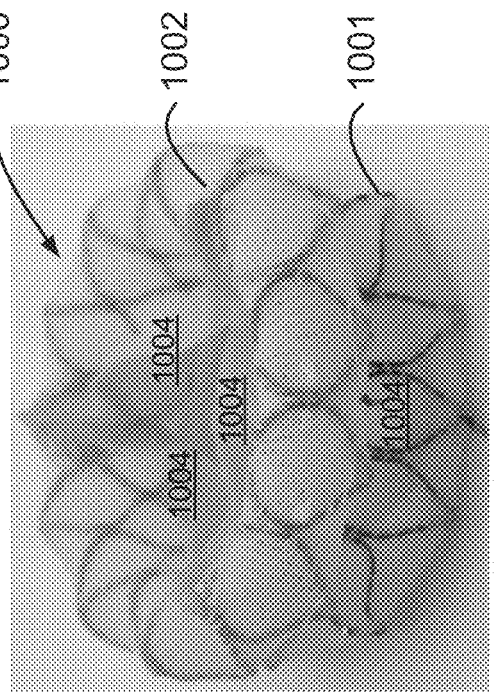
Figure 10D:
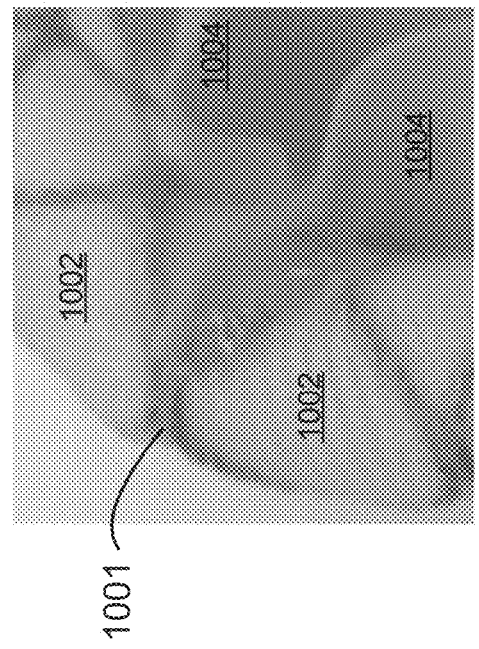
Figure 10A:
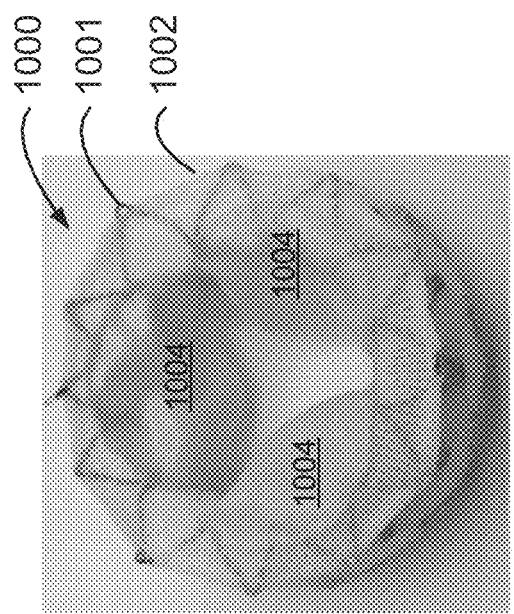

FIG. 10A is a top isometric view of the heart valve prosthesis 1000.

Figure 10B:
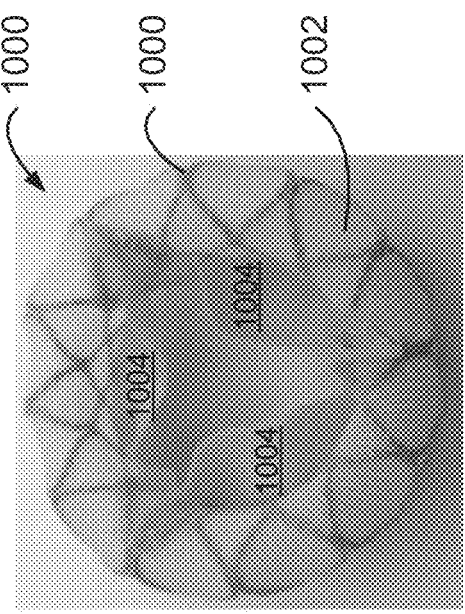

FIG. 10B is a bottom view of the heart valve prosthesis 1000.

FIG. 10C is a bottom isometric view of the heart valve prosthesis 1000.

FIG. 10D is a magnified top view of a portion of the heart valve prosthesis 1000.

FIGS. 10A-D shows an example embodiment of a frame 1001, which may be any of the example embodiments frames described herein, to which are attached: an outer sheet 1002 for sealing an outer perimeter of the heart valve prosthesis 1000 to a heart in which the heart valve prosthesis 1000 is located; and artificial leaflets 1004 which act as an artificial heart valve.

FIG. 10D shows a magnified view of a portion of the heart valve prosthesis 1000, which shows stitching of the leaflets 1004 to the frame 1001 and the outer sheet 1002 to the frame 1001.

Figure 11:
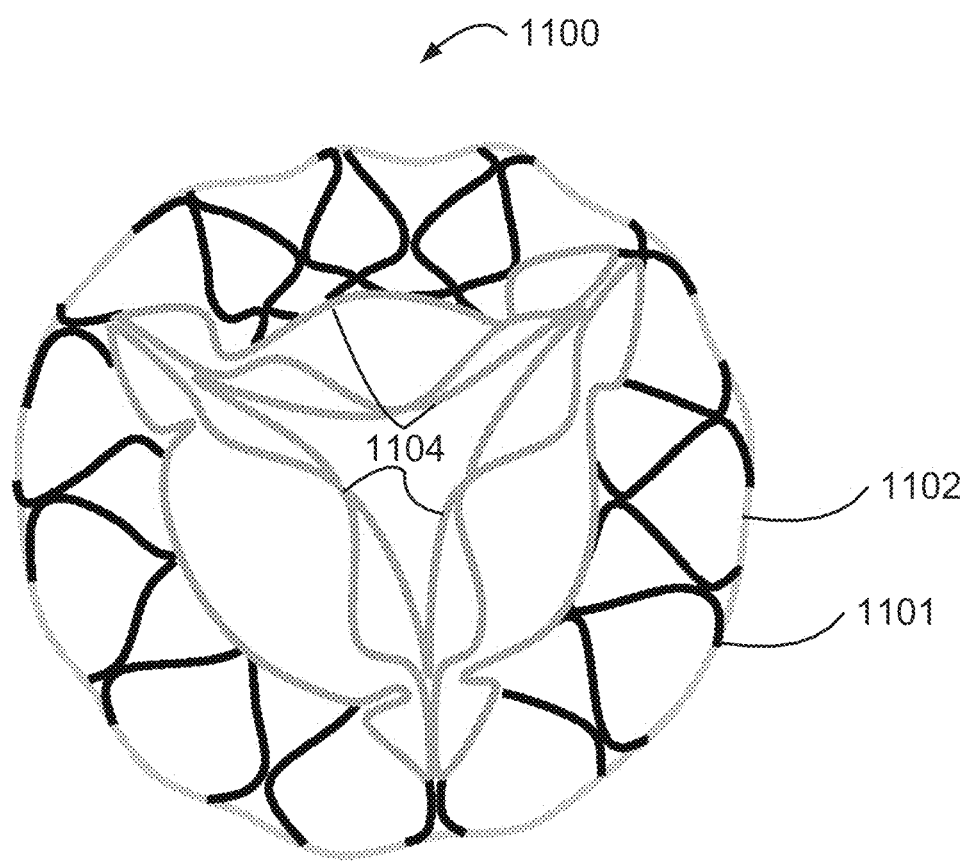

Reference is now made to FIG. 11, which is a simplified line drawing of a top view of a heart valve prosthesis 1100 constructed according to an example embodiment of the invention.

FIG. 11 shows an example embodiment of a frame 1101, which may be any of the example embodiments frames described herein, to which are attached: an outer sheet 1102 for sealing an outer perimeter of the heart valve prosthesis 1100 to a heart in which the heart valve prosthesis 1100 is located; and artificial leaflets 1104 which act as an artificial heart valve.

Reference is now made to FIG. 12A, which is a simplified line drawing illustration of an internal frame 1201 for supporting an artificial heart valve constructed according to an example embodiment of the invention.

FIG. 12A shows an internal frame 1201, to which may be sewn an artificial flexible sheet valve as shown in FIGS. 10A-D and 11. In some embodiments the internal frame 1201 includes one or more wire frames 1204 attached to supports 1202.

In some embodiments the wire frame(s) 1204 includes wire frames arcs 1203, each one of the wire frame arcs 1203 having a top 1205 of the arc 1203.

Reference is now made to FIG. 12B, which is a simplified line drawing illustration of an external frame 1210 for supporting an heart valve prosthesis constructed according to an example embodiment of the invention.

FIG. 12B shows an external frame 1210, which may be shaped according to various frame shapes depicted herein, by way of some non-limiting examples, in FIGS. 2A-B, 3, 4A-B, 5A-B, 6A-D, 7A-C, 8, 10A-D and 11.

In some embodiments the external frame 1210 includes an upper portion 1212, also termed an onion portion, and a lower portion 1214, also termed an apple portion.

Reference is now made to FIG. 12C, which is a simplified line drawing illustration of a frame 1220 including an internal frame 1201 attached to an external frame 1210 according to an example embodiment of the invention.

In some embodiments the internal frame 1201 is attached to the external frame 1210 at internal frame supports 1202 also shown in FIG. 12A.

Reference is now made to FIGS. 13A-E, which are simplified line drawing illustrations of a heart valve prosthesis 1300 including an external frame attached to an internal frame and to an artificial heart valve, constructed according to an example embodiment of the invention.

Figure 13A:
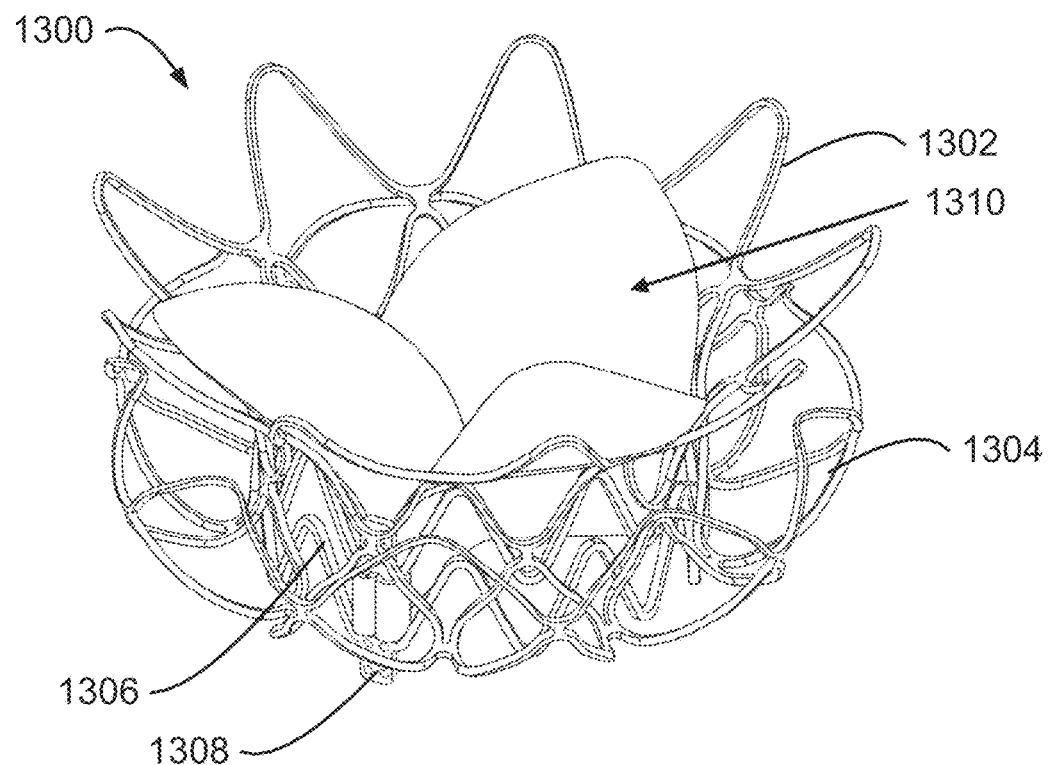
Figure 13B:
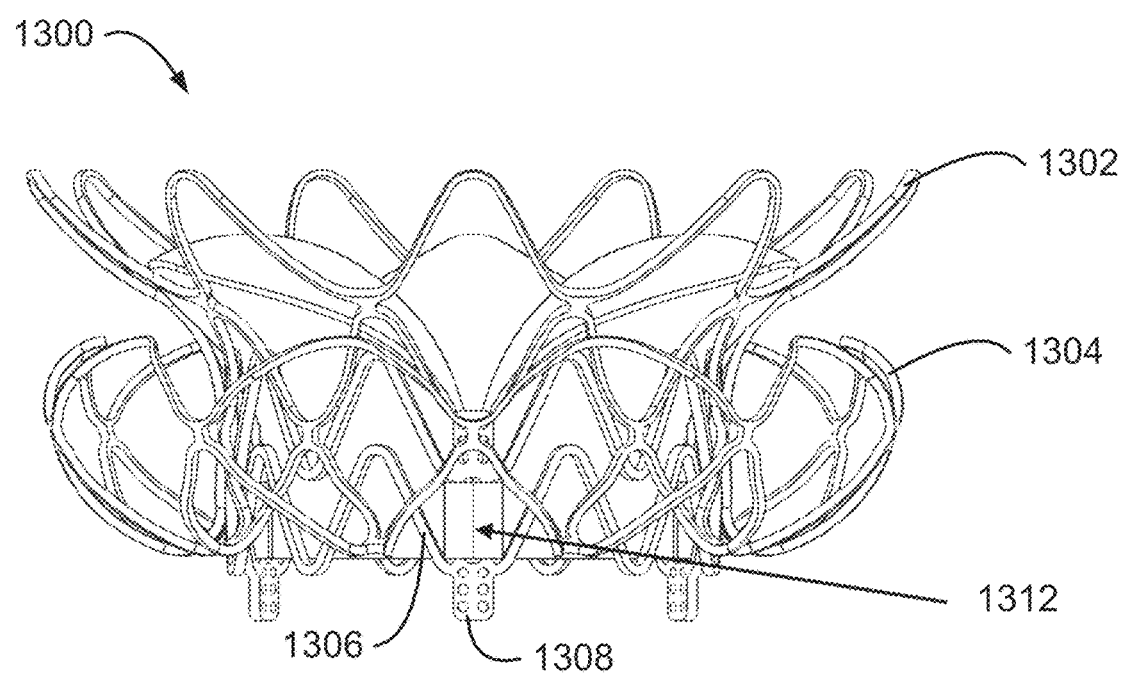
Figure 13C:
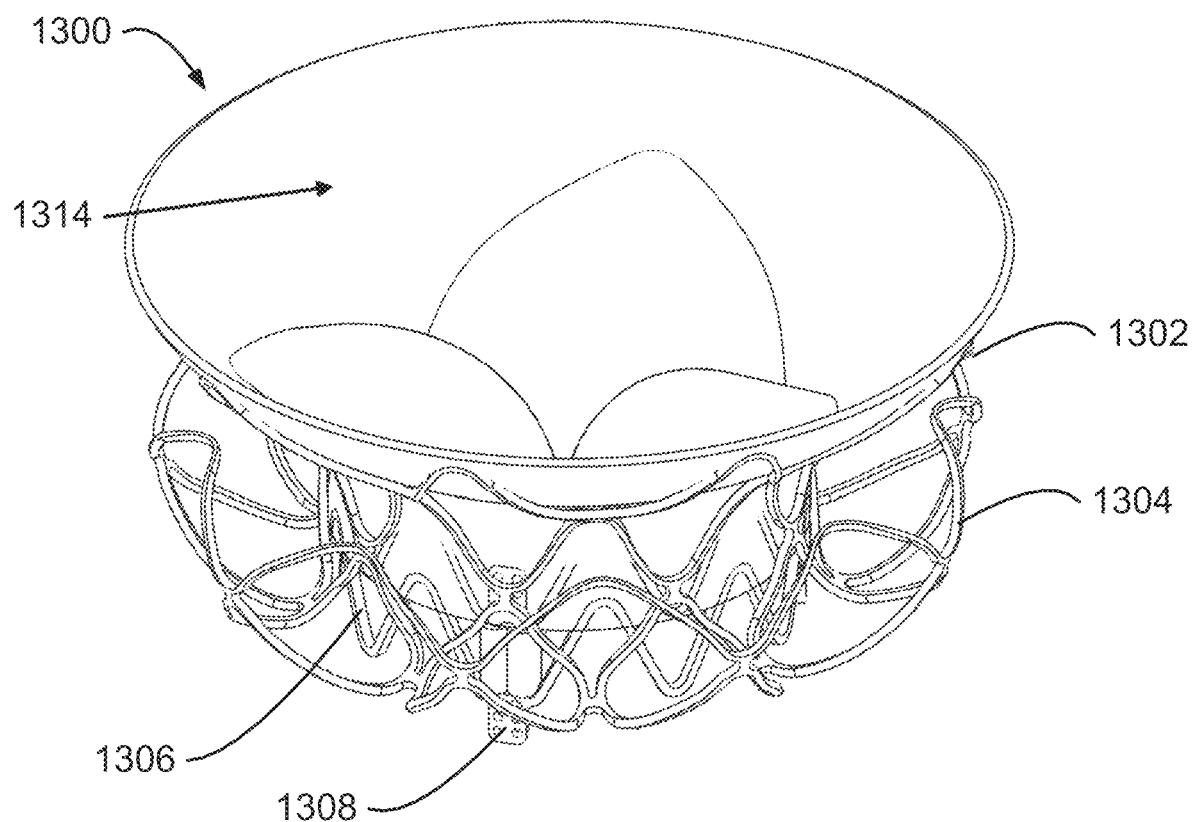
Figures 13D, 13E:
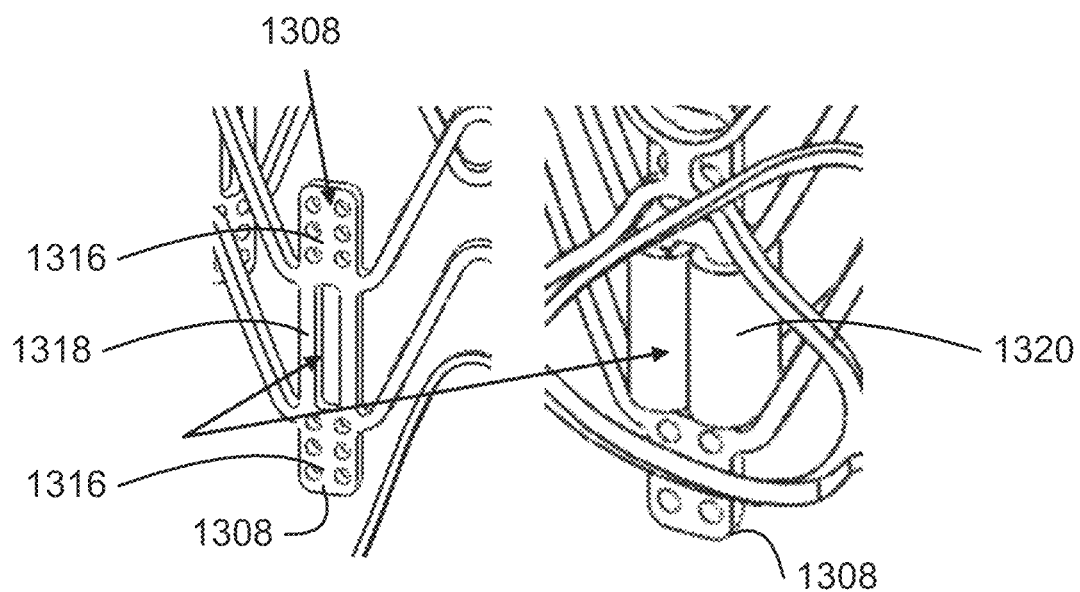

FIG. 13A is an isometric top view, FIG. 13B is a side view, FIG. 13C is an isometric top view, and FIGS. 13D and 13E are magnified detailed views, of the example embodiment of FIGS. 13A and 13B.

FIGS. 13A and 13B show a top portion 1302 and a bottom portion 1304 of an external frame; an internal frame 1306 and internal frame supports 1308; and leaflets 1310 of an artificial heart valve.

FIG. 13C also shows a fabric 1314 for sealing the heart valve prosthesis along an outer perimeter of the heart valve prosthesis.

In some embodiments, attaching the internal frame and the external frame may be done by any one of suturing, crimping, soldering and/or welding.

In some embodiments, the internal frame supports 1308 include holes, as shown in FIGS. 13B and 13D, which may or may not be used for suturing.

In some embodiments, the internal frame is attached to the external frame by crimping the internal frame support 1308 to the external frame using a crimp 1312, as shown in FIGS. 13B and 13D.

FIG. 13D shows an internal frame support 1308 including optional holes 1316, which may optionally be used to suture the internal frame to the external frame.

FIG. 13D shows an internal frame support 1308 including and optional slit 1318, which may optionally be used to accept a crimping component 1320, as shown in FIG. 13E, for crimping the internal frame to the external frame.

Reference is now made to FIGS. 14A-C, which are simplified line drawing illustrations of components of a heart valve prosthesis 1400 according to an example embodiment of the invention.

FIGS. 14A-C show a top portion 1404 and a bottom portion 1406 of an external frame; an internal frame 1402 and internal frame supports 1403.

FIG. 14A shows the internal frame 1402 separate from the external frame.

FIG. 14B shows the internal frame 1402 separate from the external frame, and also show a fabric 1408 for sealing the heart valve prosthesis. In some embodiments the fabric 1408 may optionally be selected so as to enable tissue growth and additional sealing when the heart valve prosthesis 1400 is implanted in place.

FIG. 14C shows the internal frame 1402 within the external frame, in a correct position, as designed for implanting in place in a natural heart valve.

Reference is now made to FIGS. 15A and 15B, which are simplified line drawing illustrations of a heart valve prosthesis 1500 constructed according to an example embodiment of the invention.

FIG. 15A is a top view and FIG. 15B is an isometric bottom view, of the example embodiment of FIGS. 15A and 15B.

FIGS. 15A and 15B show an embodiment using a single frame, unlike two-part (internal and external) framed shown in other Figures, with reference to other embodiments.

FIGS. 15A and 15B show a heart valve prosthesis including a top portion 1502 and a bottom portion 1504 of a frame; frame supports 1506; and leaflets 1508 of an artificial heart valve.

In some embodiments the leaflets shown in FIGS. 15A and 15B are optionally sutured to the single frame.

In some embodiments the frame of the heart valve prosthesis includes wire arcs, in the top portion 1502 of the frame and/or in the bottom portion 1504 of the frame. In some embodiments a number of wire arcs in the top portion 1502 and/or in the bottom portion 1504 of the frame is a multiple of three.

In some embodiments a number of wire arcs in the top portion 1502 and/or in the bottom portion 1504 of the frame is nine, as shown in FIG. 15A.

In some embodiments the heart valve prosthesis optionally includes three leaflets, as shown in FIGS. 15A and 15B.

In some embodiments the heart valve prosthesis optionally includes a number of leaflets which is a multiple of three.

Reference is now made to FIGS. 16A-D, which are simplified line drawing illustrations of a side view cross section of a frame 1600 of a heart valve prosthesis being released from a compressed shape and expanding according to an example embodiment of the invention.

Figures 16A, 16B, 16C, 16D:
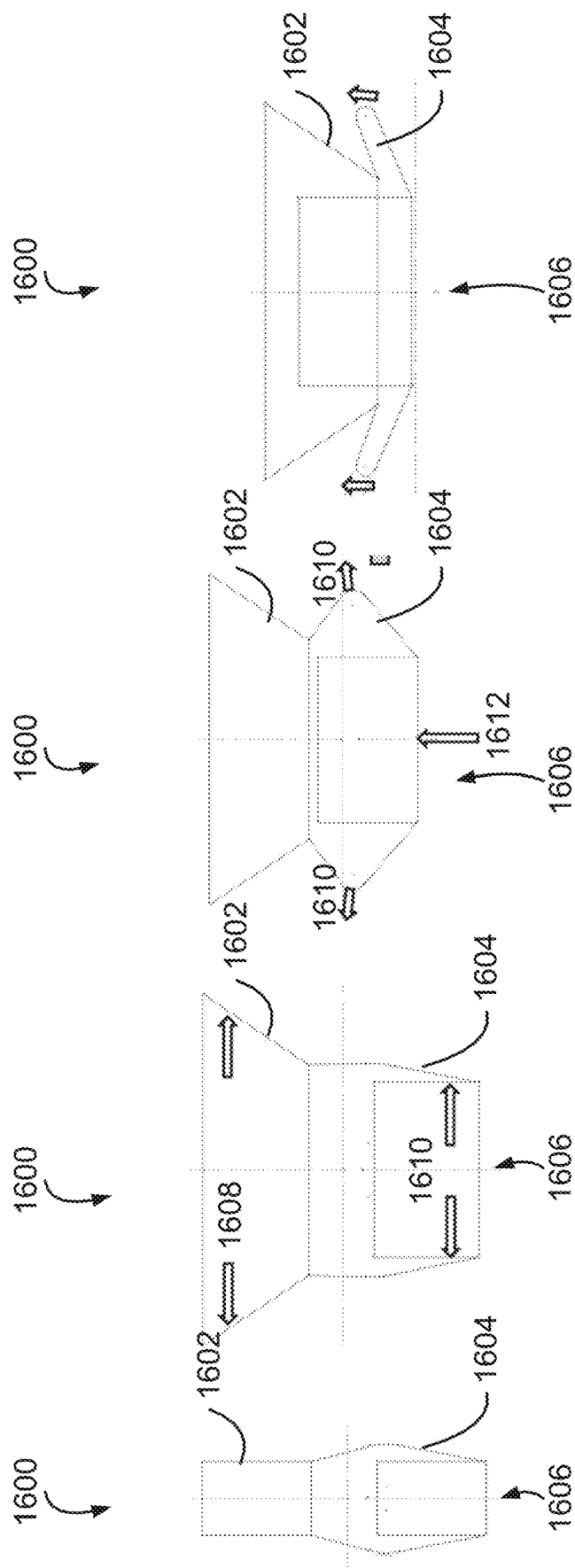

FIG. 16A shows the frame 1600 in a compressed shape, as may be, for example, in a catheter designed for insertion into a patient's body. FIG. 16A shows an upper portion 1602 of the frame 1600, a lower portion 1604 of the frame 1600, and points out a lumen 1606 through the frame 1600.

The frame 1600 is optionally shaped as a single walled tube shape. A single walled tube may be compressed and inserted into a narrower gauge catheter than, for example, a double walled tube.

In some embodiments, the frame 1600 is optionally designed to fit into a channel in a catheter of an outside diameter of 8 millimeters, also termed French gauge 24. Enabling a frame 1600 to fit within a catheter potentially enables implanting heart valve prostheses via catheter instead of via open-heart surgery.

In some embodiments, the frame 1600 is optionally designed to fit into a channel in a catheter of an outside diameter of French gauge 26, 28 or 30, or above.

The frame 1600 is optionally constructed from shape-memory material, which is optionally inserted into a patient's body in one shape, and the frame 1600 optionally reshapes into a second shape when released within the body. In some embodiments the frame 1600 is optionally constructed of Nitinol.

The frame 1600 is optionally constructed from a biocompatible material.

The frame 1600 is optionally constructed from Nitinol or cobalt chrome.

FIG. 16B shows the frame 1600 starting to decompress, as may be, for example, when released from a catheter within the patient's body. FIG. 16B shows a first expansion force 1608 acting on the upper portion 1602, and a second expansion force 1610 acting on the lower portion 1604.

The frame 1600 optionally expands, reshaping to a shape as shown in FIG. 16B.

FIG. 16C shows the frame 1600 continuing to decompress. FIG. 16C shows the second expansion force 1610 continuing to act on the lower portion 1604. The lower portion 1604 is compressed in length in a direction 1612, to enable a widening of the lower portion 1604.

FIG. 16D shows the frame 1600 continuing to decompress. FIG. 16D shows the lower portion 1604 everting, that is turning inside out, as part of a continuing reshaping of the lower portion 1604.

In some embodiments the shape of the frame 1600 is a shape used for anchoring the frame 1600 in a location of the natural heart valve, optionally the lower portion 1604 anchored to a sub-annulus region of the natural heart valve.

In some embodiments the eversion of the lower portion 1604 produces a shape as depicted in FIG. 16D, with the lower portion pointing in an upstream direction, relative to a direction of blood flow.

In some embodiments the upstream pointing lower portion 1604 potentially provides spring-like resistance to upstream pressure.

In some embodiments the upstream pointing lower portion 1604 potentially traps natural heart valve leaflets, potentially preventing sideways movement of the natural heart valve leaflets, which might interfere with blood flow, for example in the LVOT.

In various embodiments, the frame shapes and/or profiles shown in FIGS. 3, 4A-B, 5A-B, 6A-D, 7A-C, 8, 10A-D and 11 can be inserted via a catheter as a single walled tube, and released from the catheter to expand into their memorized shape.

Reference is now made to FIGS. 17A-D, which are simplified line drawing illustrations of a frame 1700 according to an example embodiment of the invention.

The example embodiment frame 1700 of FIGS. 17A-D is a non-limiting example of a single-frame embodiment suitable for insertion and expansion as shown in FIGS. 16A-D.

Figure 17A:
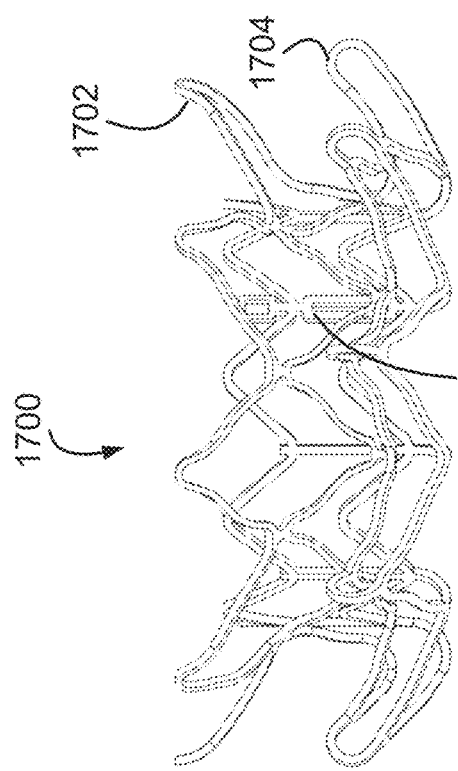
Figure 17C:
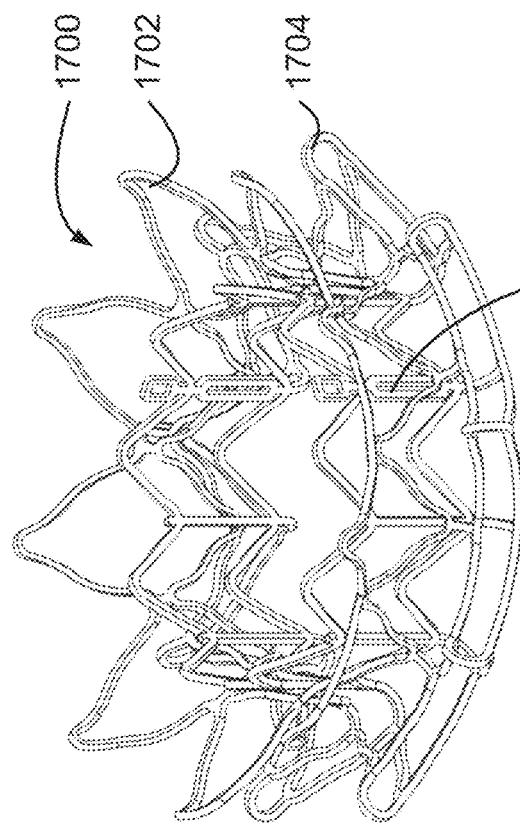
Figure 17B:
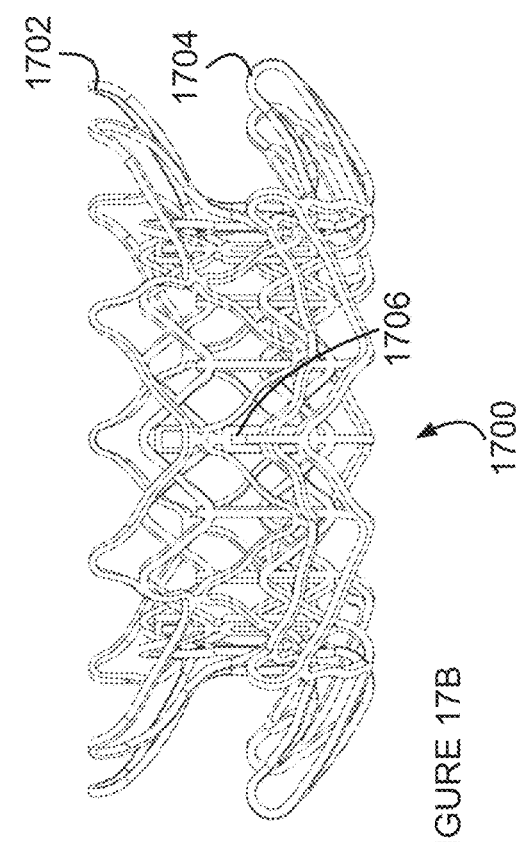
Figure 17D:
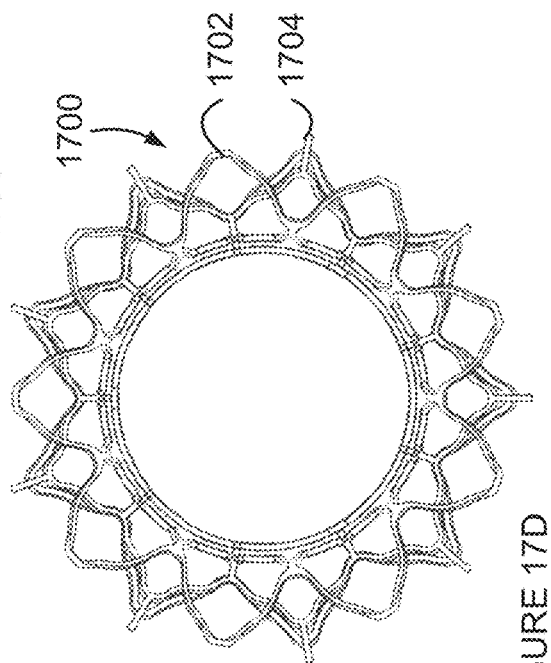

FIG. 17A is a first side view of the frame 1700, FIG. 17B is a second side view of the frame 1700, FIG. 17C is an isometric top view of the frame 1700, and FIG. 17D is a top view of the frame 1700.

FIGS. 17A-D show a top portion 1702 and a bottom portion 1704 of the frame 1700.

FIGS. 17A-C also show supports 1706 which may optionally be used to attach flexible sheet leaflets (not shown), optionally including slits in the supports 1706.

Reference is now made to FIGS. 18A-D, which are simplified line drawing illustrations of a frame 1800 according to an example embodiment of the invention.

The example embodiment frame 1800 of FIGS. 18A-D is a non-limiting example of a single-frame embodiment, and also a non-limiting example of an internal frame as shown in some of the Figures herein.

The example embodiment frame 1800 of FIGS. 18A-D shows wire arcs 1805 in a bottom portion 1804 which can optionally trap or grip folds of a natural heart valve leaflet.

Figure 18D:
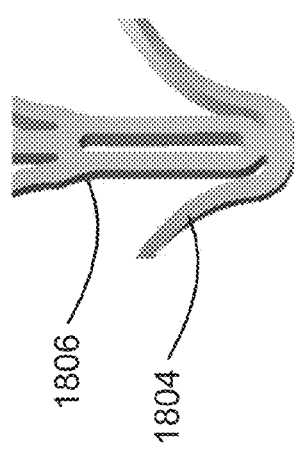
Figure 18C:
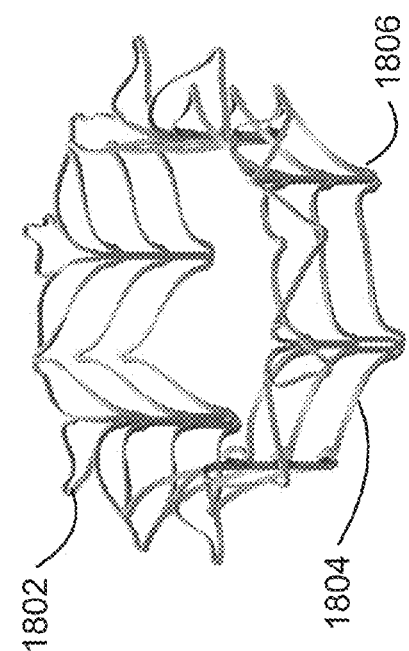
Figure 18A:
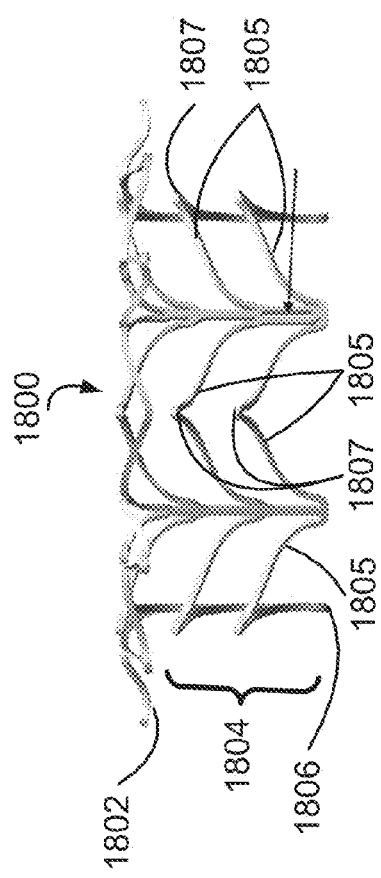
Figure 18B:
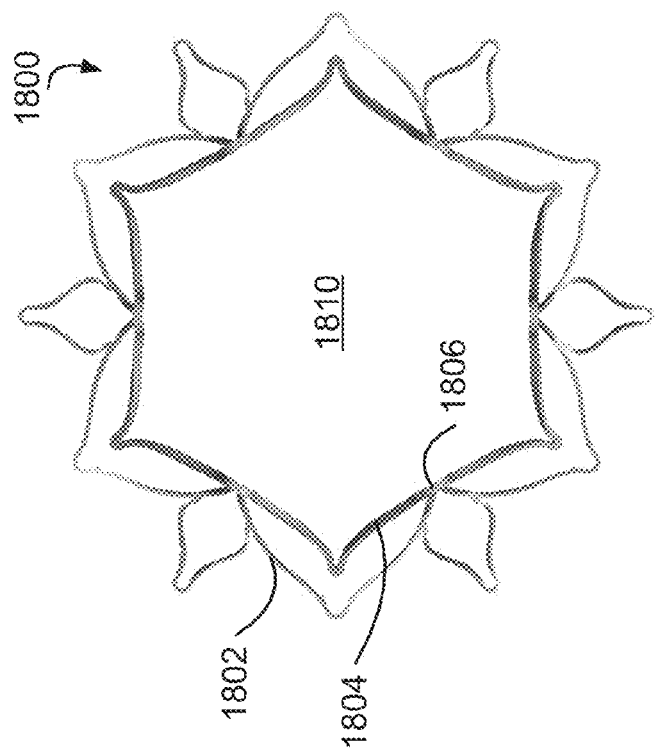

FIG. 18A is a side view of the frame 1800, FIG. 18B is a top view of the frame 1800, FIG. 18C is an isometric top view of the frame 1800, and FIG. 18D is a magnified view of a portion of the frame 1800.

FIGS. 18A-D also show supports 1806 which may optionally be used to attach flexible sheet leaflets (not shown), optionally including slits in the supports 1806.

The example embodiment frame 1800 of FIGS. 18A-D shows wire arcs 1805 arranged as at least two rings, each ring circumnavigating the center lumen of the frame. In some embodiments more than two rings are included, such as three rings, four rings and five rings.

The example embodiment frame 1800 of FIGS. 18A-D shows wire arcs 1805 in a bottom portion 1804 which can optionally trap or grip folds of a natural heart valve leaflet, which can potentially provide one or more of the following benefits:

sealing against blood flow around the frame 1800;
anchoring the frame 1800 to the natural heart valve leaflets; and
preventing the natural heart valve leaflets from moving to block blood flow in the LVOT.

The top view of FIG. 18B shows that a central lumen 1810 in the frame 1800 may be a non-circle shape.

The views of FIGS. 18A and 18C show two rows of wire arcs 1805. It is noted that variations on the number of rows of arcs are contemplated, such a single arc, three arcs, four arcs, and additional arc counts such as five, six, seven, eight, nine and ten.

In some embodiments a distance between the rows of the wire arcs 1805 is designed so as to leave enough distance between the rows of the wire arcs 1805 to allow a natural leaflet to pass between the rows of the wire arcs 1805.

In some embodiments a distance between the rows of the wire arcs 1805 is in a range of 2 mm to 8 mm.

In some embodiments the rows of the wire arcs 1805 are arranged as rows of zigzag shaped wire arcs, rather than, by way of a non-limiting example, a typical stent with rhomboid shaped openings.

In some embodiments, the wire arcs 1805 are connected to the supports 1806 and not directly to each other, leaving a space through which a leaflet may pass and be clamped or pinched.

In some embodiments a tip of the wire arc 1805 has a bend 1807, to continue the zigzag shape of the wire arc 1805. In some embodiments the bend 1807 is round, not sharp, thereby potentially preventing damage to heart walls.

In some embodiments a tip of the wire arc 1805 includes outward facing teeth (not shown), to prevent the frame 1800 from slipping along heart walls, the annulus, or the leaflets.

Reference is now made to FIGS. 19A and 19B, which are images of a heart valve prosthesis 1900 according to an example embodiment of the invention.

The images of FIGS. 19A and 19B are images of an example embodiment as shown in FIGS. 18A-D.

FIG. 19A is a bottom isometric view of the heart valve prosthesis 1900, and FIG. 19B is a top view of the heart valve prosthesis 1900.

The example embodiment frame 1900 of FIGS. 19A and 19B shows:

a top portion 1903;
wire arcs 1904 which can optionally trap or grip folds of a natural heart valve leaflet;
a sheet of material 1905, optionally fabric, for sealing an outside of the heart valve prosthesis 1900 against the natural heart;
supports 1906 attached to the wire arcs 1904; and
artificial leaflets 1907 forming an artificial valve.

Reference is now made to FIG. 20A, which is a simplified line drawing of a heart valve prosthesis frame 2000 according to an example embodiment of the invention.

FIG. 20A shows how a natural heart valve leaflet, or a natural heart valve annulus, may be pinched and/or held by the frame 2000.

FIG. 20A shows: a top portion 2001 of the frame 2000; wire arcs 2002 of a bottom portion of the frame 2000; and supports 2003 attached to the wire arcs 2002.

FIG. 20A shows what a side view cross section of a natural heart valve annulus 2006 look like when optionally trapped and/or pinched between the wire arcs 2002 of the frame 2000.

FIG. 20A shows what a side view cross section of natural heart valve leaflets and/or ventricular wall tissue 2005 look like when optionally trapped and/or pinched between the wire arcs 2002 of the frame 2000.

In some embodiments a fold of the natural heart valve leaflets 2005 and/or the natural heart valve annulus 2006 may optionally be caught between the top portion 2001 of the frame 2000 and the wire arcs 2002, as shown in FIG. 20A.

In some embodiments a fold of the natural heart valve leaflets 2005 or the natural heart valve annulus 2006 may optionally be caught between different rows of the wire arcs 2002.

In some embodiments the fold of the natural heart valve leaflets 2005 potentially assists in sealing space around the frame 2000, potentially preventing back flow of blood around the frame 2000.

FIG. 20A is similar to the embodiments shown in FIGS. 18A-D and 19A-B, which can also trap and/or pinch the natural heart valve leaflet.

In some embodiments the wire arcs 2002 optionally grab natural heart valve leaflets at least on a side of the LVOT, potentially providing a benefit of keeping the natural heart valve leaflet away from a path of the LVOT.

In some embodiments the wire arcs 2002 optionally grab chordae (not shown in FIG. 20A, but shown as reference 106 in FIG. 1). Grabbing the chordae potentially provides anchoring for the frame and the heart valve prosthesis.

In some embodiments the rows of the wire arcs 2002 are arranged as rows of zigzag shaped wire arcs, rather than, by way of a non-limiting example, a typical stent with rhomboid shaped openings.

In some embodiments, the wire arcs 2002 are connected to the supports 2003 and not directly to each other, leaving a space through which a leaflet may pass and be clamped or pinched.

In some embodiments a tip of the wire arc 2002 has a bend, to continue the zigzag shape of the wire arc 2002. In some embodiments the bend is round, not sharp, thereby potentially preventing damage to heart walls or to leaflets pinched by the wire arcs 2002.

In some embodiments the wire arc 2002 pushes against a leaflet and produces a step shape against which the frame 2000 optionally anchors.

In some embodiments the wire arc 2002 does not pinch the leaflet 2005 and still pushes against the leaflet 2005 and produces a step shape against which the frame 2000 optionally anchors.

Reference is now made to FIG. 20B, which is a simplified line drawing of a heart valve prosthesis frame 2606 located in a heart according to an example embodiment of the invention.

FIG. 20B shows how in some embodiments the frame 2606 is shaped to conform to a shape of a natural mitral annulus 111 and to refrain from impinging upon the aortic valve 2602 and/or the LVOT 110.

FIG. 20B shows a heart 100 with a left atrium 101, a left ventricle 108, a left ventricular outflow tract (LVOT) 110 and an aorta 109. FIG. 20B also shows portions of the mitral valve such as the mitral leaflets 105, the mitral annulus 111, the chordae 106 and the papillary muscle 107.

The heart valve prosthesis frame 2606 is drawn approximately at a correct location in the heart 100. The heart valve prosthesis frame 2606 is also drawn on the right hand side of FIG. 20B and the following details are pointed out:

The example embodiments heart valve prosthesis frame 2606 shown in FIG. 20B includes three rows of arcs 2609 2610 2611, and a top, onion portion including one raised wire 2607 and one lower wire eye 2608. The shape of the onion portion is not symmetrical around an axis of the prosthesis frame 2606 in order that a side of the prosthesis frame 2606 which is next to the LVOT refrain from pushing upon the aortic valve 2602 and/or the LVOT 110 and/or refrain from pushing a mitral valve leaflet into the a left ventricular outflow tract (LVOT).

In some people, the mitral annulus is not planar. In some embodiments a three-dimensional shape of the top, onion portion, is also not plane and conforms to a shape of the mitral annulus, optionally by raising one side of the onion portion.

In some embodiments, a top view of the onion portion shows a D shape, where the side intended to be against the LVOT does not protrude as much as a circle. In some options the side intended to be against the LVOT is approximately straight.

Reference is now made to FIGS. 20C-20F, which are simplified illustrations of several views of the heart valve prosthesis frame 2606 of FIG. 20B.

FIG. 20C is a side view of the prosthesis frame 2606.

FIG. 20D is another side view of the prosthesis frame 2606, from a direction approximately perpendicular to the view direction of FIG. 20C.

FIG. 20D is a top view of the prosthesis frame 2606.

FIG. 20E is an isometric view of the prosthesis frame 2606.

FIGS. 20C-20F show the three rows of arcs 2609 2610 2611, the raised wire 2607 and the lower wire eye 2608 and additional wire eyes 2612 of the onion portion.

FIGS. 20C-20F also show optional slits 2614 in struts 2615 of the prosthesis frame 2606.

In some embodiments there are one or more slits 2614, for example 2 slits, 3 slits and more, which optionally connect to a delivery system for the prosthesis frame 2606.

In some embodiments there are one or more slits 2614, for example 2 slits, 3 slits and more, which are optionally sewn to a fabric forming part of a mitral valve prosthesis, by way of a non-limiting example as shown in FIGS. 19A and 19B.

In some embodiments there are one or more slits 2614, for example 2 slits, 3 slits and more, which are optionally sewn to a material forming mitral valve prosthesis leaflets as part of a synthetic mitral valve prosthesis, by way of a non-limiting example as shown in FIGS. 19A and 19B.

Reference is now made to FIGS. 20G-20H, which are simplified line drawings of two views of the heart valve prosthesis frame 2606 of FIG. 20B.

FIG. 20G is a side view of the prosthesis frame 2606 and FIG. 20H is another side view of the prosthesis frame 2606, from a direction approximately perpendicular to the view direction of FIG. 20C.

FIGS. 20G and 20H show the three rows of arcs 2609 2610 2611, the raised wire 2607 and the lower wire eye 2608 and additional wire eyes 2612 of the onion portion.

Reference is now made to FIGS. 20I-20K, which are simplified line drawings of cross-sectional views of optional embodiments of heart valve prosthesis frames according to an example embodiment of the invention.

FIG. 20I shows a prosthesis frame 2620 with a top onion portion pointing upstream. FIG. 20I shows a cross sectional view of the prosthesis frame 2620, with two rows of arcs 2621 2622, and a wire 2623 of the onion portion. FIG. 20I shows two rows of arcs 2621 2622, however three rows of arcs or more rows of arcs are optionally included with the wire 2623 of the onion portion.

FIG. 20J shows a prosthesis frame 2625 with a top onion portion pointing downstream. FIG. 20J shows a cross sectional view of the prosthesis frame 2625, with two rows of arcs 2626 2627, and a wire 2628 of the onion portion. FIG. 20J shows two rows of arcs 2626 2627, however three rows of arcs or more rows of arcs are optionally included with the wire 2628 of the onion portion.

FIG. 20K shows a prosthesis frame 2630 with a top onion portion pointing in a downstream direction followed by pointing in an upstream direction. FIG. 20K shows a cross sectional view of a prosthesis frame 2630, with two rows of arcs 2631 2632, and a wire 2633 of the onion portion. FIG. 20K shows two rows of arcs 2631 2632, however three rows of arcs or more rows of arcs are optionally included with the wire 2633 of the onion portion.

Reference is now made to FIG. 21A, which is a simplified line drawing of a cross sectional side view of heart valve prosthesis frame 2103 in place in a natural heart 2101 according to an example embodiment of the invention.

FIG. 21A shows an example of the frame 2103 grabbing onto natural heart valve leaflets 2105.

FIG. 21A shows the natural heart valve leaflets 2105 caught between wire arcs 2104 and an upper portion 2102 of the frame 2103.

FIG. 21A also show that the frame 2103 has been inserted into the mitral valve via a catheter 2109, which went through a right atrium 2106, a left atrium 2107, and partway into the left ventricle 2108.

Reference is now made to FIGS. 21B and 21C, which are simplified line drawings of a procedure for placing a heart valve prosthesis frame in place in a right atrioventricular valve of a natural heart according to an example embodiment of the invention. The right atrioventricular valve is a tricuspid valve, and FIGS. 21B and 21C show that various example embodiments provided with reference to the mitral valve are also applicable to a tricuspid valve, and their descriptions are meant to apply also to the tricuspid valve FIG. 21B shows an example of a catheter 2119 entering a right atrium 2106 of a natural heart.

FIG. 21C shows the natural heart valve leaflets 2115 caught between wire arcs and an upper portion of the frame 2113.

Reference is now made to FIG. 22A, which is a simplified flow chart illustration of a method for producing a heart valve prosthesis frame, according to an example embodiment of the invention.

The method of FIG. 22A includes producing (2202):
  supports designed to extend from an upstream side of a natural heart valve to a downstream side of the natural heart valve (2204); and
  wires attached to the plurality of supports (2206), wherein
    at least two of the wires are arranged as arcs connecting the supports, the arcs having two ends, each end attached to one of the supports, and a peak pointing from a center of the frame circumferentially outward and toward an upstream side of the heart valve prosthesis frame.

Reference is now made to FIG. 22B, which is a simplified flow chart illustration of a method for anchoring a prosthetic heart valve, according to an example embodiment of the invention.

The method of FIG. 22A includes:
  providing (2210) a heart valve prosthetic frame including:
    a plurality of supports designed to extend from an upstream side of a natural heart valve to a downstream side of the natural heart valve; and
    a plurality of wires attached to the plurality of supports, wherein
      at least two of the plurality of wires are arranged as arcs connecting the supports, the arcs having two ends, each end attached to one of the supports, and a peak pointing from a center of the frame circumferentially outward;
  inserting the heart valve prosthetic frame into an annulus of a natural heart valve (2212);
  expanding the heart valve prosthetic frame (2214);
  allowing a natural heart valve leaflet to protrude between the at least two wires (2216); and
  using at least one of the plurality of wires to anchor against the natural heart valve leaflet (2218).

In some embodiments, further comprising clamping the natural heart valve leaflet between at least one of the wires and an upper portion of the frame.

In some embodiments, further comprising clamping the natural heart valve leaflet between at least two of the wires.

In some embodiments, further comprising trapping the annulus of the natural heart valve between at least one of the wires and an upper portion of the frame.

Reference is now made to FIG. 23, which is a simplified flow chart illustration of a method for producing a heart valve prosthesis frame, according to an example embodiment of the invention.

The method of FIG. 23 includes:
  producing a frame (2302) including:
    a hollow tube shape for allowing blood to flow through (2304);
    an upstream portion of the hollow tube designed to expand to have at least one dimension wider than a native heart valve annulus (2306);
    a downstream portion of the hollow tube attached to the upstream portion, the downstream portion also designed to expand to have at least a portion with at least one dimension wider than the native heart valve annulus (2308);
  wherein
  the downstream portion is shaped to have one side of the downstream portion of the hollow tube extend less from a center of the hollow tube than an opposite side of the hollow tube.

Reference is now made to FIG. 24, which is a simplified flow chart illustration of a method for producing a heart valve prosthesis frame, according to an example embodiment of the invention.

The method of FIG. 24 includes:
  producing a frame (2402) including:
    a hollow tube shape made of a shape memory material (2404);
    an upstream portion designed to expand to have at least one dimension wider than a native heart valve annulus (2406);
    a center portion attached to the upstream portion, designed to expand no wider than a native heart valve annulus (2408); and a downstream portion attached to the center portion (2410), the downstream portion also designed to expand to:
have at least one dimension wider than the native heart valve annulus; and
have protrusions away from a center axis of the frame which point upstream.

Reference is now made to FIG. 25, which is a simplified flow chart illustration of a method for shaping a heart valve prosthesis frame, according to an example embodiment of the invention.

The method of FIG. 25 includes:
receiving a heart valve prosthesis frame within a catheter, the heart valve prosthesis frame including (2502):
a hollow tube shape made of a shape memory material (2504);
an upstream portion designed to expand to have at least one dimension wider than a native heart valve annulus (2506);
a center portion attached to the upstream portion, designed to expand no wider than a native heart valve annulus (2508); and
a downstream portion attached to the center portion (2510), the downstream portion also designed to expand to:
have at least one dimension wider than the native heart valve annulus; and
have protrusions away from a center axis of the frame which point upstream; and extruding the frame from the catheter (2512).

Reference is now made to FIGS. 26A-26B, which are simplified line drawings of two views of a heart valve prosthesis frame 2640 according to an example embodiment of the invention.

FIG. 26A is a side view of the prosthesis frame 2640 and FIG. 26B is another side view of the prosthesis frame 2640, from a direction approximately perpendicular to the view direction of FIG. 26A.

FIGS. 26A and 26B show three rows of arcs 2641 2642 2643.

FIG. 26A shows onion portion wire eyes 2644 2645.

FIG. 26B shows a raised onion portion wire eye 2646, and a lower onion portion wire eye 2647.

In some embodiments a third, top row of arcs is used to provide structural strength to the heart valve prosthesis frame 2640, optionally at a same height as the onion portion. In some embodiments the third, top row of arcs is used to provide structural strength to the heart valve prosthesis frame 2640 by optionally having a similar profile curvature as the onion, atrial portion.

In some embodiments the first and second lower rows of arcs are configured for anchoring to the heart anatomy.

In some embodiments the first and second lower rows of arcs are optionally configured for supporting commissure struts from collapsing radially.

Reference is now made to FIGS. 26C-26D, which are simplified line drawings of two views of a heart valve prosthesis frame 2650 according to an example embodiment of the invention.

FIG. 26C is a cross-sectional side view of the prosthesis frame 2650 and FIG. 26D is a side view of the prosthesis frame 2650, from a direction approximately perpendicular to the view direction of FIG. 26C.

FIG. 26D shows three rows of arcs 2651 2652 2653.

FIG. 26C shows the middle row of arcs 2652 jutting out from the circumference of the prosthesis frame 2650. FIG. 26C shows the bottom row of arcs 2651 in-line with the circumference of the prosthesis frame 2650.

FIGS. 26C and 26D show onion portion wire eyes 2654.

FIGS. 26C and 26D show, using dashed lines, a top 2658 of prosthetic mitral valve leaflets and a bottom 2659 of the prosthetic mitral valve leaflets.

FIG. 26C shows, using dashed lines:
the atrial heart wall 2655 next to the onion portion wire eyes 2654;
the mitral annulus 2656 between the middle row of arcs 2652 and the onion portion wire eyes 2654; and
the ventricle walls next to the bottom of the prosthesis frame 2650 and/or next to the bottom row of arcs 2651.

Reference is now made to FIGS. 26E-26F, which are simplified line drawings of two views of a heart valve prosthesis frame 2660 according to an example embodiment of the invention.

FIG. 26E is a cross-sectional side view of the prosthesis frame 2660 and FIG. 26F is a side view of the prosthesis frame 2660, from a direction approximately perpendicular to the view direction of FIG. 26F.

FIGS. 26E and 26F show an example embodiment where a top row of arcs 2663 is optionally configured to jut upward along walls of a lumen of the prosthesis frame 2660 at a level higher than top onion portion wire eyes 2664 jut away from the lumen, and the top row of arcs 2663 is optionally used to attach a top 2668 of prosthetic mitral leaflets. In such embodiments the prosthetic mitral valve leaflets optionally shape a longer mitral valve than if the prosthetic mitral valve leaflets were attached at the level where the top onion portion wire eyes 2664 jut away from the lumen.

FIGS. 26E and 26F show three rows of arcs 2661 2662 2663.

The middle and bottom rows of arcs 2661 2662 jut out from a circumference of the prosthesis frame 2660.

FIGS. 26E and 26F show, using dashed lines, a top 2668 of prosthetic mitral valve leaflets and a bottom 2669 of the prosthetic mitral valve leaflets.

FIG. 26E shows, using dashed lines:
the atrial heart wall 2665 next to the onion portion wire eyes 2664;
the mitral annulus 2666 between the middle row of arcs 2662 and the onion portion wire eyes 2664; and
an optional fold 2667 in ventricle walls between the middle row of arcs 2662 and the bottom row of arcs 2661.

The mitral annulus 2666 and the optional fold 2667 serve to anchor the prosthesis frame 2660 in the heart.

FIG. 26F also shows frame struts 2698. It is noted that wherever struts and arcs are shown in the present application, in some embodiments a space between struts may not include a same number of arcs as a neighboring space between struts. By way of a non-limiting example, one space may include two arcs and a neighboring space may include three struts.

Reference is now made to FIGS. 26G-26H, which are simplified line drawings of two views of a heart valve prosthesis frame 2670 according to an example embodiment of the invention.

FIG. 26G is a cross-sectional side view of the prosthesis frame 2670 and FIG. 26H is a side view of the prosthesis frame 2670, from a direction approximately perpendicular to the view direction of FIG. 26G.

FIGS. 26G and 26H show an example embodiment where a top row of arcs 2673 is optionally configured to jut upward along walls of a lumen of the prosthesis frame 2670 at a level higher than top onion portion wire eyes 2674 jut away from the lumen, and the top row of arcs 2673 is optionally used to attach a top 2678 of prosthetic mitral leaflets. In such embodiments the prosthetic mitral valve leaflets optionally shape a longer mitral valve than if the prosthetic mitral valve leaflets were attached at the level where the top onion portion wire eyes 2674 jut away from the lumen.

FIGS. 26G and 26H show three rows of arcs 2671 2672 2673.

The bottom row of arcs 2671 juts out from a circumference of the lumen of the prosthesis frame 2670.

The middle row of arcs 2672 does not jut out from the circumference of the lumen of the prosthesis frame 2670, and is configured to remain in-line with the circumference of the lumen of the prosthesis frame 2670.

The example embodiment of FIGS. 26G and 26H also shows the middle row of arcs 2672 optionally configured to be in-line with the circumference of the lumen of the prosthesis frame 2670. This leaves more room 2677 between the top onion portion wire eyes 2674 and the bottom row of arcs 2671 for the mitral annulus and/or natural mitral leaflets to enter and be used for anchoring the prosthesis frame 2670.

FIGS. 26G and 26H show, using dashed lines, a top 2678 of prosthetic mitral valve leaflets and a bottom 2679 of the prosthetic mitral valve leaflets.

FIG. 26G shows, using dashed lines:
the atrial heart wall 2675 next to the onion portion wire eyes 2674; and
the mitral annulus and/or natural mitral leaflets 2676 between the onion portion wire eyes 2674 and the bottom row of arcs 2671.

In some embodiments, a height of the bottom row of arcs 2671 is optionally greater than an inter-row spacing between the bottom row of arcs 2671 and the middle row of arcs 2672.

In some embodiments, a distance by which the bottom row of arcs 2671 juts out from the lumen of the prosthesis frame 2670 is optionally greater than an inter-row spacing between the bottom row of arcs 2671 and the middle row of arcs 2672.

Reference is now made to FIG. 27A, which is a simplified illustration of a heart valve prosthesis frame 2700 located in a heart according to an example embodiment of the invention.

FIG. 27A shows how in some embodiments a mitral annulus 2705 enters between a second row of arcs 2702 and an onion top portion 2704 of a heart valve prosthesis frame 2700.

FIG. 27A also shows, in an enlarged view 2707, a single arc 2708 from one of optionally three row of arcs 2701 2702 2703. The single arc 2708 is shown with a round, or at least non-sharp tip 2709.

FIG. 27A shows three rows of arcs 2701 2702 2703, optionally jutting out from a circumference of the prosthesis frame 2700.

FIG. 27 shows, using dashed lines:
the mitral annulus 2705 between the middle row of arcs 2702 and the top onion portion 2704; and
an optional fold 2706 in ventricle walls between the middle row of arcs 2702 and the bottom row of arcs 2701.

Reference is now additionally made to FIG. 27B, which is a simplified illustration of a single arc in a heart valve prosthesis frame according to an example embodiment of the invention.

FIG. 27B shows an arc 2712 having a sharp tip 2713, in contrast to the tip 2709 shown in FIG. 27A.

Reference is now additionally made to FIG. 27C, which is a simplified illustration of the arc of FIG. 2B.

FIG. 27C shows the arc 2712 with the sharp tip 2713, in a compressed shape as occurs when the heart valve prosthesis frame is compressed in a delivery system such as a delivery capsule or a delivery catheter.

It is noted that the sharp tip 2713 can optionally prick heart tissue yet not penetrate deep into the heart tissue, as the sharp tip is not long and the arc is wide, which prevents deep penetration.

In some embodiments some arc rows may have all arcs with a sharp tip such as shown in FIGS. 27B 27C and some arc rows may have all arcs with a round tip such as shown in FIG. 27A.

In some embodiments a same arc row may have some arcs with a sharp tip such as shown in FIGS. 27B 27C and some arcs with a round tip such as shown in FIG. 27A.

Reference is now made to FIGS. 28A and 28B, which are simplified illustrations of a heart valve prosthesis frame 2800 located in a heart according to an example embodiment of the invention.

FIG. 28A shows components of the heart valve prosthesis frame 2800 and the heart in more detail, and FIG. 28B shows a direction 2808 of view used in drawing FIG. 28A.

FIG. 28A shows how in some embodiments chordae 2805 connected to a papillary muscle 2807 and to a natural mitral valve leaflet 2806 are optionally captured between arcs 2801.

FIG. 28A shows how in some embodiments one or more natural mitral valve leaflets 2806 are optionally captured between a first row of arcs 2801 and a second row of arcs 2802.

In the example embodiment of FIG. 28A an anterior leaflet 2806 is optionally captured.

In some embodiments the anterior leaflet 2806 is optionally kept away from the LVOT, to potentially reduce or eliminate LVOT obstruction.

In some embodiments one or more of the arcs or one or more of the arc rows 2801 2802 2803 is optionally covered with fabric and/or Pericard, which can potentially reduce friction between the arcs and heart tissue.

In some embodiments the arcs optionally lift and/or hold an anterior leaflet of the mitral valve to reduce LVOT obstruction.

In some embodiments one or more eyes of an onion portion 2804A 2804B 2804C is optionally raised, optionally on the same side as the anterior leaflet 2806.

Reference is now made to FIGS. 28C and 28D, which are illustrations of a heart and a prosthetic mitral valve placed in the heart.

FIG. 28C is composed of a photograph of a heart and a prosthetic mitral valve placed in the heart, taken from the ventricle side, and overlay lines added to point out locations of parts of the natural heart and components of the prosthetic mitral valve.

FIGS. 28C and 28D show a view from an apex of a left ventricle toward the mitral valve. The mitral valve is seen from the ventricle side.

FIG. 28D shows a line drawing illustration of the contents of FIG. 28C.

FIGS. 28C and 28D show parts of the heart: an anterior leaflet 2815 and a posterior leaflet 2817, papillary muscles 2807, and chordae 2805.

FIGS. 28C and 28D show components of the prosthetic mitral valve, including arcs 2812 and prosthetic leaflets 2816.

In the example embodiment shown in FIGS. 28C and 28D prosthetic leaflets 2816 are shown in the three prosthetic mitral valve.

Reference is now made to FIGS. 29A and 29B, which are simplified line drawing illustrations of a cross sectional side view of delivery of a heart valve prosthesis frame into place in a natural heart according to an example embodiment of the invention.

FIGS. 29A and 29B show an example of a catheter 2905 inserted into a heart 2911 via a trans-apical approach 2904.

The heart 2911 shows, inter alia, the ventricle 2902, the atrium 2901 and the mitral valve 2910.

FIGS. 29A and 29B show a delivery system for delivering a heart valve prosthesis 2909, the delivery system including a capsule control portion 2906, and a capsule 2913 including a distal part 2908 and a proximal part 2907.

FIG. 29A shows the capsule 2913 approximately at a correct position for placing a prosthetic mitral valve 2909 in the heart 2911.

FIG. 29B shows the distal part 2908 and the proximal part 2907 of the capsule 2913 separated and the prosthetic mitral valve 2909 opened at its target location.

Reference is now made to FIGS. 30A-30I, which are images of a prosthetic mitral valve in a process of deployment from a delivery capsule according to an example embodiment of the invention.

Some or all of FIGS. 30A-30I show the following components:
- a proximal part 3001 of the delivery capsule;
- a distal part 3002 of the delivery capsule;
- a pin 3003 in the distal part of the delivery capsule;
- a control wire 3004 for controlling the distal part 3002 of the delivery capsule;
- a bottom row of arcs 3005;
- a second row of arcs 3006;
- a third row of arcs 3007;
- an onion row of eyes 3008; and optional onion eyes 3009 for holding on to the prosthetic mitral valve after other components have been released from the delivery capsule.

An example process of deployment from the delivery capsule is now described:

FIG. 30A shows the delivery capsule closed.

FIG. 30B shows the distal part 3002 of the delivery capsule slightly away from the proximal part 3001, and some of the prosthetic mitral valve may be seen, for example the bottom row of arcs 3005.

FIG. 30C shows the distal part 3002 of the delivery capsule further away from the proximal part 3001.

FIG. 30D shows the bottom row of arcs 3005 released from the distal part 3002 of the delivery capsule.

FIG. 30E also shows the bottom row of arcs 3005 released from the distal part 3002 of the delivery capsule, and the second row of arcs 3006 starting to expand.

FIG. 30F shows the bottom row of arcs 3005 and the second row of arcs 3006 more expanded, and the third row of arcs 3007 starting to expand.

FIG. 30G shows the three rows of arcs 3005 3006 3007 more expanded.

FIG. 30H shows the three rows of arcs 3005 3006 3007 and an onion row of eyes 3008 starting to emerge from the distal part 3002 of the delivery capsule. It is noted that the onion row of eyes 3008 in the example embodiment of FIGS. 30A-30I does not include some of the onion eyes 3009, optionally two opposing onion eyes. A top view of FIG. 30H would show the prosthetic mitral valve still somewhat compressed from a circular or D shape into a figure-8, due to the two opposing onion eyes 3009 being still held within the distal part 3002 of the delivery capsule. At this point the prosthetic mitral valve is still connected to its delivery system, and not fully released. Such connection potentially enables controlling the prosthetic mitral valve, before releasing the prosthetic mitral valve completely.

FIG. 30I shows the prosthetic mitral valve fully outside the delivery capsule.

Reference is now made to FIGS. 31A and 31B, which are simplified line drawings of loading and unloading of a prosthetic mitral valve into a delivery capsule according to an example embodiment of the invention.

FIGS. 31A and 31B show how elongated arcs and/or eyes in a prosthetic frame structure optionally attached to one or more pins in a delivery capsule in order to release the prosthetic frame structure from the delivery capsule and maintain a final attachment to the prosthetic frame structure before completely releasing the prosthetic frame structure.

FIGS. 31A and 31B show an outside tube 3112 of a delivery capsule 3110 or a catheter 3110, and a piston 3108 inside the delivery capsule/catheter 3110.

FIG. 31A shows a top of a prosthetic heart valve frame 3101 being inserted into a delivery capsule 3110 or a catheter 3110.

FIG. 31B shows a top of a prosthetic heart valve frame 3101 further inside the delivery capsule/catheter 3110, and being pushed out of the delivery capsule/catheter 3110.

FIGS. 31A and 31B show optional wire loops or eyes 3103 3104 3105, optionally part of an onion portion of the prosthetic heart valve frame 3101, and tips of arcs 3102.

FIGS. 31A and 31B show a wire loop or eye 3105, optionally part of an onion portion of the prosthetic heart valve frame 3101, placed on an optional pin 3106 in the piston 3108 in the delivery capsule/catheter 3110. The eye 3105 is shown optionally reaching further into the delivery capsule/catheter 3110 than other eyes 3103 3104 or arcs 3102.

The pin 3106 potentially enables pulling the prosthetic heart valve frame 3101 into the delivery capsule/catheter 3110 tube.

In some embodiments, the piston 3108 optionally pushes the prosthetic heart valve frame 3101 by pressing the longer elements of the prosthetic heart valve frame 3101, by way of a non-limiting example the wires 3103 of the onion portion.

In some embodiments the eye 3105 includes beads 3107 or a widening 3107 of the eye 3105 which potentially prevent the eye 3105 slipping on the pin 3106 and/or grasp the pin 3106 better.

Reference is now made to FIG. 31C which is an image of a delivery capsule and a prosthetic mitral valve according to an example embodiment of the invention.

FIG. 31C shows components of a prosthetic mitral valve 3101 including arcs 3102 and onion portion wires 3103.

FIG. 31C also shows a portion of a delivery capsule 3110 and a pin 3106 for optionally attaching a wire loop of the prosthetic mitral valve 3101 such as the eye 3105 shown in FIGS. 31A and 31B.

Reference is now made to FIGS. 32A-32D, which are simplified illustrations of a delivery capsule in various stages of delivering a prosthetic mitral valve according to an example embodiment of the invention.

FIGS. 32A-32D show a delivery capsule including a distal portion 3202 and a proximal portion 3203, a delivery capsule tip 3204, and a prosthetic mitral valve 3206.

Figure 32B:
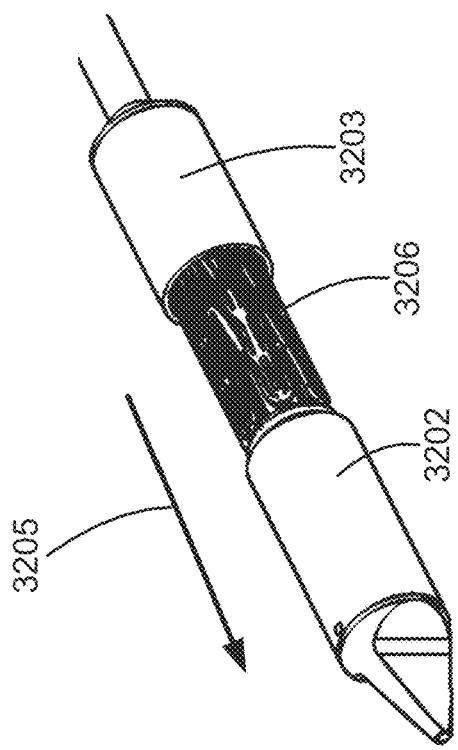
Figure 32D:
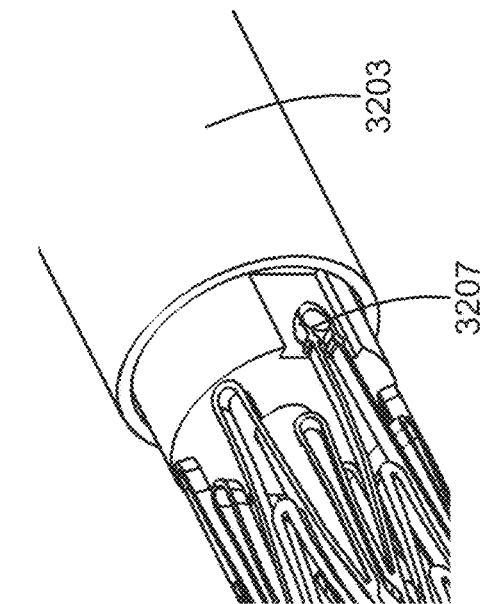
Figure 32A:
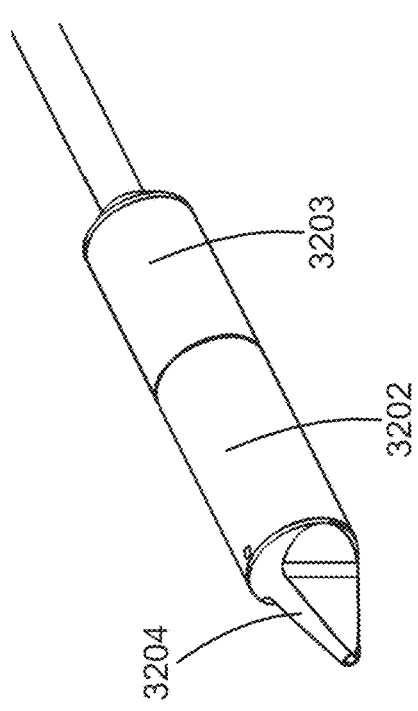

FIG. 32A shows the delivery capsule closed, including the distal portion 3202 and the proximal portion 3203.

Figure 32C:
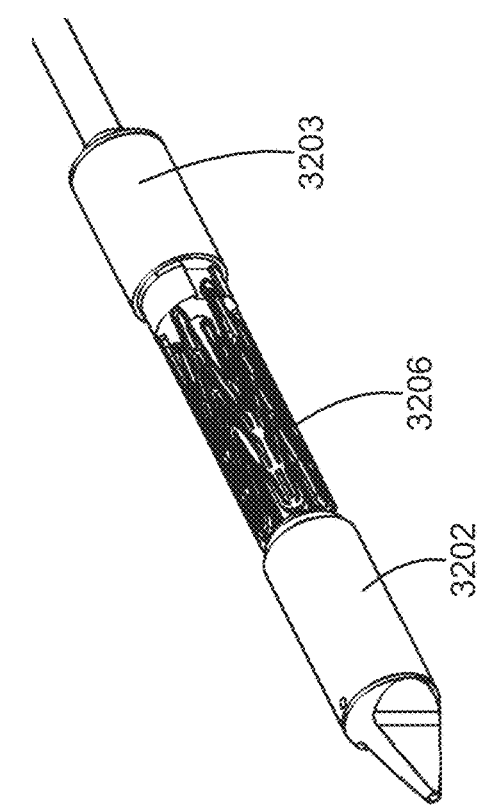

In some embodiments the delivery capsule tip 3204 is optionally shaped as shown in FIGS. 32A-32C. In some embodiments the shape of the delivery capsule tip 3204 optionally enables identifying an angle at which the delivery capsule and the prosthetic mitral valve 3206 are rotated relative to a longitudinal axis of the delivery capsule.

In some embodiments the delivery capsule and/or the delivery capsule tip 3204 optionally include echo positioning and/or rotation markers.

FIG. 32B shows the delivery capsule starting to open by optionally pushing the distal portion 3202 away from the proximal portion 3203. Other methods of opening the delivery capsule can be performed, such as pulling the proximal portion 3203 away from the distal portion 3202, or alternately or simultaneously pushing and pulling.

FIG. 32C shows the delivery capsule more open, to an extent at which the prosthetic mitral valve 3206 should be expanded. FIG. 32C is showing the prosthetic mitral valve 3206 still compressed only to demonstrate one example way in which the prosthetic mitral valve 3206 is packaged within a delivery capsule.

FIG. 32D shows a portion of FIG. 32C enlarged, showing an optional pin 3207 for attaching the prosthetic mitral valve 3206, optionally as described with reference to FIGS. 31A-31C.

In some embodiments the drawings of FIG. 32C is of a stage where the prosthetic mitral valve 3206 is released from the pin 3207.

Reference is now made to FIGS. 33A-33D, which are simplified illustrations of a delivery capsule in various stages of delivering a prosthetic mitral valve according to an example embodiment of the invention.

FIGS. 33A-33D show a delivery capsule including a distal portion 3302 and a proximal portion 3303, a delivery capsule tip 3304, and a prosthetic mitral valve 3306.

Figure 33B:
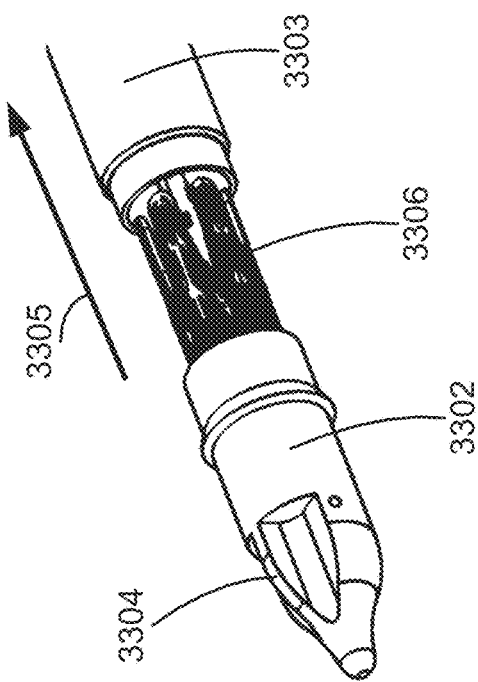
Figure 33D:
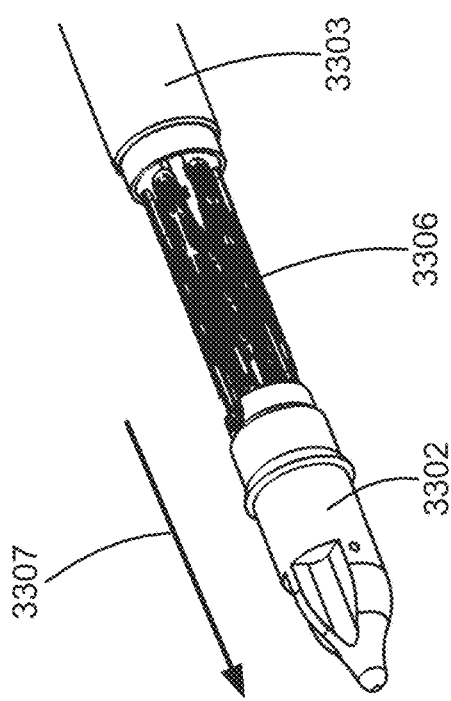
Figure 33A:
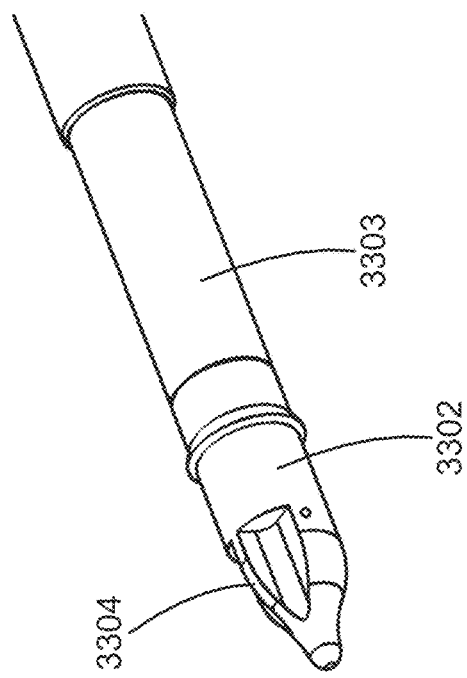

FIG. 33A shows the delivery capsule closed, including the distal portion 3302 and the proximal portion 3303.

In some embodiments the delivery capsule tip 3304 is optionally shaped as shown in FIGS. 33A-33D. In some embodiments the shape of the delivery capsule tip 3304 optionally enables identifying an angle at which the delivery capsule and the prosthetic mitral valve 3306 are rotated relative to a longitudinal axis of the delivery capsule.

In some embodiments the delivery capsule and/or the delivery capsule tip 3304 optionally include echo positioning and/or rotation markers.

FIG. 33B shows the delivery capsule starting to open by optionally pulling the proximal portion 3303 away from the distal portion 3302. FIG. 33B also shows the prosthetic mitral valve 3306. In some embodiments some parts of the prosthetic mitral valve 3306 may expand when the delivery capsule is opened as shown in FIG. 33B.

Figure 33C:
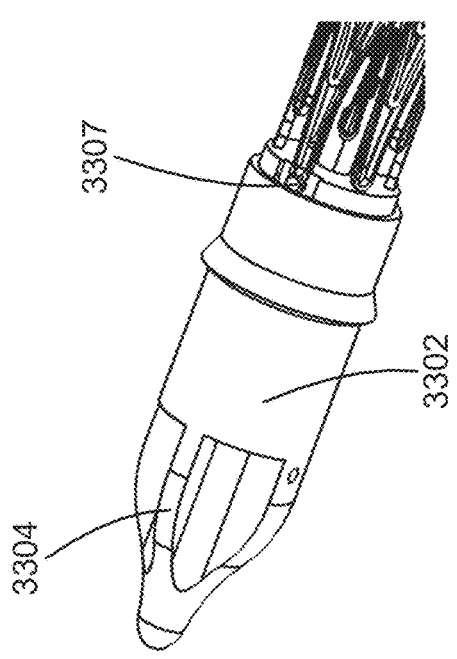

FIG. 33C shows the delivery capsule from a different angle of view, showing a peek at an optional pin 3307 for attaching the prosthetic mitral valve 3306, optionally as described with reference to FIGS. 31A-31C.

FIG. 33D shows the delivery capsule opening more by optionally pushing the distal portion 3302 away from the proximal portion 3303. FIG. 33D shows the prosthetic mitral valve 3306. In some embodiments the prosthetic mitral valve 3306 expands when the delivery capsule is opened as shown in FIG. 33D, and in some embodiments the prosthetic mitral valve 3306 is optionally released from the optional pin 3307.

Reference is now made to FIGS. 34A-34C, which are simplified illustrations of various methods of releasing a prosthetic mitral valve from a delivery capsule according to an example embodiment of the invention.

FIGS. 34A-34C show a delivery capsule including a first portion 3401 of a delivery capsule and a second portion 3402 of a delivery capsule and a prosthetic mitral valve 3403. For convenience, an atrial portion 3404 of the prosthetic mitral valve 3403 is pointed out in the drawings of FIGS. 34A-34C.

FIG. 34A shows a delivery of the prosthetic mitral valve 3403 by first moving the first portion 3401 of the delivery capsule off the prosthetic mitral valve 3403, then moving the second portion 3402 of the delivery capsule off the atrial portion 3404 of the prosthetic mitral valve 3403, placing the prosthetic mitral valve 3403 outside the delivery capsule.

FIG. 34B shows a delivery of the prosthetic mitral valve 3403 by first moving the second portion 3402 of the delivery capsule off the atrial portion 3404 of the prosthetic mitral valve 3403, then moving the first portion 3401 of the delivery capsule off the rest of the prosthetic mitral valve 3403, placing the prosthetic mitral valve 3403 outside the delivery capsule.

FIG. 34C shows a delivery of the prosthetic mitral valve 3403 by moving the second portion 3402 of the delivery capsule and the first portion 3401 of the delivery capsule off the prosthetic mitral valve 3403 simultaneously, placing the prosthetic mitral valve 3403 outside the delivery capsule.

Reference is now made to FIGS. 34D and 34E, which are simplified illustrations of various methods of releasing a prosthetic mitral valve from a delivery capsule according to an example embodiment of the invention.

FIGS. 34D and 34E show a delivery capsule 3405 and a prosthetic mitral valve 3406. For convenience, an atrial portion 3407 of the prosthetic mitral valve 3406 is pointed out in the drawings of FIGS. 34D and 34E.

FIG. 34D shows a delivery of the prosthetic mitral valve 3406 by pulling the delivery capsule 3405 off the prosthetic mitral valve 3406 in a direction of the atrial portion 3407 of the prosthetic mitral valve 3406, placing the prosthetic mitral valve 3406 outside the delivery capsule 3405.

FIG. 34E shows a delivery of the prosthetic mitral valve 3406 by pushing the prosthetic mitral valve 3406 out of the delivery capsule 3405 in a direction opposite the direction of the atrial portion 3407 of the prosthetic mitral valve 3406, placing the prosthetic mitral valve 3406 outside the delivery capsule 3405.

Reference is now made to FIG. 35, which is a simplified illustration of a delivery system for delivering a prosthetic mitral valve by catheter according to an example embodiment of the invention.

FIG. 35 shows the following components as part of a delivery system 3500:
- an optional control knob 3503 for controlling a proximal portion of a delivery capsule. In some embodiments, for example in case of taking a trans-apical route for inserting the prosthetic mitral valve, the proximal portion optionally contains a portion of the prosthetic mitral valve intended for placement in the left ventricle;
- an optional control knob 3504 for controlling a distal portion of a delivery capsule. In some embodiments, for example in case of taking a trans-apical route for inserting the prosthetic mitral valve, the distal portion optionally contains a portion of the prosthetic mitral valve intended for placement in the left atrium;
- an optional control knob 3506 for controlling rotation and/or orientation of a delivery capsule;
- an optional control knob 3505 for controlling height of the prosthetic mitral valve within the heart. In some embodiments, for example when inserting the prosthetic mitral valve via a trans-apical route, the control knob 3505 optionally moves the prosthetic mitral valve forward or backward, which controls the height of the prosthetic mitral valve within the heart.

an optional Connector 3502 for an optional stabilizing arm.

Reference is now made to FIG. 36, which is a simplified illustration of a prosthetic mitral valve frame according to an example embodiment of the invention.

FIG. 36 is an illustration of a lumen of a frame 3600 cut so that it lies flat.

FIG. 36 shows, from a lower, downstream end of the lumen of the frame 3600 toward a higher, upstream end of the lumen of the frame 3600: one or more rows of arcs, by way of a non-limiting example a first row of arcs 3601, a second row of arcs 3602 and a third row of arcs 3603.

FIG. 36 also shows a row of onion portion arcs/eyes 3604A 3604B 3604C. FIG. 36 provides an opportunity to illustrate some properties of the frame 3600.

In some embodiments, a tip 3607 of an arc 3608 may be more distant from a base of the arc 3608 than an inter-arc distance 3609 between a base 3612 of one row of arcs, for example row of arcs 3601 and a base 3613 of the next row of arcs 3602. Such an arc may be bent to jut out from a circumference of a lumen formed by the frame, and reach walls of the heart, and/or trap a fold of a heart wall or a leaflet, optionally without bending at a great angle, for example by bending at 30 degrees or 45 degrees.

In some embodiments, some tips 3615 of an arc may be sharp, and some tips 3636 may be rounded.

In some embodiments, onion portion arcs/eyes 3604A 3604B 3604C may extend different lengths. By way of a non-limiting example, some onion portion arcs/eyes 3604A may extend more than other onion portion arcs/eyes 3604B. By way of another non-limiting example, some onion portion arcs/eyes 3604C may extend beyond others, and potentially be suitable for attaching to a pin, and optionally be the last components of a frame 3600 to be released during deployment.

It is expected that during the life of a patent maturing from this application many relevant shape memory materials will be developed and the scope of the term shape memory material is intended to include all such new technologies a priori.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of anchoring a prosthetic heart valve, comprising:

providing a heart valve prosthetic frame including:

a plurality of struts, each one of which is designed to extend from an upstream side of a heart valve prosthesis to a downstream side of the heart valve prosthesis; and a plurality of connectors attached to the plurality of struts defining a center lumen of the frame, wherein:
  at least two of the plurality of connectors are arranged as arcs connecting the struts, the arcs having two ends, each end attached to one of the struts, and a peak pointing from a center of the frame radially outward from the circumference of the frame; and
  the plurality of connectors are arranged as at least two rows, each row circumnavigating the center lumen of the frame;
inserting the heart valve prosthetic frame into an annulus of a natural heart valve;
expanding the heart valve prosthetic frame;
allowing a natural heart valve leaflet to protrude inward into the center lumen of the frame, between the at least two connectors; and
using at least one of the plurality of connectors to anchor the frame against the natural heart valve leaflet.

2. The method of claim 1, and further comprising clamping the natural heart valve leaflet between at least one of the connectors and an upper portion of the frame.

3. The method of claim 1, and further comprising clamping the natural heart valve leaflet between at least two of the connectors.

4. The method of claim 1, and further comprising trapping the annulus of the natural heart valve between at least one of the connectors and an upper portion of the frame.

5. The method of claim 1, in which the frame comprises at least three rows;
  the allowing a natural heart valve leaflet to protrude between the at least two connectors comprises allowing the natural heart valve leaflet to protrude between at least three connectors at at least two levels along the natural heart valve leaflets; and
  using the at least three connectors to anchor the frame against the natural heart valve leaflet.

6. A heart valve prosthesis comprising a frame, the frame comprising:
  a plurality of struts designed to extend from an upstream side of a heart valve prosthesis to a downstream side of the heart valve prosthesis; and
  a plurality of connectors attached to the plurality of struts defining a center lumen of the frame, wherein:
  at least some of the plurality of connectors are arranged as arcs connecting the struts, the arcs having two ends, each end attached to one of the struts, and a peak pointing from a center of the frame radially outward from the circumference of the frame and toward the upstream side of the frame; and
  the plurality of connectors are arranged as at least two rows, each row circumnavigating the center lumen of the frame, and
  wherein the number of the plurality of struts is selected to leave room for anchoring of the frame by the frame capturing natural heart valve leaflets protruding inward, into the center lumen of the frame, between the struts.

7. The heart valve prosthesis of claim 6, in which the rows are spaced apart at least 2 millimeters, allowing leaflets of the natural heart valve to be caught between the connectors.

8. The heart valve prosthesis of claim 6, in which the frame comprises at least three rows, sized so that leaflets of the natural heart valve can protrude inward into the center lumen of the frame, between the rows, to be caught between the connectors at at least two levels along the leaflets of the natural heart.

9. The heart valve prosthesis of claim 6, in which the rows are spaced apart in a range of 2 millimeters to 8 millimeters.

10. The heart valve prosthesis of claim 6, in which the plurality of struts consists of a number of struts selected from a group consisting of a strut count of:
  three; and
  six.

11. The heart valve prosthesis of claim 6, in which the rows are designed to grab natural heart valve leaflets only on a side of the Left Ventricular Outflow Tract (LVOT), thereby keeping the natural heart valve leaflet away from a path of the LVOT.

12. The heart valve prosthesis of claim 6, wherein a downstream portion of the frame is shaped to have one side of the downstream portion of the frame extend less from a center of a lumen of the frame than an opposite side of the downstream portion of the frame.

13. The heart valve prosthesis of claim 6, wherein a plurality of tops of arcs of the connector arcs are sharp.

14. The heart valve prosthesis of claim 6, wherein tops of arcs of a bottom row of connector arcs are sharp.

15. The heart valve prosthesis of claim 6, wherein tops of arcs of a row of connector arcs upstream of a bottom row of connector arcs do not point away from a center axis of the frame.

16. The heart valve prosthesis of claim 6, wherein only some tops of arcs of the connector arcs points away from a center axis of the frame.

17. The heart valve prosthesis of claim 6, wherein tops of an upstream row of connector arcs point parallel to a center axis of the frame and extend further upstream than the struts.

18. The heart valve prosthesis of claim 6, in which the arcs have a shape which includes a tip designed for the connector arcs to bend when the frame is compressed into a catheter.

19. The heart valve prosthesis of claim 6, and further comprising a plurality of flexible sheet leaflets attached to the frame, the plurality of leaflets arranged as a one-directional valve opening to fluid pressure in a downstream direction and closing to fluid pressure in an upstream direction.

20. A method for producing a heart valve prosthesis frame, the method comprising producing:
  a plurality of struts designed to extend from an upstream side of a heart valve prosthesis to a downstream side of the heart valve prosthesis; and
  a plurality of connectors attached to the plurality of struts defining a center lumen of the frame, wherein:
  the plurality of connectors are arranged as arcs connecting the struts, the arcs having two ends, each end attached to one of the struts, and a peak pointing from a center of the frame radially outward from the circumference of the frame and toward an upstream side of the frame; and
  the plurality of connectors are arranged as at least two rows, each row circumnavigating the center lumen of the frame, and
  wherein the number of the plurality of struts is selected to leave room for anchoring of the frame by the frame capturing natural heart valve leaflets protruding inward into the center lumen of the frame.

* * * * *